(12) United States Patent
Zhou et al.

(10) Patent No.: US 11,590,242 B2
(45) Date of Patent: Feb. 28, 2023

(54) ANTIBODY-MEDIATED AUTOCATALYTIC, TARGETED DELIVERY OF NANOCARRIERS TO TUMORS

(71) Applicant: Yale University, New Haven, CT (US)

(72) Inventors: Jiangbing Zhou, Cheshire, CT (US); James Hansen, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 569 days.

(21) Appl. No.: 16/310,372

(22) PCT Filed: Jun. 15, 2017

(86) PCT No.: PCT/US2017/037754
§ 371 (c)(1),
(2) Date: Dec. 14, 2018

(87) PCT Pub. No.: WO2017/218825
PCT Pub. Date: Dec. 21, 2017

(65) Prior Publication Data
US 2019/0247515 A1    Aug. 15, 2019

Related U.S. Application Data

(60) Provisional application No. 62/350,423, filed on Jun. 15, 2016.

(51) Int. Cl.
*A61K 47/69*     (2017.01)
*A61P 35/00*     (2006.01)
*A61K 47/68*     (2017.01)
*A61K 31/502*    (2006.01)
*A61K 31/704*    (2006.01)

(52) U.S. Cl.
CPC ........ *A61K 47/6937* (2017.08); *A61K 31/502* (2013.01); *A61K 31/704* (2013.01); *A61K 47/6843* (2017.08); *A61K 47/6935* (2017.08); *A61P 35/00* (2018.01)

(58) Field of Classification Search
CPC .............. A61K 47/6937; A61K 31/502; A61K 31/704; A61K 47/6843; A61P 35/00; C07K 2317/77; C07K 2317/73; C07K 2317/622
See application file for complete search history.

(56) References Cited

U.S. PATENT DOCUMENTS

| | | | |
|---|---|---|---|
| 4,812,397 A | 3/1989 | Wesibart |
| 4,952,394 A | 8/1990 | Senter |
| 5,618,528 A | 4/1997 | Cooper |
| 5,780,033 A | 7/1998 | Torchilin |
| 5,883,223 A | 3/1999 | Gray |
| 6,004,534 A | 12/1999 | Langer |
| 7,189,396 B1 | 3/2007 | Weisbart |
| 9,107,950 B2 | 8/2015 | Borden |
| 9,283,272 B2 | 3/2016 | Weisbart |
| 9,701,740 B2 | 7/2017 | Hansen |
| 10,238,742 B2 | 3/2019 | Hansen |
| 10,683,363 B2 | 6/2020 | Weisbart |
| 2002/0090608 A1 | 7/2002 | Palese |
| 2003/0083305 A1 | 5/2003 | Palese |
| 2003/0109475 A1 | 6/2003 | Debs |
| 2004/0033235 A1 | 2/2004 | Bolognesi |
| 2004/0052820 A1 | 3/2004 | Bolognesi |
| 2005/0003343 A1 | 1/2005 | Palese |
| 2005/0221400 A1 | 10/2005 | Gudas |
| 2005/0256073 A1 | 11/2005 | Lipford |
| 2006/0110740 A1 | 5/2006 | Hurwitz |
| 2006/0127386 A1 | 6/2006 | Muzykantov |
| 2006/0216701 A1 | 9/2006 | Palese |
| 2006/0263367 A1 | 11/2006 | Fey |
| 2007/0166281 A1 | 7/2007 | Kosak |
| 2008/0004561 A1 | 1/2008 | Genkin |
| 2008/0085241 A1 | 4/2008 | Stassar |
| 2008/0292618 A1 | 11/2008 | Weisbart |
| 2009/0028901 A1 | 1/2009 | Palese |
| 2009/0186337 A1 | 7/2009 | Eleouet |
| 2009/0186802 A1 | 7/2009 | Bertrand |

(Continued)

FOREIGN PATENT DOCUMENTS

| | | |
|---|---|---|
| EP | 0437092 | 7/1991 |
| EP | 1666055 | 6/2006 |

(Continued)

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*

(Continued)

*Primary Examiner* — Brad Duffy
*Assistant Examiner* — Cheom-Gil Cheong
(74) *Attorney, Agent, or Firm* — Pabst Patent Group LLP

(57) ABSTRACT

DNA-targeted nanocarriers for encapsulating an active agent and delivering it to extracellular DNA are provided. The nanocarriers, for example, polymeric particles, liposomes, and multilamellar vesicles have targeting moiety that targets DNA conjugated thereto. The targeting moiety that targets DNA is typically an antibody, or variant, fragment, or fusion protein derived therefrom that binds to DNA or nucleosomes. The targeting moiety can be a circulating autoantibody that binds DNA such as those commonly found in patients with SLE. In some embodiments, the targeting moiety is antibody 3E10 or a variant, fragment, or fusion protein derived therefrom. Pharmaceutical compositions, methods of use, and dosage regimens are also provided.

13 Claims, 6 Drawing Sheets

Specification includes a Sequence Listing.

(56) References Cited

U.S. PATENT DOCUMENTS

| | | |
|---|---|---|
| 2010/0022680 A1 | 1/2010 | Karnik |
| 2010/0143358 A1 | 6/2010 | Weisbart |
| 2010/0196993 A1 | 8/2010 | Nishimura |
| 2010/0311171 A1 | 12/2010 | Nakanishi |
| 2011/0300164 A1 | 12/2011 | Lipford |
| 2012/0010124 A9 | 1/2012 | Bertrand |
| 2012/0214240 A1 | 8/2012 | Nakashini |
| 2013/0137644 A1 | 5/2013 | Bertrand |
| 2013/0266570 A1 | 10/2013 | Wesibart |
| 2014/0050723 A1 | 2/2014 | Hansen |
| 2014/0178377 A1 | 6/2014 | Armstrong |
| 2014/0234309 A1 | 8/2014 | Nishimura |
| 2015/0064181 A1 | 3/2015 | Armstrong |
| 2015/0376279 A1 | 12/2015 | Hansen |
| 2016/0114058 A1 | 4/2016 | Weisbart |
| 2016/0235859 A1 | 8/2016 | Weisbart |
| 2017/0073429 A1 | 3/2017 | Hansen |
| 2017/0130216 A1 | 5/2017 | Armstrong |
| 2017/0292961 A1 | 10/2017 | Hansen |
| 2017/0334981 A1 | 11/2017 | Hansen |
| 2019/0247515 A1 | 8/2019 | Zhou |
| 2019/0330317 A1* | 10/2019 | Hansen ............. A61K 47/6937 |
| 2020/0038520 A1 | 2/2020 | Weisbart |
| 2020/0129636 A1 | 4/2020 | Weisbart |
| 2020/0199255 A1 | 6/2020 | Hansen |
| 2020/0216567 A1 | 7/2020 | Campbell |
| 2020/0216568 A1 | 7/2020 | Campbell |

FOREIGN PATENT DOCUMENTS

| | | |
|---|---|---|
| EP | 3173428 | 5/2017 |
| EP | 3773919 | 2/2021 |
| WO | 9732602 | 9/1997 |
| WO | 1997032602 | 9/1997 |
| WO | 2004/003019 | 4/2006 |
| WO | 2004003019 | 4/2006 |
| WO | 2008/091911 | 7/2008 |
| WO | 2008091911 | 7/2008 |
| WO | 2008148063 | 12/2008 |
| WO | 2009/043031 | 4/2009 |
| WO | 2009043031 | 4/2009 |
| WO | 2009/134027 | 11/2009 |
| WO | 2009/142326 | 11/2009 |
| WO | 2009134027 | 11/2009 |
| WO | 2009142326 | 11/2009 |
| WO | 2010/013836 | 2/2010 |
| WO | 2010013836 | 2/2010 |
| WO | 2010056043 | 5/2010 |
| WO | 2010/148010 | 12/2010 |
| WO | 2010138769 | 12/2010 |
| WO | 2010148010 | 12/2010 |
| WO | 2012/135831 | 10/2012 |
| WO | 2012/145125 | 10/2012 |
| WO | 2012135831 | 10/2012 |
| WO | 2012145125 | 10/2012 |
| WO | 2013/031718 | 3/2013 |
| WO | 2013031718 | 3/2013 |
| WO | 2013/096835 | 6/2013 |
| WO | 2013096835 | 6/2013 |
| WO | 2013/138662 | 9/2013 |
| WO | 2013138662 | 9/2013 |
| WO | 2013/166487 | 11/2013 |
| WO | 2013/177428 | 11/2013 |
| WO | 2013166487 | 11/2013 |
| WO | 2013177428 | 11/2013 |
| WO | 2014087023 | 6/2014 |
| WO | 2014/130722 | 8/2014 |
| WO | 2014/130723 | 8/2014 |
| WO | 2014130722 | 8/2014 |
| WO | 2014130723 | 8/2014 |
| WO | 2015/106290 | 7/2015 |
| WO | 2015106290 | 7/2015 |
| WO | 2015/134607 | 9/2015 |
| WO | 2015134607 | 9/2015 |
| WO | 2015/192092 | 12/2015 |
| WO | 2015192092 | 12/2015 |
| WO | 2016013870 | 1/2016 |
| WO | 2016/033321 | 3/2016 |
| WO | 2016/033324 | 3/2016 |
| WO | 2016033321 | 3/2016 |
| WO | 2016033324 | 3/2016 |
| WO | 2017/218824 | 12/2017 |
| WO | 2017/218825 | 12/2017 |
| WO | 2017218824 | 12/2017 |
| WO | 2017218825 | 12/2017 |
| WO | 2018/049237 | 3/2018 |
| WO | 2018049237 | 3/2018 |
| WO | 2019018426 | 1/2019 |
| WO | 2019018428 | 1/2019 |
| WO | 2019152806 | 8/2019 |
| WO | 2019152808 | 8/2019 |
| WO | 2019/178532 | 9/2019 |
| WO | 2019178532 | 9/2019 |
| WO | 2019186141 | 10/2019 |
| WO | 2020047344 | 3/2020 |
| WO | 2020047345 | 3/2020 |
| WO | 2020047353 | 3/2020 |

OTHER PUBLICATIONS

Ward et al., Nature, 1989, 341:544-546. (Year: 1989).*
Bertram et al., Acta Biomaterialia 5 (2009) 2860-2871. (Year: 2009).*
Wen et al, Cancer Res; 73(14) Jul. 15, 2013. (Year: 2013).*
Caster et al, Nanoscale, Jul. 2015, 2805. (Year: 2015).*
Roby et al, Eur J Pharm Biopharm, 2006, 62(3): 235-240. (Year: 2006).*
Li et al, Journal of Clinical Laboratory Analysis (2003) 17:103-107. (Year: 2003).*
Aboul-Fadl, "Antisense oligonucleotides: the state of the art", Curr Med Chem., 12:2193-214 (2005).
Achuthan, et al., "Drug-induced senescence generates chemoresistant stemlike cells with low reactive oxygen species", J. Biol. Chem., 286:37813-29 (2011).
Adjei, "Blocking oncogenic Ras signaling for cancer therapy", J Natl Cancer Inst., 93 (14): 1062-74 (2001).
Aguilera, et al., "Systemic in vivo distribution of activatable cell penetrating peptides is superior to that of cell penetrating peptides", Integr Biol (Camb), 1(5-6): 371-81 (2009).
Ahmed, et al., "Extracellular renal guanosine cyclic 3'5'-monophosphate modulates nitric oxide and pressure-induced natriuresis", Hypertension, 50:958-63 (2007).
Alarcon-Segovia, "Antinuclear antibodies: to penetrate or not to penetrate, that was the question", Lupus, 10:315-8 (2001).
Allesen-Holm, et al., "A characterization of DNA release in Pseudomonas aeruginosa cultures and biofilms", Mol Biol., 59:1114-28 (2006).
American Cancer Society, Cancer Facts & Figures, pp. 1-70 (2014).
Andersen, et al.,"Identification of heme oxygenase-1-specific regulatory CD8+ T cells in cancer patients," Journal of Investigative Medicine, (2009).
Apte, et al., "Doxorubicin in TAT peptide-modified multifunctional immunoliposomes demonstrates increased activity against both drug-sensitive and drug-resistant ovarian cancer models", Cancer Biology & Therapy, 15(1):69-80 (2013).
Arnaudeau, et al., "DNA double-strand breaks associated with replication forks are predominantly repaired by homologous recombination involving an exchange mechanism in mammalian cells", J. Mol. Biol., 307:1235-45 (2001).
ATCC® CCl-86™ Raji, "Homo sapiens lymphoblast Burkitt's lymph", http://www.aroc.org/Products/ALL/CCL-86.aspx?&p=1 &rel=characteristics, 1 page, retrieved from the internet Jul. 10, 2015.
ATCC® CRL-1651™ COS-7 , "Cercopithecus aethiops kidney", http://www.aroc.org/Products/ALL/CRL1651.aspx 1 page, retrieved from the internet Jul. 12, 2015.
Barenholz, et al., "Doxil®—the first FDA-approved nano-drug: lessons learned", J Control Release, 160(2):117-34 (2012).

(56) References Cited

OTHER PUBLICATIONS

Barka, et al., "Transduction of TAT-HA—galactosidase Fusion Protein into Salivary Gland-derived Cells and Organ Cultures of the Developing Gland, and into Rat Submandibular Gland in Vivo", *Histochem. Cytochem.*, 48(11):1453-60 (2000).
Barnes, "Sativex: clinical efficacy and tolerability in the treatment of symptoms of multiple sclerosis and neuropathic pain", *Expert Opin. Pharmacother.*, 7:607-15 (2006).
Bassi, et al., "Nuclear PTEN controls DNA repair and sensitivity to genotoxic stress", *Science*, 341:395-9 (2013).
Berglund, et al., "The epitope space of the human proteome", *Protein Sci.*, 17:606-13 (2008).
Bernatsky, et al., Breast, ovarian, and endometrial malignancies in systemic lupus erythematosus: a meta-analysis *Br. J. Cancer* 104:1478-81(2011a).
Bernatsky, et al., "Cancer risk in systemic lupus: an updated international multi-centre cohort study", *J. Autoimmun.*, 42:130-5 (2013).
Bernatsky, et al., "Decreased breast cancer risk in systemic lupus erythematosus: the search for a genetic basis continues", *Lupus*, 21:896-9 (2008b).
Bernatsky, et al., "Prostate cancer in systemic lupus erythematosus", *Int. J. Cancer*, 129: 2966-9 (2011b).
Bernatsky, et al., "The relationship between cancer and medication exposures in systemic lupus erythaematosus: a case-cohort study", *Ann. Rheum. Dis.*, 67:74-9 (2008).
Bindra, et al., "Down-regulation of Rad51 and decreased homologous recombination in hypoxic cancer cells", *Mol. Cell. Biol.*, 24(19):8504-18 (2004).
Bisazza, et al., "Microbubble-Mediated Oxygen Delivey to Hypoxic Tissues as a New Therapeutic Device", *Engineering in Medicine and Biology Society*, 30th Annual International Conference of the IEEE (Aug. 20-24, 2008).
Bitzer, et al., "Sendai virus vectors as an emerging negative-strand RNA viral vector system", *J Gene Med.*, 5(7):543-53 (2003).
Brorson, et al., "Mutational analysis of avidity and fine specificity of anti-levan antibodies", *J Immunol.*, 163:6694-701 (1999).
Brummel, et al., "Probing the combining site of an anti-carbohydrate antibody by saturation-mutagenesis: role of the heavy-chain CDR3 residues", *Biochem.*, 32(4):1180-7 (1993).
Bryant, et al., "Specific killing of BRCA2-deficient tumours with inhibitors of poly(ADP-ribose) polymerase", *Nature*, 434:913-7 (2005).
Burks, et al., "In vitro scanning saturation mutagenesis of an antibody binding product", *PNAS*, 94:412-7 (1997).
Casset, et al., "Peptide mimetic of an anti-CD4 monoclonal antibody by rational design", *BBRC*, 307:198-205 (2003).
Celldex, CDX-011 Clinical program http://www.celldextherapeutics.com/wt/page/cds_011_breast?CMP=KNC-3GS620403736., retrieved from the interned Mar. 31, 2011.
Chan, et al., "Targeting cancer with a cell-penetrating anti-DNA antibody", *J. Investigative Med.*, 60(1):148 (2012).
Chauhan, et al., "Strategies for advancing cancer nanomedicine", *Nat. Mater.*, 12(11):958-62 (2013).
Chen, et al., "A lupus anti-DNA autoantibody mediates autocatalytic, targeted delivery of nanoparticles to tumors", *Oncotarget*, 7(37): 59965-59975 (2016).
Chen, et al., "Selection and analysis of an optimized anti-VEGF antibody: Crystal structure of an affinity-matured Fab in complex with antigen", *J. Mol. Biol.*, 283:865-81 (1999).
Chi, et al., "Roles of ATP binding and ATP hydrolysis in human Rad51 recombinase function", *DNA Repair (Amst)*, 5:381-91 (2006).
Chothia et al., "Canonical structures for the hypervariable regions of immunoglobulins", *J. Mol. Biol.*, 196:901-17 (1987).
Chow et al., "Cancer nanomedicine: from drug delivery to imaging", *Sci. Transl. Med.*, 5(216):216rv214 (2013).
Cleaver, et al., "Phosphorylated H2Ax is not an unambiguous marker for DNSA double-strand breaks", *Cell Cycle*, 10:3223-4 (2011).

Coffin, "HIV population dynamics in vivo: implications for genetic variation, pathogenesis, and therapy", *Science*, 267:483-9 (1995).
Colburn et al., "Serum antibodies as a marker for SLE disease activity and pathogen potential", *Clin. Chin. Acta.*, 370:9-16 (2006).
Colburn, et al., "Anti-guanosine antibodies in murine and human lupus have the internal image of G-binding proteins", *J. Rheumatol.*, 30(5):993-7 (2003).
Colburn, et al., "Circulating antibodies to guanosine in systemic lupus erythematosus: correlation with nephritis and polyserositis by acute and longitudinal analyses", *Lupus*, 10:410-7 (2001).
Coleman, "Effects of amino acid sequence changes on antibody-antigen interactions", *Res. Immunol.*, 145:33-6 (1994).
Collingridge, et al., "Pentoxifylline improves the oxygenation and radiarion response of BA 1112 rat rhabdomyosarcomas and EMT6 mouse mammary carcinomas", *Int. J. Cancer.*, 90(5):256-64 (2000).
Collins, et al., "Viral vectors in cancer immunotherapy: which vector for which strategy", *Curr. Gene Ther.*, 8(2):66-78 (2008).
Corada, et al., "Monoclonal antibodies directed to different regions of vascular endothelial cadherin extracellular domain affect adhesion and clustering of the protein and modulate endothelial permeability", *Blood*, 97(6):1679-84 (2001).
Croy et al., "Polymeric micelles for drug delivery", *Curr. Pharm. Des.*, 12(36):4669-84 (2006).
Cuesta, et al., "Multivalent antibodies: when design surpasses evolution", *Trends in Biotechnol.*, 28(7):355-62 (2010).
Dausch, et al., "Comparative study of treatment of the dry eye syndrome due to disturbances of the tear film lipid layer with lipid-containing tear substitutes", *Klin. Monatsbl. Augenheilkd*, 223:974-83 (2006).
Dean, et al, "Current advances in the translation of cascular tissue engineering to the treatment of pediatric congenital heart disease", *Yale J. Biol. Med.*, 85:229-38 (2012).
Demers, et al., "Cancers predispose neutrophils to release extracellular DNA traps that contribute to cancer-associated thrombosis", *PNAS*, 109(32):13076-81 (2012).
DePascalis, et al., "Grafting of abbreviated complementarity-determining regions containing specificity-determining residues essential for ligand contact to engineer a less immunogenic humanized monoclonal antibody", *J. Immun.*, 169:3076-84 (2002).
Derossi, et al., "The third helix of the Antennapedia homeodomain translocates through biological membranes", *J. Biol. Chem.*, 269(14):10444-50 (1994).
Deutsch, et al., "Guanosine possesses specific modulatory effects on NMDA receptor-mediated neurotransmission in intact mice," *Eur. Neuropsychopharmacol*, 18:299-302 (2008).
Deyev, et al., "Multivalemcy: the hallmark of antibodies used for optimization of tumor targeting by design", *Bioesseays*, 30(9):904-18 (2008).
Dimri, et al., "A biomarker that identifies senescent human cells in culture and in aging skin in vivo", *PNAS*, 92(20):9363-7 (1995).
Dowdy, et al., "Cationic PTD/CPP-mediated macromolecular delivery: charging into the cell," *Expert Opin. Drug Deliv.*, 12:1627-36 (2015).
Dray, et al., "Molecular basis for enhancement of the meiotic DMC1 recombinase by RAD51 associated protein 1 (RAD51AP1)", *PNAS*, 108:3560-5 (2011).
Eivazova, et al., "Specificity and binding kinetics of murine lupus anti-DNA monoclonal antibodies implicate different stimuli for their production", *Immunology*, 101:371-7 (2000).
Elbayoumi, et al., "Antinucleosome antibody-modified liposomes and lipid-core micelles for tumor-targeted delivery of therapeutic and diagnostic agents," *Journal of Liposome Research*, 17:1, 1-14 (2007).
Farmer, et al., "Targeting the DNA repair defect in BRCA mutant cells as a therapeutic strategy", *Nature*, 434:917-21 (2005).
Feng, et al., "Rad52 inactivation is synthetically lethal with BRCA2 deficiency", *PNAS*, 108:686-91 (2011).
Fiorica, "The role of topotecan in the treatment of advanced cervical cancer", *Gynecol. Oncol.*, 90:S16-21 (2003).
Ford, "Lupus antibody tops cancer cells", *Sci. Trans. Med.*, 4(157):157-60 (2012).
Foroutan, et al., "Molecular cytogenetic analysis of chemoresistant non-Hodgkin's lymphoma patients with p53 abnormalities using

(56) References Cited

OTHER PUBLICATIONS fluorescence in situ hybridisation and comparative genomic hybridisation", *Arch. Iran. Med.*, 14(5):321-6 (2011).
Frankel and Pabo, "Cellular uptake of the tat protein from human immunodeficiency virus", *Cell*, 55(6):1189-93 (1988).
Fujita, et al., "Brain tumor tandem targeting using a combination of monoclonal antibodies attached to biopoly(beta-L-malic acid)," *Journal of Controlled Release*, 122(3):356-363 (2007).
Fusaki, et al., "Efficient induction of transgene-free human pluripotent stem cells using a vector based on Sendai virus, an RNA virus that does not integrate into the host genome", *Proc. Jpn. Acad. Ser.*, B85:348-362 (2009).
Genbank, Accession No. L16981.1, "Mouse Ig rearranged L-chain gene, partial cds", 1 page, accessed Nov. 30, 2009, updated Mar. 6, 2012, first appeared May 1, 1995.
Genbank, Accession No. AAA65681.1, "Immunoglobulin light chain, partial [*Mus musculus*]", 2 pages, First available May 2, 1995, accessed Mar. 28, 2016.
Genbank, Accession No. AAA65682.1, "This CDS feature is included to show the translation of the corresponding V_region. Presently translation qualifiers on V_regions features are illegal, partial [*Mus musculus*]", 1 page, First available May 2, 1995, accessed Jun. 21, 2016.
Genbank, Accession No. AAA65679.1, immunoglobulin heavy chain, partial [*Mus musculus*], 2 pages, accessed Nov. 30, 2009, updated Mar. 6, 2012, first appeared May 1, 1995.
Gregoriadis et al., "Entrapment of proteins in liposomes prevents allergic reactions in pre-immunised mice", *FEBS Lett.*, 45(1):71-4 (1974).
Gregoriadis et al., "Liposomes as carriers of enzymes or drugs: a new approach to the treatment of storage diseases", *Biochem. J.*, 124:58P (1971).
Gregoriadis, "Engineering liposomes for drug delivery: progress and problems", *Trends Biotechnol.*, 13:527-37 (1995).
Gregoriadis, "The carrier potential of liposomes in biology and medicine (second of two parts)", *N. Engl. J. Medm.*, 295:765-70 (1976).
Gregoriadis, et al., "Improving the therapeutic efficacy of peptides and proteins: a role for polysialic acids", *Int. J. Pharm.*, 300:125-30 (2005).
Grudzien-Nogalska, et al., "Phosphorothioate cap analogs stabilize mRNA and increase translational efficiency in mammalian cells", *RNA*, 13(10):1745-55 (2007).
Gruhne, et al., "Three Epstein-Barr virus latency proteins independently promote genomic instability by inducing DNA damage, inhibiting DNA repair and inactivating cell cycle checkpoints", *Oncogene*, 28:3997-4008 (2009).
Gu, et al., "Genetic determinants of autoimmune disease and coronary vasculitis in the MRL-lpr/lpr mouse model of systemic lupus erythematosus", *J. Immunol.*, 161:6999-7006 (1998).
Gysin, et al., "Therapeutic strategies for targeting ras proteins", *Genes Cancer*, 2(3):359-72 (2011).
Hacein-Bey-Abina, et al., "LMO-2associated clonal T cell proliferation in two patients after gene therapy for SCID-X1", *Science*, 302(5644):415-9 (2003).
Halazonetis, et al., "An oncogene-induced DNA damage model for cancer development", *Science*, 319(5868):1352-5 (2008).
Han, et al., "Increased Nanoparticle Delivery to Brain Tumors by Autocatalytic Priming for Improved Treatment and Imaging", *ACS Nano*, 10(4):4209-18 (2016).
Hansen, et al. "Antibody mediated transduction of therapeutic proteins into living cells", *Scientific World*, 5(9):782-8 (2005).
Hansen, et al., "Antibody-mediated Hsp70 protein therapy", *Brain Res.*, 1088(1):187-96 (2006).
Hansen, et al., "Antibody-mediated p53 protein therapy prevents liver metastasis in vivo", *Cancer Res.*, 57(4):1769-1774 (2007).
Hansen, et al., "Intranuclear protein transduction through a nucleoside salvage pathway", *J. Biol. Chem.*, 282(29):20790-20793 (2007b).
Hansen, et al., "Targeting cancer with a lupus autoantibody", *Sci. Trans. Med.*, 4:157ra142 (2012).

Harrington, et al., "VX-680, a ptent and selective small-molecule inhibitor of aurora kinases suppresses tumor growth in vivo", *Nat. Med.*, 10:262-7 (2004).
Hawes, et al., "Extracellular DNA: A Bridge to Cancer", *Cancer Res.*, 75(20):4260-4 (2015).
Hayflick, et al., "The limited in vitro lifetime of human diploid cell strains", *Exp. Cell Res.*, 37:614-36 (1965).
Ho, et al., "Synthetic protein transduction domains: enhanced transduction potential in vitro and in vivo", *Cancer Res.*, 61(2):474-7 (2001).
Hoeijmakers, "DNA damage, aging, and cancer", *N. Engl. J. Med.*, 361:1475-85 (2009).
Holm, et al., "Functional mapping and single chain construction of the anti-cytokeratin 8 monoclonal antibody TS1", *Mol. Immun.*, 44:1075-84 (2007).
Holtkemp, et al., "Modification of antigen-encoding RNA increases stability, translational efficacy, and T-cell stimulatory capacity of dendritic cells", *Blood*, 108(13):4009-17 (2006).
Hrkach, et al., "Preclinical development and clinical translation of a PSMA-targeted docetaxel nanoparticle with a differentiated pharmacological profile", *Sci. Transl. Med.*, 4(128):128ra139 (2012).
Hucl, et al., "A syngeneic variance library for functional annotation of human variation: application to BRCA2", *Cancer Res.*, 68:5023-30 (2008).
Immordino, et al, "Stealth liposomes: review of the basic science, rationale, and clinical applications, existing and potential", *Int. J. Nanomedicine*, 1(3):297-315 (2006).
Isenberg, et al., "Fifty years of anti-ds DNA antibodies: are we approaching journey's end", *Rheumatology*, 46 (7):1052-6 (2007).
Itoh, et al., "Diagnostic use of anti-modified nucleoside monoclonal antibody", *Tohoku J. Exp. Med.*, 168:329-31 (1992).
Jackson, et al., "Guanosine regulates adenosine levels in the kidney" *Physiol. Rep.*, 2(5). pii: e12028. doi: 10.14814/phy2.12028 (2014).
Jain, "Transport of molecules across tumor vasculature", *Cancer Metastasis Rev.*, 6(4):559-593 (1987).
Jain, et al., "Engineering antibodies for clinical applications", *Trends in Biotechno.l*, 25(7):307-16 (2007).
Jang, et al., "Drug delivery and transport to solid tumors", *Phar. Res.*, 20:1337-50 (2003).
Jang, et al., "The structural basis for DNA binding by an anti-DNA autoantibody", *Mol. Immun.*, 35:1207-17 (1998).
Jordan, et al., Mechanism of mitotic block and inhibition of cell proliferation by taxol at low concentrations, *PNAS*, 90:9552-6 (1993).
Kabat, et al., "Sequences of proteins of Immunological Interest", 5 Ed. *Public Health Service, National Institutes of Health*, Bethesda Md. (1991).
Kabouridis, "Biological applications of protein transduction technology", *Trends in Biotechnol.*, (11):498-503 (2003).
Kaelin, Jr., et al., "The concept of synthetic lethality in the context of anticancer therapy", *Nat. Rev. Cancer*, 5:689-98 (2005).
Kane, et al., "Methylation of the hMLH1 promoter correlates with lack of expression of hMLH1 in sporadic colon tumors and mismatch repair-defective human tumor cell lines", *Cancer Rev.*, 57:808-11 (1997).
Kay, "State of the art gene-based therapies: the road ahead", *Nature Rev. Genetics*, 12(5):316-28 (2011).
Kellner, et al., "Boosting ADCC and CDC activity by Fc engineering and evaluation of antibody effector functions", *Methods*, 65:105-13 (2014).
Kelly, et al., "Targeted liposomal drug delivery to monocytes and macrophages", *J. Drug Deliv.*, 2011(727241):1-11 (2011).
Kim, et al., "Heavy and light chain variable single domains of an anti-DNA binding antibody hydrolyze both double- and single-stranded DNAs without sequence specificity", *J. Biological Chem.*, 281(22):15287-95 (2006).
Kobayashi, et al., "Tryptophan H33 plays an important role in pyrimidine (6-4) pyrimidone photoproduct binding by a high-affinity antibody", *Protein Eng.*, 12(10):879-84 (1999).
Kocbek, et al., "Targeting cancer cells using PLGA nanoparticles surface modified with monoclonal antibody", *Journal of Controlled Release*, 120:1-2, 18-36 (2007).

(56) References Cited

OTHER PUBLICATIONS

Kozyr, et al., "Anti-DNA autoantibodies reveal toxicity to tumor cell lines", *Immunol. Lttr.*, 80:41-7 (2002).
Kulkarin-Kale, et al., "CEP: a conformational epitope prediction server", *Nucleic Acids Res.*, 33:W168-W171 (2005).
Kumar, et al., "Molecular cloning and expression of the fabs of human autoantibodies in *Escherichia coli*", *J. Bio. Chem.*, 275:35129-36 (2000).
Lallemand, et al., "Cyclosporine A delivery to the eye: a pharmaceutical challenge", *Eur. J. Pharm. Biopharm.*, 56:307-18 (2003).
Lau, et al., "Suppression of HIV-1 infection by a small molecule inhibitor of the ATM kinase", *Nat Cell Biol*, 7(5): 493-500 (2005).
Lee, et al., "A new therapy concept with a Liposome Eye Spray for the treatment of dry eye", *Klin. Monatsbl. Augenheilkd.*, 221:825-36 (2004).
Lee, et al., "Cell-penetrating autoantibody induces caspase-mediated apoptosis through catalytic hydrolysis of DNA", *Bioorg. Med. Chem.*, 15(5):2016-23 (2007).
Lee, et al., "Gene silencing by cell-penetrating, sequence-selective and nucleic-acid hydrolyzing", *Nucleic Acid Res.*, pp. 1-14 (2009).
Lei, et al., "Targeted Delivery of Doxorubicin by PLGA Nanoparticles Increases Drug Uptake in Cancer Cell Lines", *26th Southern Biomedical Engineering Conference SBEC 2010*, Apr. 30-May 2, 2010, College Park, Maryland, USA, 32:224-227 (2010).
Levitt, et al., "PTEN-induction in U251 glioma cells decreases the expression of insulin-like growth factor binding protein-2", *Biochem. Biophys. Res. Comm.*, 336:1056-61 (2005).
Lewitzky, et al., "Reprogramming somatic cells towards pluripotency by defined factors", *Curr. Opin. Biotechnol.*, 18:467-73 (2007).
Li, et al., "Homologous recombination in DNA repair and DNA damage tolerance", *Cell Res.*, 18:99-113 (2008).
Li, et al., "PTEN, a putative protein tyrosine phosphatase gene mutated in human brain, breast, and prostate cancer", *Science*, 275:1943-7 (1997).
Liao, et al., "The comet assay: a sensitive method for detecting DNA damage in individual cells", *Methods*, 48(1):46-53 (2009).
Lin, et al., "Improved affinity of a chicken single-chain antibody to avian infectious bronchitis virus by site-directed mutagenesis of complementarity-determining region H3", *African J. Biotech.*, 10(79):18294-18302 (2011).
Lisi, et al., "Advances in the understanding of the Fc gamma receptors-mediated autoantibodies uptake", *Clin. Exp. Med.*, 11:1-10 (2011).
Liu, et al., "A novel bivalent single-chain variable fragment (scFV) inhibits the action of tumor necrosis factor [alpha]", *Biotechnol. App. Biochem.*, 50(4):173-9 (2008).
Liu, et al., "Iniparib Nonselectively Modifies Cysteine-Containing Proteins in Tumor Cells and Is Not a Bona Fide PARP Inhibitor," *Clin. Cancer Res.*, 18:510-523 (2012).
Liu, et al., "Poly($\omega$-pentadecalactone-co-butylene-co-succinate) Nanoparticles as Biodegradable Carriers for Camptothecin Delivery", *Biomaterials*, 30:5707-19 (2009).
Ma, et al., "Antibodies to guanosine triphosphate misidentified as anti-double-stranded DNA antibodies in a patient with antinuclear antibody-negative lupus, due to buckling of insolubilized assay DNA", *Arthritis Rheum.*, 50:1533-1538 (2004).
MacCallum, et al., "Antibody-antigen interactions: Contact analysis and binding site topography", *J. Mol. Biol.*, 262:732-45 (1998).
Maeda, et al., "Tumor vascular permeability and the EPR effect in macromolecular therapeutics: a review", *J. Controlled Release*, 65:271-84 (2000).
Mariuzza, et al., "The structural basis of antigen-antibody recognition", *An. Res. Biophys. Biophys. Chem.*, 16:139-59 (1987).
McCabe, et al., "BRCA2-deficient CAPAN-1 cells are extremely sensitive to the inhibition of Poly (ADP-Ribose) polymerase: an issue of potency", *Cancer Biology Therapy*, 4:934-6 (2005).
McCarthy, et al., "Altering the fine specificity of an anti-legionella single chain antibody by a single amino acid insertion", *J. Immunol. Meth.*, 21:137-49 (2001).
McEllin, et al., "PTEN loss compromises homologous recombination repair in astrocytes: implications for glioblastoma therapy with temozolomide or poly(ADP-ribose) polymerase inhibitors", *Cancer Res.*, 70:5457-64 (2010).
Minko, et al., "New generation of liposomal drugs for cancer", *Anticancer Agents Med. Chem.*, 6:537-52 (2006).
Molfetta, et al., "Regulation of fc receptor endocytic trafficking by ubiquitination", *Front Immunol*, 5:449. Doi: 10.3389/fimmu.2014.00449 (2014).
Moynahan, et al., "BRCA2 is required for homology-directed repair of chromosomal breaks", *Mol. Cell*, 7:263-72 (2001).
Muller, et al., "TransMabs: cell-penetrating antibodies, the next generation", *Exp. Opin. Biol. Ther.*, 5(2):1-5 (2005).
Nakanishi, et al., "Development of sendai virus vectors and their potential applications in gene therapy and regenerative medicine", *Curr. Gene Ther.*, 12(5):410-6 (2012).
Noble, et al., "A cell-penetrating nucleoltyic lupus autoantibody damages DNA and is toxic to BRCA2-deficient cancer cells" poster presented at the Proceedings: AACR Annual Meeting; Apr. 5-9, 2014, San Diego, CA (2014b).
Noble, et al., "A cell-penetrating nucleolytic lupus autoantibody damages DNA and is toxic to BRCA2-deficient cancer cells", Abstract 4220, *Cancer Res.*, 74:4220 (2014c).
Noble, et al., "A nucleolytic lupus autoantibody is toxic to BRCA2-deficient cancer cells", *Sci. Rep-Uk.*, 4:5958. doi: 10.1038/srep05958 (2014).
Noble, et al., "DNA-damaging autoantibodies and cancer: the lupus butterfly theory", *Nat. Rev. Rheumatol.*, 12(7):429-34 (2016).
Noble, et al., "Optimizing a lupus autoantibody for targeted cancer therapy", *Cancer Res.*, 75(11):2285-91 (2015).
Okita, et al., "Induction of pluripotency by defined factors", *Exp. Cell Res.*, 316(16):2565-70 (2010).
Okshevsky, et al., "Extracellular DNA as a target for biofilm control", *Curr. Opin. Biotech.*, 33:73-80 (2015).
Padlan, "X-ray crystallography of anti-bodies", *Adv. Protein Chem.*, 49:57-133 (1996).
Park, et al., "PEGylated PLGA nanoparticles for the improved delivery of doxorubicin", *Nanomed-Nanotechnol.*, 5:410-8 (2009).
PARP Inhibitor, http://www.parp-inhibitors.com, retrieved from the internet Mar. 31, 2011.
Pavlovic, et al., "Pathogenic and epiphenomenal anti-DNA antibodies in SLE", *Autoimmune Diseases*, 2010:462841 1-18 (2010).
Porter, et al., "Chimeric antigen receptor-midified T cells in chronic lymphoid leukemia", *NEJM*, 365(8):725-33 (2011).
Puc, et al., "PTEN loss inhibits CHK1 to cause double stranded-DNA breaks in cells", *Cell Cycle*, 4:927-9 (2005).
Rabinovich, et al., "Chimeric receptor mRNA transfection as a tool to generate antineoplastic lymphocytes", *Human Gene Therapy*, 20(1):51-61 (2009).
Rabinovich, et al., "Synthetic messenger RNA as a tool for gene therapy", *Hum. Gene. Ther.*, 17(10):1027-35 (2006).
Rahman and Isenberg, "Systemic lupus erythematosus", *N. Engl. J. Med.* 358:929-39 (2008).
Rathbone, et al., "Neurotrophic effects of extracellular guanosine" *Nucleosides, Nucleotides Nucleic Acids*, 27:666-72 (2008).
Ratnam, et al., "Current development of clinical inhibitors of poly(ADP-ribose) polymerase in oncology", *Clin, Cancer Res.*, 13(5):1383-8 (2007).
Ritter, et al., "Gene therapy in transplantation: Toward clinical trials", *Curr. Opin. Mol. Ther.*, 11(5):504-12 (2009).
Rivadeneyra-Espinoza, et al., "Cell-penetrating anti-native DNA antibodies trigger apoptosis through both the neglect and programmed pathways", *J. Auto Immunity*, 26:52-6 (2006).
Rudikoff, et al., "Single amino substitution altering antigen-binding specificity", *PNAS*, 79:1979-83 (1982).
Sakai, et al., "Functional restoration of BRCA2 protein by secondary BRCA2 mutations in BRCA2-mutated ovarian carcinoma", *Cancer Res.*, 69:6381-6 (2009).
Sancar, et al., "Molecular mechanisms of mammalian NA repair and the DNA damage checkpoints", *Annu. Rev. Biochem.*, 73:39-85 (2004).

(56) References Cited

OTHER PUBLICATIONS

Sano, et al., "Dna isolated from DNA/anti-DNA antibody immune complexes in systemic lupus erythematosus is rich in guanine-cytosine content" *J. Immunol.*, 128:1341-1345 (1982).
Sapra, et al., "Ligand-targeted liposomes for cancer treatment", *Curr. Drug Deliv.*, 2:369-81 (2005).
Sawant, et al., "Nanosized cancer cell-targeted polymeric immunomicelles loaded with superparamagnetic iron oxide particles", *Journal of Nanoparticle Research*, 11(7):1777-1785 (2009).
Scott, et al., "Antibody therapy of cancer", *Nature Reviews Cancer*, 12:278-87 (2012).
Senge, "Immunoliposomes", *Curr. Med. Chem.*, 19(31):5239-77 (2012).
Service, et al., "Nanotechnology. Nanoparticle Trojan horses gallop from the lab into the clinic", *Science*, 330(6002):314-315 (2010).
Shao, et al., "Reversibly crosslinked nanocarriers for on-demand drug delivery in cancer treatment", *Ther, Deliv,*, 3(12):1409-27 (2012).
Shin, et al., "Pharmacokinetics of guanosine in rats following intravenous or intramuscular administration of a 1:1 mixture of guanosine and acriflavine, a potential antitumor agent", *Arch. Pharm. Res.*, 31(10):1347-53 (2008).
Shuster, et. al., "DNA hydrolyzing autoantibodies", *Science*, 56(5057):665-7 (1992).
Singh, et al., "A gene expression signature associated with "K-Ras addiction" reveals regulators of EMT and tumor cell survival", *Cancer Cell*, 15:489-500 (2009).
Skoulidis, et al., "Germline Brca2 heterozygosity promotes Kras(G12D)—driven carcinogenesis in a murine model of familial pancreatic cancer", *Cancer Cell*, 18:499-509 (2010).
Sliwinska, et al., "Induction of senescence with doxorubicin leads to increased genomic instability of HCT116 cells", *Mech. Ageing Dev.*, 130:24-32 (2009).
Smith-Gill, et al., "Contributions of immunoglobulin heavy and light chains to antibody specificity for lysozyme and two haptens", *J Immunol.*, 139:4135-44 (1987).
Song, et al., "Light chain of natural antibody plays a dominant role in protein antigen binding", *Biochem Biophys Res Comm.*, 268:390-4 (2000).
Spertini, et al., "Idiotypic vaccination with a murine anti-dsDNA antibody: phase I study in patients with nonactive systemic lupus erythematosus with nephritis", *J. Rheumatol.*, 269120:2602-8 (1999).
Stachelek, et al., "Potentiation of temozolomide cytotoxicity by inhibition of DNA polymerase beta is accentuated by BRCA2 mutation", *Cancer Res.*, 70:409-17 (2010).
Stanulis-Praeger, et al., "Cellular senescence revisited: a review", *Mech. Ageing Derv.*, 38:1-48 (1987).
Steck, et al., "Identification of a candidate tumour suppressor gene, MMAC1, at chromosome 10q23.3 that is mutated in multiple advanced cancers", *Nat Genet.*, 15:356-62 (1997).
Stepinski, et al., "Synthesis and properties of mRNA's containing the novel "anti-reverse" cap analogs 7-methyl(3'-O-methyl)GpppG and 7-methyl (3'-deoxy)GpppG", *RNA*, 7(10:1486-95 (2001).
Stollar, et al., "Nucleoside specificity in the carrier IgG-dependent induction of tolerance", *J. Immunol.*, 117:1308-1313 (1976).
Stone, et al., "Neoadjuvant chemotheraoy and liver transplantation for hepatocellular carcinoma: a pilot study in 20 patients", *Gastroenterology*, 104(1):196-202 (1993) Abstract Only.
Stroun, et al., "About the possible origin and mechanism of circulating DNA apoptosis and active DNA release", *Clin. Chim. Acta.*, 313(1-2):139-142 (2001).
Sueoka-Aragane, et al., "Correlation between plasma DNA and tumor status in an animal model", *PloS One*, 9(12) (2014).
Sugahara, et al, "Tissue-penetrating delivery of compounds and nanoparticles into tumors", *Cancer Cell*, 16(6):510-20 (2009).
Sung, "Catalysis of ATP-dependent homologous DNA pairing and strand exchange by yeast RAD51 protein", *Science*, 265:1241-3 (1994).
Sung, et al., "DNA strand exchange mediated by a RAD51-ssDNA nucleoprotein filament with polarity opposite to that of RecA", *Cell*, 82:453-61 (1995).
Sung, et al., "Rad51 recombinase and recombination mediators", *J. Biol. Chem.*, 278:42729-32 (2003).
Swystun, et al., "Breast cancer chemotherapy induces the release of cell-free DNA, a novel procoagulant stimulus", *J. Thromb. Haemost.*, 9(11):2313-2321 (2011).
Te Poele, et al., "DNA damage is able to induce senescence in tumor cells in vitro and in vivo", *Cancer Res.*, 62:1876-1883 (2002).
Tewey, et al., "Adriamycin-induced DNA damage mediated by mammalian DNA topoisomerase II", *Science*, 226:466-8 (1984).
Tyagi, et al., "Urodynamic and immunohistochemical evaluation of intravesical capsaicin delivery using thermosensitive hydrogel and liposomes", *J Urol*, 171:483-9 (2004).
Tzartos, et al., "Epitope mapping by antibody completion", *Methods Molecular Biol.*, 66:55-66 (1996).
Uemura, et al., "Neurochemical analysis of focal ischemia in rats", *Stroke*, 22:1548-53 (1991).
Vajdos, et al., "Comprehensive functional maps of the antigen-binding site of am amti-ErbB2 antibody obtained with shotgun scanning mutagenesis", *J. Mol. Biol.*, 320:415-28 (2002).
Vlietstra, et al., "Frequent inactivation of PTEN in prostate cancer cell lines and xenografts", *Cancer Res.*, 58:2720-3 (1998).
Von Maltzahn, et al., "Nanoparticles that communicate in vivo to amplify tumour targeting", *Nat Mater*, 10(7):545-52 (2011).
Wadia and Stan, "Transducible TAT-HA fusogenic peptide enhances escape of TAT-fusion proteins after lipid raft micropinocytosis", *Nat Med.*, 10(3):310-5 (2004).
Walpita, et al., "Reverse genetics of negative-stranded RNA viruses: a global perspective", *FEMS Microbiol. Lett.*, 244(1):9-18 (2005).
Wang, Mutagenesis in mammalian cells induced by triple helix formation and transcription-coupled repair, *Science*, 271(5250):802-5 (1996).
Ward, et al., "Binding activities of a repertoire of single immunoglobulin variable domains secreted from *Escherichia coli*", *Nature*, 341:544-6 (1989).
Warren, et al., "Highly efficient reprogramming to pluripotency and directed differentiation of human cells with synthetic modified mRNA", *Cell Stem Cell*, 7(5):618-30 (2010).
Weisbart, "Antibody-mediated transduction of p53 selectively kills cancer cells", *Int. J. Oncol.*, 25(6):1867-73 (2004).
Weisbart, et al. "A conserved anti-DNA antibody idiotype associated with nephritis in murine and human systemic lupus erythematosus", *J. Immunol.*, 144(7): 2653-8 (1990).
Weisbart, et al. "Novel protein transfection of primary rat cortical neurons using an antibody that penetrates living cells", *J. Immunol.*, 164:6020-6026 (2000).
Weisbart, et al., "A cell-penetrating bispecific antibody for therapeutic regulation of intracellular targets", *Mol. Cancer Ther.*, 11(10):2169-73 (2012).
Weisbart, et al., "An autoantibody is modified for use as a delivery system to target the cell nucleus: therapeutic implications", *J. Autoimmun.*, 11:539-46 (1998).
Weisbart, et al., "Cell type specific targeted intracellular delivery into muscle of a monoclonal antibody that binds myosin IIb", *Mol. Immunol.*, 39(13):783-9 (2003).
Weisbart, et al., "Construction and expression of a bispecific single-chain antibody that penetrates mutant p53 colon cancer cells and binds p53", *Int. J. Oncology*, 25:1113-8 (2004).
Weisbart, et al., "DNA-dependent targeting of cell nuclei by a lupus autoantibody", *Sci. Rep.*, 5:12022 (2015).
Weisbart, et al., "Nuclear delivery of p53 C-terminal peptides into cancer cells using scFv fragments of a monoclonal antibody that penetrates living cells", *Cancer Lttrs.*, 195:211-19 (2003).
Wen, et al., "Extracellular DNA in pancreatic cancer promotes cell invasion and metastasis", *Cancer Res*, 73(14):4256-66 (2013).
Wender, et al., "The design, synthesis, and evaluation of molecules that enable or enhance cellular uptake: peptoid molecular transporters", *PNAS*, 97(24):13003-8 (2000).
Whitchurch, et al., "Extracellular DNA required for bacterial biofilm formation", *Science*, 295(5559):1487 (2002).

(56) References Cited

OTHER PUBLICATIONS

Whitney, et al., "Parallel in vivo and in vitro selection using phage display identifies protease-dependent tumor-targeting peptides", *J. Biol. Chem.*, 285(29):22532-41 (2010).
Williams, "DNA hydrolysis mechanism and reactivity", *Nucleic Acids and Molecular Biology*, 13:1-7, (2004).
Wu, et al., "Humanization of a murine monoclonal antibody by simultaneous optimization of framework and CDR residues", *J Mol Biol.*, 294:151-62 (1999).
Wu, et al., "pH-sensitive poly(histidine)-PEG/DSPE-PEG co-polymer micelles for cytosolic drug delivery", *Biomaterials*, 34:4, 1213-1222 (2013).
Xu, et al., "Dual DNA unwinding activities of the Rothmund-Thomson syndrome protein, RECQ4", *EMBO J.*, 28:568-77 (2009b).
Xu, et al., "MCM10 mediates RECQ4 association with MCM2-7 helicase complex during DNA replication", *EMBO J.*, 28:3005-14 (2009a).
Yee, et al., "The fine specificity of IgG antiguanosine antibodies in systemic lupus erythematosus", *Clin Immunol. Immunopathol.*, 36(2):161-7 (1985).
Yeh, et al, "A Targeting Microbubble for Ultrasound Molecular Imaging," *PLoS One*, 10(7): e0129681. doi:10.1371/ journal.pone. 0129681 (2015).
Yoder, et al., "The base excision repair pathway is required for efficient lentivirus integration", *PLoS One*, 6(3) e17862 (2011).
Yoshizaki, et al., "Naked sendai virus vector lacking all of the envelope-related genes: reduced cytopathogenicity and immunogenicity", *J Gene Med.*, 8(9):1151-9 (2006).
Young, et al., "Targeting K-ras cancer cells with a lupus anti-guanosine antibody", *Cancer Res.*, 74(19 Supp):654 (2014). Abstract Only.
Yung, et al., "Anti-DNA antibodies in the pathogenesis of lupus nephritis—The emerging mechanisms", *Autoimmunity Rev.*, 7(4):317-21 (2008).
Zack, et al. "Mechanisms of cellular penetration and nuclear localization of an anti-double strand DNA autoantibody", *J. Immunol.* 157(5):2082-8 (1996).
Zack, et al., "DNA mimics a self-protein that may be a target for some anti-DNA antibodies in systemic lupus erythematosus", *J. Immunol.* 154:1987-94 (1995b).
Zack, et al., "Novel structural features of autoantibodies in murine lupus: a possible superantigen binding site", *Immunol. Cell Biol.*, 72:513-20 (1994).
Zack, et al., "Two kappa immunoglobulin light chains are secreted by an anti-DNA hybridoma: implications for isotypic exclusion" *Mol. Immunol.*, 32:1345-53 (1995).
Zhan, et al., "Recombinant Fv-Hsp70 protein mediates neuroprotection after focal cerebral ischemia in rats", *Stroke*, 41(3):538-43 (2010).
Zhou, et al., "Highly penetrative, drug-loaded nanocarriers improve treatment of glioblastoma", *PNAS*, 110:11751-6 (2013).
Zhou, et al., "Octa-functional PLGA nanoparticles for targeted and efficient siRNA delivery to tumors", *Biomaterials*, 33(2):583-91 (2012).
Zhu, et al., "Matrix Metalloprotease 2-Rsponsive Multifunctional Liposomal Nanocarrier for Enhanced Tumor Targeting", *ACS Nano*, 6(4): 3491-3498 (2012).
International Search report for corresponding PCT application PCT/US2017/037754 dated Aug. 24, 2017.
Colburn et al., "Serum antibodies as a marker for SLE disease activity and pathogen potential", Clin Chim Acta, 370:9-16 (2006).
Genbank, Accession No. AAA65682.1, "This CDS feature is included to show the translation of the of the corresponding V_region. Presently translation qualifiers on V_regions features are illegal, partial [*Mus musculus*]", 1 page, First available May 2, 1995, accessed Jun. 21, 2016.
Mariuzza, et al., "The structural basis of antigen-antibody recognition", Am Res Biophys Biophys Chem., 16:139-59 (1987).

Noble, et al., "A nucleolytic lupus autoantibody is toxic to BRCA2-deficient cancer cells", Sci Rep-Uk, 4:5958. doi: 10.1038/srep05958 (2014a).
Pavlovic, et al., "Pathogenic and epiphenomenal anti-DNA antibodies in SLE", Autoimmime Diseases, 2010:462841 1-18 (2010).
Shuster, et al., "DNA hydrolyzing autoantibodies", Science, 256(5057):665-7 (1992).
Weisbart, "Antibody-mediated transduction of p53 selectively kills cancer cells", Int. J. Oncol., 25(6):1867-73 (2004a).
Weisbart, et al., "Cell type specific targeted intracellular delivery into muscle of a monoclonal antibody that binds myosin IIb", Mol Immunol, 39(13):783-9 (2003a).
Weisbart, et al., "Construction and expression of a bispecific single-chain antibody that penetrates mutant p53 colon cancer cells and binds p53", Int J Oncology, 25:1113-8 (2004b).
Weisbart, et al., "Novel protein transfection of primary rat cortical neurons using an antibody that penetrates living cells", J Immunol., 164: 6020-6 (2000).
Weisbart, et al., "Nuclear delivery of p53 C-terminal peptides into cancer cells using scFv fragments of a monoclonal antibody that penetrates living cells", Cancer Lttrs., 195:211-19 (2003b).
Zack, et al., "DNA mimics a self-protein that may be a target for some anti-DNA antibodies in systemic lupus erythematosus", J. Immunol. 154:1987-94 (1995a).
Zack, et al., "Two kappa immunoglobulin light chains are secreted by an anti-DNA hybridoma: implications for isotypic exclusion" Mol Immunol, 32:1345-53 (1995b).
Bao, et al., "PLGA-PLL-PEG-Tf-based targeted nanoparticles drug delivery system enhance antitumor efficacy via intrinsic apoptosis pathway", International Journal of Nanomedicine, 10: 557-66 (2015).
U.S. Appl. No. 16/967,109, Aug. 3, 2020, Hansen.
U.S. Appl. No. 16/967,110, Aug. 3, 2020, Hansen.
Jang, et al., "A nucleic acid-hydrolyzing antibody penetrates into cells via caveolae-mediated endocytosis, localizes in the cytosol and exhibits cytotoxicity", Cell Mol. Life Sci., 66:1985-97 (2009).
Okudaira, et al.,"Monoclonal murine anti-DNA antibody interacts with living mononuclear cells", Arthritis Rheum. 30, 669-678 (1987).
Rattray et al., "Re-Engineering and Evaluation of Anti-DNA Autoantibody 3E10 for Therapeutic Applications", Biochem Biophys Res Common., 496:858-864 (2018).
Rhodes and Isenberg, "Function and therapeutic potential of intracellular antibodies", Trends Immunol 38, 916-926 (2017).
Ruiz-Arguelles, et al., "Penetration of anti-DNA antibodies into immature live cells." J. Autoimmun., 11(5):547-56 (1998).
Silosi, et al., "The role of autoantibodies in health and disease", Rom J Morphol Embryol, 57(2 Suppl):633-638 (2016).
Song, et al., "Arginines in the CDR of anti-dsDNA autoantibodies facilitate cell internalization via electrostatic interactions", Eur. J. Immunol., 38(11):3178-90 (2008).
Turchick, et al., "A cell-penetrating antibody inhibits human RAD51 via direct binding", Nucleic Acids Research, 45(20):11782-11799 (2017).
Vlahakos, et al., "Murine Monoclonal Anti-Dna Antibodies Penetrate Cells, Bind To Nuclei, And Induce Glomerular Proliferation And Proteinuria In Vivo." J. Am. Soc. Nephrol. 2(8):1345-54 (1992).
Weidle, et al., "The Translational Potential for Target Validation and Therapy Using Intracellular Antibodies in Oncology", Cancer Genomics Proteomics, 10: 239-250 (2013).
Weisbart R H, et al., "An intracellular delivery vehicle for protein transduction of micro-dystrophin", J. Drug Target., 13(2):81-7 (2005).
Weisenthal, Human Tumor Assay Journal, on-line at http://weisenthal.org/synergy1.htm, (Mar. 14, 2012).
Wolf, et al., "RPA and Rad51 constitute a cell intrinsic mechanism to protect the cytosol from self DNA", Nat. Common., 7:11752 (2016).
Yanase, et al., "Receptor-mediated Cellular Entry of Nuclear Localizing Anti-DNA Antibodies via Myosin 1", J. Clin. Invest., 100:25-31 (1997).
Alarcon-Segovia, et al., "Antibody penetration into living cells. I. Intranuclear immunoglobulin in peripheral blood mononuclear cells

(56) References Cited

OTHER PUBLICATIONS in mixed connective tissue disease and systemic lupus erythematosus", Clin. Exp. Immunol., 35:364-375 (1979).

Allemann, et al., "Drug-loaded nanoparticles: Preparation methods and drug targeting issues", European Journal of Pharmaceuticals and Biopharmaceuticals, 39(5):173-191 (1993).

Avrameas, et al., "Polyreactive anti-DNA monoclonal antibodies and a derived peptide as vectors for the intracytoplasmic and intranuclear translocation of macromolecules" Proc. Natl. Acad. Sci. U.S.A., 95(10):5601-5606 (1998).

Axup, "Synthesis of site-specific antibody-drug conjugates using unnatural amino acids", Proceedings of the National Academy of Sciences, 109 (40): 16101-6 (2012).

Chan, et al., "Combining intracellular antibodies to restore function of mutated p53 in cancer" Int. J. Cancer, 138(1):182-6 (2016).

Deng et al., "In vivo cell penetration and intracellular transport of anti-Sm and anti-La autoantibodies", Int Immunol 12, 415-423 (2000).

eGenBank: L34051.1—Mouse Ig rearranged kappa-chain mRNA V-region. (May 1, 1995).

GenBank Acc. No. BAG36664.1, unnamed protein product [*Homo sapiens*]. (Jan. 11, 2008).

Genbank AF289183.1., Mus musculus anti-DNA monoclonal autoantibody G1-5 light chain variable region mRNA, partial cds. (Jul. 25, 2000).

Golan et al., "Penetration of Autoantibodies into Living Epithelial Cells", J Invest Dermatol 100, 316-322 (1993).

Huang, et al., "Complications mimicking lupus flare-up in a uremic patient undergoing pegylated liposomal doxorubicin therapy for cervical cancer", Anti-Cancer Drugs, 15:239-241 (2004).

Im et al., "Cell- and nuclear-penetrating anti-dsDNA autoantibodies have multiple arginines in CDR3 of VH and increase cellular level of pERK and Bcl-2 in mesangial cells", Mol Immunol 67, 377-387 (2015).

Im et al., "Development of single-chain Fv of antibody to DNA as intracellular delivery vehicle", Animal Cells and Systems 21, 382-387 (2017).

Isenberg, et al., "Detection Of Cross-Reactive Anti-Dna Antibody Idiotypes In The Serum Of Systemic Lupus Erythematosus Patients And Of Their Relatives", Arthritis Rheum 28, 999-1007 (1985).

* cited by examiner

SEQUENCE LISTING

```
<160> NUMBER OF SEQ ID NOS: 30

<210> SEQ ID NO 1
<211> LENGTH: 116
<212> TYPE: PRT
<213> ORGANISM: Mus musculus

<400> SEQUENCE: 1

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
```

<223> OTHER INFORMATION: synthetic polypeptide

<400> SEQUENCE: 2

```
Glu Val Gln Leu Val Glu Ser Gly Gly Gly Leu Val Lys Pro Gly Gly
1               5                   10                  15
Ser Arg Lys Leu Ser Cys Ala Ala Ser Gly Phe Thr Phe Ser Asn Tyr
            20                  25                  30
Gly Met His Trp Val Arg Gln Ala Pro Glu Lys Gly Leu Glu Trp Val
        35                  40                  45
Ala Tyr Ile Ser Ser Gly Ser Ser Thr Ile Tyr Tyr Ala Asp Thr Val
    50                  55                  60
Lys Gly Arg Phe Thr Ile Ser Arg Asp Asn Ala Lys Asn Thr Leu Phe
65                  70                  75                  80
Leu Gln Met Thr Ser Leu Arg Ser Glu Asp Thr Ala Met Tyr Tyr Cys
                85                  90                  95
Ala Arg Arg Gly Leu Leu Leu Asp Tyr Trp Gly Gln Gly Thr Thr Leu
            100                 105                 110
Thr Val Ser Ser
        115
```

<210> SEQ ID NO 3
<211> LENGTH: 111
<212> TYPE: PRT
<213> ORGANISM: Mus musculus

<400> SEQUENCE: 3

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Lys Ser Val Ser Thr Ser
            20                  25                  30
Ser Tyr Ser Tyr Met His Trp Tyr Gln Gln Lys Pro Gly Gln Pro Pro
        35                  40                  45
Lys Leu Leu Ile Lys Tyr Ala Ser Tyr Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ser Arg
                85                  90                  95
Glu Phe Pro Trp Thr Phe Gly Gly Gly Thr Lys Leu Glu Ile Lys
            100                 105                 110
```

<210> SEQ ID NO 4
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 4

```
Gly Gln Ser Ser Arg Ser Ser
1               5
```

<210> SEQ ID NO 5
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 5

```
Gly Gln Ser Ser Arg Ser Ser Gly Gly Gly Ser Ser Gly Gly Gly
1               5                   10                  15

Gly Ser

<210> SEQ ID NO 6
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 6

Gly Ser Gly Ser
1

<210> SEQ ID NO 7
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 7

Gly Gly Gly Ser
1

<210> SEQ ID NO 8
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 8

Gly Gly Gly Gly Ser Gly Gly Gly Gly Ser
1               5                   10

<210> SEQ ID NO 9
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 9

Gly Gly Gly Gly Ser Gly Gly Gly Gly Ser Gly Gly Gly Gly Ser Gly
1               5                   10                  15

Gly Gly Gly Ser
            20

<210> SEQ ID NO 10
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 274
<212> TYPE: PRT
<213> ORGANISM: Artificial Sequence
```

-continued

<220> FEATURE:
<223> OTHER INFORMATION: synthetic polypeptide

<400> SEQUENCE: 11

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Gln Lys Pro
        35                  40                  45

Gly Gln Pro Pro Lys Leu Leu Ile Lys Tyr Ala Ser Tyr Leu Glu Ser
    50                  55                  60

Gly Val Pro Ala Arg Phe Ser Gly Ser Gly Ser Gly Thr Asp Phe Thr
65                  70                  75                  80

Leu Asn Ile His Pro Val Glu Glu Asp Ala Ala Thr Tyr Tyr Cys
                85                  90                  95

Gln His Ser Arg Glu Phe Pro Trp Thr Phe Gly Gly Gly Thr Lys Leu
            100                 105                 110

Glu Ile Lys Arg Ala Asp Ala Ala Pro Gly Gly Gly Ser Gly Gly
        115                 120                 125

Gly Gly Ser Gly Gly Gly Ser Glu Val Gln Leu Val Glu Ser Gly
    130                 135                 140

Gly Gly Leu Val Lys Pro Gly Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
            180                 185                 190

Thr Ile Tyr Tyr Ala Asp Thr Val Lys Gly Arg Phe Thr Ile Ser Arg
        195                 200                 205

Asp Asn Ala Lys Asn Thr Leu Phe Leu Gln Met Thr Ser Leu Arg Ser
    210                 215                 220

Glu Asp Thr Ala Met Tyr Tyr Cys Ala Arg Arg Gly Leu Leu Leu Asp
225                 230                 235                 240

Tyr Trp Gly Gln Gly Thr Thr Leu Thr Val Ser Ser Leu Glu Gln Lys
                245                 250                 255

Leu Ile Ser Glu Glu Asp Leu Asn Ser Ala Val Asp His His His His
            260                 265                 270

His His

<210> SEQ ID NO 12
<211> LENGTH: 541
<212> TYPE: PRT
<213> ORGANISM: Artificial Sequence
<220> FEATURE:
<223> OTHER INFORMATION: synthetic polypeptide

<400> SEQUENCE: 12

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Gln Lys Pro
        35                  40                  45

Gly Gln Pro Pro Lys Leu Leu Ile Lys Tyr Ala Ser Tyr Leu Glu Ser
    50                  55                  60

```
Gly Val Pro Ala Arg Phe Ser Gly Ser Gly Thr Asp Phe Thr
 65                  70                  75                  80

Leu Asn Ile His Pro Val Glu Glu Asp Ala Ala Thr Tyr Tyr Cys
                 85                  90                  95

Gln His Ser Arg Glu Phe Pro Trp Thr Phe Gly Gly Gly Thr Lys Leu
                100                 105                 110

Glu Ile Lys Arg Ala Asp Ala Ala Pro Gly Gly Gly Ser Gly Gly
            115                 120                 125

Gly Gly Ser Gly Gly Gly Ser Glu Val Gln Leu Val Glu Ser Gly
            130                 135                 140

Gly Gly Leu Val Lys Pro Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
            180                 185                 190

Thr Ile Tyr Tyr Ala Asp Thr Val Lys Gly Arg Phe Thr Ile Ser Arg
        195                 200                 205

Asp Asn Ala Lys Asn Thr Leu Phe Leu Gln Met Thr Ser Leu Arg Ser
210                 215                 220

Glu Asp Thr Ala Met Tyr Tyr Cys Ala Arg Arg Gly Leu Leu Leu Asp
225                 230                 235                 240

Tyr Trp Gly Gln Gly Thr Leu Thr Val Ser Ser Ala Ser Thr Lys
                245                 250                 255

Gly Pro Ser Val Phe Pro Leu Ala Pro Leu Glu Ser Ser Gly Ser Asp
            260                 265                 270

Ile Val Leu Thr Gln Ser Pro Ala Ser Leu Ala Val Ser Leu Gly Gln
        275                 280                 285

Arg Ala Thr Ile Ser Cys Arg Ala Ser Lys Ser Val Ser Thr Ser Ser
        290                 295                 300

Tyr Ser Tyr Met His Trp Tyr Gln Gln Lys Pro Gly Gln Pro Pro Lys
305                 310                 315                 320

Leu Leu Ile Lys Tyr Ala Ser Tyr Leu Glu Ser Gly Val Pro Ala Arg
                325                 330                 335

Phe Ser Gly Ser Gly Ser Gly Thr Asp Phe Thr Leu Asn Ile His Pro
            340                 345                 350

Val Glu Glu Glu Asp Ala Ala Thr Tyr Tyr Cys Gln His Ser Arg Glu
            355                 360                 365

Phe Pro Trp Thr Phe Gly Gly Gly Thr Lys Leu Glu Ile Lys Arg Ala
            370                 375                 380

Asp Ala Ala Pro Gly Gly Gly Ser Gly Gly Gly Gly Ser Gly Gly
385                 390                 395                 400

Gly Gly Ser Glu Val Gln Leu Val Glu Ser Gly Gly Gly Leu Val Lys
            405                 410                 415

Pro Gly Gly Ser Arg Lys Leu Ser Cys Ala Ala Ser Gly Phe Thr Phe
            420                 425                 430

Ser Asn Tyr Gly Met His Trp Val Arg Gln Ala Pro Glu Lys Gly Leu
            435                 440                 445

Glu Trp Val Ala Tyr Ile Ser Ser Gly Ser Ser Thr Ile Tyr Tyr Ala
            450                 455                 460

Asp Thr Val Lys Gly Arg Phe Thr Ile Ser Arg Asp Asn Ala Lys Asn
465                 470                 475                 480
```

-continued

```
Thr Leu Phe Leu Gln Met Thr Ser Leu Arg Ser Glu Asp Thr Ala Met
                485                 490                 495

Tyr Tyr Cys Ala Arg Arg Gly Leu Leu Leu Asp Tyr Trp Gly Gln Gly
            500                 505                 510

Thr Thr Leu Thr Val Ser Ser Leu Glu Gln Lys Leu Ile Ser Glu Glu
        515                 520                 525

Asp Leu Asn Ser Ala Val Asp His His His His His His
    530                 535                 540
```

<210> SEQ ID NO 13
<211> LENGTH: 808
<212> TYPE: PRT
<213> ORGANISM: Artificial Sequence
<220> FEATURE:
<223> OTHER INFORMATION: synthetic polypeptide

<400> SEQUENCE: 13

```
Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Gln Lys Pro
        35                  40                  45

Gly Gln Pro Pro Lys Leu Leu Ile Lys Tyr Ala Ser Tyr Leu Glu Ser
    50                  55                  60

Gly Val Pro Ala Arg Phe Ser Gly Ser Gly Ser Gly Thr Asp Phe Thr
65                  70                  75                  80

Leu Asn Ile His Pro Val Glu Glu Glu Asp Ala Ala Thr Tyr Tyr Cys
                85                  90                  95

Gln His Ser Arg Glu Phe Pro Trp Thr Phe Gly Gly Gly Thr Lys Leu
            100                 105                 110

Glu Ile Lys Arg Ala Asp Ala Ala Pro Gly Gly Gly Gly Ser Gly Gly
        115                 120                 125

Gly Gly Ser Gly Gly Gly Gly Ser Glu Val Gln Leu Val Glu Ser Gly
    130                 135                 140

Gly Gly Leu Val Lys Pro Gly Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
            180                 185                 190

Thr Ile Tyr Tyr Ala Asp Thr Val Lys Gly Arg Phe Thr Ile Ser Arg
        195                 200                 205

Asp Asn Ala Lys Asn Thr Leu Phe Leu Gln Met Thr Ser Leu Arg Ser
    210                 215                 220

Glu Asp Thr Ala Met Tyr Tyr Cys Ala Arg Arg Gly Leu Leu Leu Asp
225                 230                 235                 240

Tyr Trp Gly Gln Gly Thr Thr Leu Thr Val Ser Ser Ala Ser Thr Lys
                245                 250                 255

Gly Pro Ser Val Phe Pro Leu Ala Pro Leu Glu Ser Ser Gly Ser Asp
            260                 265                 270

Ile Val Leu Thr Gln Ser Pro Ala Ser Leu Ala Val Ser Leu Gly Gln
        275                 280                 285

Arg Ala Thr Ile Ser Cys Arg Ala Ser Lys Ser Val Ser Thr Ser Ser
    290                 295                 300
```

-continued

```
Tyr Ser Tyr Met His Trp Tyr Gln Gln Lys Pro Gly Gln Pro Pro Lys
305                 310                 315                 320

Leu Leu Ile Lys Tyr Ala Ser Tyr Leu Glu Ser Gly Val Pro Ala Arg
            325                 330                 335

Phe Ser Gly Ser Gly Ser Gly Thr Asp Phe Thr Leu Asn Ile His Pro
        340                 345                 350

Val Glu Glu Glu Asp Ala Ala Thr Tyr Tyr Cys Gln His Ser Arg Glu
    355                 360                 365

Phe Pro Trp Thr Phe Gly Gly Gly Thr Lys Leu Glu Ile Lys Arg Ala
370                 375                 380

Asp Ala Ala Pro Gly Gly Gly Gly Ser Gly Gly Gly Ser Gly Gly Gly
385                 390                 395                 400

Gly Gly Ser Glu Val Gln Leu Val Glu Ser Gly Gly Gly Leu Val Lys
            405                 410                 415

Pro Gly Gly Ser Arg Lys Leu Ser Cys Ala Ala Ser Gly Phe Thr Phe
        420                 425                 430

Ser Asn Tyr Gly Met His Trp Val Arg Gln Ala Pro Glu Lys Gly Leu
    435                 440                 445

Glu Trp Val Ala Tyr Ile Ser Ser Gly Ser Ser Thr Ile Tyr Tyr Ala
450                 455                 460

Asp Thr Val Lys Gly Arg Phe Thr Ile Ser Arg Asp Asn Ala Lys Asn
465                 470                 475                 480

Thr Leu Phe Leu Gln Met Thr Ser Leu Arg Ser Glu Asp Thr Ala Met
            485                 490                 495

Tyr Tyr Cys Ala Arg Arg Gly Leu Leu Leu Asp Tyr Trp Gly Gln Gly
        500                 505                 510

Thr Thr Leu Thr Val Ser Ser Ala Ser Thr Lys Gly Pro Ser Val Phe
    515                 520                 525

Pro Leu Ala Pro Leu Glu Ser Ser Gly Ser Asp Ile Val Leu Thr Gln
530                 535                 540

Ser Pro Ala Ser Leu Ala Val Ser Leu Gly Gln Arg Ala Thr Ile Ser
545                 550                 555                 560

Cys Arg Ala Ser Lys Ser Val Ser Thr Ser Ser Tyr Ser Tyr Met His
            565                 570                 575

Trp Tyr Gln Gln Lys Pro Gly Gln Pro Pro Lys Leu Leu Ile Lys Tyr
        580                 585                 590

Ala Ser Tyr Leu Glu Ser Gly Val Pro Ala Arg Phe Ser Gly Ser Gly
    595                 600                 605

Ser Gly Thr Asp Phe Thr Leu Asn Ile His Pro Val Glu Glu Glu Asp
610                 615                 620

Ala Ala Thr Tyr Tyr Cys Gln His Ser Arg Glu Phe Pro Trp Thr Phe
625                 630                 635                 640

Gly Gly Gly Thr Lys Leu Glu Ile Lys Arg Ala Asp Ala Ala Pro Gly
            645                 650                 655

Gly Gly Gly Ser Gly Gly Gly Gly Ser Gly Gly Gly Gly Ser Glu Val
        660                 665                 670

Gln Leu Val Glu Ser Gly Gly Gly Leu Val Lys Pro Gly Gly Ser Arg
    675                 680                 685

Lys Leu Ser Cys Ala Ala Ser Gly Phe Thr Phe Ser Asn Tyr Gly Met
690                 695                 700

His Trp Val Arg Gln Ala Pro Glu Lys Gly Leu Glu Trp Val Ala Tyr
705                 710                 715                 720

Ile Ser Ser Gly Ser Ser Thr Ile Tyr Tyr Ala Asp Thr Val Lys Gly
```

```
                    725                 730                 735
Arg Phe Thr Ile Ser Arg Asp Asn Ala Lys Asn Thr Leu Phe Leu Gln
            740                 745                 750

Met Thr Ser Leu Arg Ser Glu Asp Thr Ala Met Tyr Tyr Cys Ala Arg
            755                 760                 765

Arg Gly Leu Leu Leu Asp Tyr Trp Gly Gln Gly Thr Thr Leu Thr Val
            770                 775                 780

Ser Ser Leu Glu Gln Lys Leu Ile Ser Glu Glu Asp Leu Asn Ser Ala
785                 790                 795                 800

Val Asp His His His His His His
                805

<210> SEQ ID NO 14
<211> LENGTH: 112
<212> TYPE: PRT
<213> ORGANISM: Mus musculus

<400> SEQUENCE: 14

Asp Ile Val Leu Thr Gln Ser Pro Ala Ser Leu Ala Ala Val Ser Leu
1               5                   10                  15

Gly Glu Arg Ala Thr Ile Ser Tyr Arg Ala Ser Lys Ser Val Ser Thr
            20                  25                  30

Ser Gly Tyr Ser Tyr Met His Trp Asn Gln Gln Lys Pro Gly Gln Ala
        35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Glu Asp Ala Ala Thr Tyr Tyr Cys Gln His Ile
                85                  90                  95

Arg Glu Leu Asp Thr Phe Phe Gly Gly Gly Thr Lys Leu Glu Ile Lys
            100                 105                 110

<210> SEQ ID NO 15
<211> LENGTH: 15
<212> TYPE: PRT
<213> ORGANISM: Mus musculus

<400> SEQUENCE: 15

Arg Ala Ser Lys Ser Val Ser Thr Ser Gly Tyr Ser Tyr Met His
1               5                   10                  15

<210> SEQ ID NO 16
<211> LENGTH: 7
<212> TYPE: PRT
<213> ORGANISM: Mus musculus

<400> SEQUENCE: 16

Leu Val Ser Asn Leu Glu Ser
1               5

<210> SEQ ID NO 17
<211> LENGTH: 9
<212> TYPE: PRT
<213> ORGANISM: Mus musculus

<400> SEQUENCE: 17

Gln His Ile Arg Glu Leu Asp Thr Phe
1               5
```

<210> SEQ ID NO 18
<211> LENGTH: 120
<212> TYPE: PRT
<213> ORGANISM: Mus musculus

<400> SEQUENCE: 18

```
Gln Leu Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Ala Lys Arg Leu Glu Trp Val
        35                  40                  45

Ala Thr Ile Ser Ser Gly Gly Gly Ser Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Ala Tyr Ser Lys Arg Gly Ala Met Asp Tyr Trp Gly Gln
            100                 105                 110

Gly Thr Ser Val Thr Val Ser Ser
        115                 120
```

<210> SEQ ID NO 19
<211> LENGTH: 5
<212> TYPE: PRT
<213> ORGANISM: Mus musculus

<400> SEQUENCE: 19

```
Ser Tyr Thr Met Ser
1               5
```

<210> SEQ ID NO 20
<211> LENGTH: 17
<212> TYPE: PRT
<213> ORGANISM: Mus musculus

<400> SEQUENCE: 20

```
Thr Ile Ser Ser Gly Gly Gly Ser Thr Tyr Tyr Pro Asp Ser Val Lys
1               5                   10                  15

Gly
```

<210> SEQ ID NO 21
<211> LENGTH: 11
<212> TYPE: PRT
<213> ORGANISM: Mus musculus

<400> SEQUENCE: 21

```
Arg Ala Tyr Ser Lys Arg Gly Ala Met Asp Tyr
1               5                   10
```

<210> SEQ ID NO 22
<211> LENGTH: 5
<212> TYPE: PRT
<213> ORGANISM: Mus musculus

<400> SEQUENCE: 22

```
Asp Tyr Gly Met His
1               5
```

```
<210> SEQ ID NO 23
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 23

Asn Tyr Gly Met His
1               5

<210> SEQ ID NO 24
<211> LENGTH: 17
<212> TYPE: PRT
<213> ORGANISM: Mus musculus

<400> SEQUENCE: 24

Tyr Ile Ser Ser Gly Ser Ser Thr Ile Tyr Tyr Ala Asp Thr Val Lys
1               5                   10                  15

Gly

<210> SEQ ID NO 25
<211> LENGTH: 7
<212> TYPE: PRT
<213> ORGANISM: Mus musculus

<400> SEQUENCE: 25

Arg Gly Leu Leu Leu Asp Tyr
1               5

<210> SEQ ID NO 26
<211> LENGTH: 15
<212> TYPE: PRT
<213> ORGANISM: Mus musculus

<400> SEQUENCE: 26

Arg Ala Ser Lys Ser Val Ser Thr Ser Ser Tyr Ser Tyr Met His
1               5                   10                  15

<210> SEQ ID NO 27
<211> LENGTH: 7
<212> TYPE: PRT
<213> ORGANISM: Mus musculus

<400> SEQUENCE: 27

Tyr Ala Ser Tyr Leu Glu Ser
1               5

<210> SEQ ID NO 28
<211> LENGTH: 9
<212> TYPE: PRT
<213> ORGANISM: Mus musculus

<400> SEQUENCE: 28

Gln His Ser Arg Glu Phe Pro Trp Thr
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 29
```

```
Pro Leu Gly Leu Ala Gly
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 30

Arg Leu Gln Leu Lys Leu
1               5
```

ANTIBODY-MEDIATED AUTOCATALYTIC, TARGETED DELIVERY OF NANOCARRIERS TO TUMORS

CROSS-REFERENCE TO RELATED APPLICATIONS

This application is a National Phase application under 35 U.S.C. 371 of PCT/US2017/037754, filed Jun. 15, 2017, which claims the benefit of and priority to U.S. Ser. No. 62/350,423 filed Jun. 15, 2016 and which are incorporated by reference in their entirety.

STATEMENT REGARDING FEDERALLY SPONSORED RESEARCH

This invention was made with government support under NS095147, NS095817, and TR000142 awarded by National Institutes of Health. The government has certain rights in the invention.

REFERENCE TO SEQUENCE LISTING

The Sequence Listing submitted as a text file named "YU_7013_PCT_ST25.txt," created on Jun. 15, 2017, and having a size of 23,726 bytes is hereby incorporated by reference pursuant to 37 C.F.R § 1.52(e)(5).

FIELD OF THE INVENTION

The field of the invention is generally in the field of targeted drug delivery, particularly to sites of extracellular DNA such as those found in and near tumors, sites of injuries and damage, ischemic tissue, and sites of infection.

BACKGROUND OF THE INVENTION

The first nanodrug, Doxil®, which is a formulation of doxorubicin (DOX) in liposomal nanocarriers, was approved by the FDA for treatment of human patients with AIDS-related Kaposi's sarcoma in 1995 (Barenholz, et al., *Journal of Controlled Release: Official Journal of the Controlled Release Society*, 160(2):117-134 (2012)). Since then, development of nanocarriers for delivery of chemotherapeutic drugs has emerged as a promising approach to cancer drug development. Compared to free drugs, employment of nanocarriers has many advantages. For example, nanocarriers allow for delivery of hydrophobic or toxic drugs that otherwise are unable to be directly administered. They also provide protection to drugs that by themselves would be degraded or eliminated by ATP-binding cassette (ABC) transporters in the circulation. Moreover, due to the enhanced permeability and retention (EPR) effect resulting from the size difference between interendothelial junctions in tumors (40-80 nm) and healthy tissue (<8 nm) and defective lymphatic drainage in tumors (Jain, *Cancer Metastasis Rev*, 6(4):559-593 (1987)), employment of nanocarriers alters the bio-distribution of chemotherapeutic drugs and results in preferential drug accumulation in tumors. However, this passive targeting approach based on the EPR effect may not be sufficient to yield meaningful gains in cancer therapy (Chauhan, et al., *Nat Mater*, 12(11):958-962 (2013)).

To further enhance targeting efficiency, nanocarriers can be engineered through conjugation to ligands that have high affinities for molecules overexpressed in cancer cells or the tumor neovasculature or tumor microenvironment. For example, S,S-2-[3-[5¬amino-1-carboxypentyl]-ureido]-pentanedioic acid (ACUPA) targets prostate-specific membrane antigen (PSMA) (Hrkach, et al., *Sci Transl Med*, 4(128):128ra139 (2012)); iRGD targets au integrins in the tumor neovasculature (Sugahara, et al, *Cancer Cell*, 16(6): 510-520 (2009), Zhou, et al., *Biomaterials*, 33(2):583-591 (2012)); and chlorotoxin (CTX) targets matrix metalloproteinase-2 (MMP2) (Han, et al., *ACS Nano*, 10(4):4209-4218 (2016)). ACUPA-conjugated nanomedicine and iRGD-conjugated nanomedicine have successfully advanced to clinical trials and demonstrated improved efficacy (Chow, et al., *Sci Transl Med*, 5(216):216rv214 (2013), Service, et al., *Science*, 330(6002):314-315 (2010)). Nonetheless, these traditional targeting approaches suffer from a significant limitation: with the delivery of chemotherapeutic agents which kill tumor cells and neovasculature, the amount of molecules available for targeted delivery decreases with time; consequently, the efficiency of nanoparticle accumulation in tumors is reduced. Over the past several years, many attempts have been made to overcome this limitation, including efforts to employ separate nanoparticle formulations that communicate in vivo via induction of a coagulation cascade (von Maltzahn, et al., *Nat Mater*, 10(7):545-552 (2011)). However, the complexity of such systems may limit the ability to apply this technique in the clinic. Alternate strategies to target nanocarriers to tumors are needed in order to help translate nanomedicine approaches into clinical meaningful therapies.

It is an object of the invention to provide compositions, kits, and methods of identifying, diagnosising, and treating diseases and disorders.

SUMMARY OF THE INVENTION

DNA-targeted nanocarriers for encapsulating an active agent and delivering it to extracellular DNA are provided. The nanocarriers, for example, polymeric particles, liposomes, and multilamellar vesicles have targeting moiety that targets DNA conjugated thereto. The targeting moiety that targets DNA is typically an antibody, or variant, fragment, or fusion protein derived therefrom that binds to DNA or nucleosomes or components thereof, or precursors of DNA such as nucleotides, nucleosides, nucleobases. For example, the targeting moiety that targets DNA can be a variable fragment (Fv). In an example, the Fv is a scFv, di-scFv or tri-scFv. For example, the Fv is a scFv. In an example, the Fv is a di-scFv. In an example, the Fv is a tri-scFv.

The targeting moiety can be a circulating autoantibody that binds DNA such as those commonly found in patients with SLE. In some embodiments, the targeting moiety is antibody 3E10 or 5C6, or a variant, fragment, or fusion protein derived therefrom. For example, the targeting moiety is an antibody having a VH including an amino acid sequence as shown in SEQ ID NO: 2 and a VL including the amino acid sequence shown in SEQ ID NO:3 (3E10) or an antibody having a VH including an amino acid sequence as shown in SEQ ID NO: 14 and a VL including the amino acid sequence shown in SEQ ID NO: 18 (5C6), or a variant, fragment, fusion protein thereof. For example, the targeting moiety is antibody having a VH including an amino acid sequence as shown in SEQ ID NO: 2 and a VL including the amino acid sequence shown in SEQ ID NO:3 or a variant, fragment, fusion protein thereof. The targeting moiety is an antibody having a VH including an amino acid sequence as shown in SEQ ID NO: 14 and a VL including the amino acid sequence shown in SEQ ID NO: 18, or a variant, fragment, fusion protein thereof. In another example, the targeting moiety is a humanized or chimeric form of 3E10 or 5C6.

The targeting moiety can be a Fab, (Fab')2, minibody, $V_L$, $V_H$, scFv-Fc, diabody, triabody, tetrabody, or other component or derivative of antibody 3E10 or 5C6 or a variant thereof. The targeting moiety can be a variable fragment. For example, the targeting moiety can be a mono-, di-, or tri-valent single chain variable fragment (scFV) of antibody 3E10 or 5C6, or a variant thereof. In some embodiments, the scFV includes a heavy chain having an amino acid sequence selected from SEQ ID NOS:1 or 2, or 18, and a light chain having the amino acid sequence of SEQ ID NO:3 or 14. In specific embodiments, the targeting moiety includes the amino acid sequence of SEQ ID NO:11, 12, or 13.

In some embodiments, the targeting moiety can be released at the target site and serve as an active agent. For example, the targeting moiety can be linked to the nanocarrier with a disulfide bond that can be cleaved in the presence of glutathione such as can be found in a tumor's microenvironment. In particular embodiments, the released active agent is antibody 3E10 or 5C6, or a fragment, variant, of fusion protein derived therefrom.

In some embodiments, the nanocarriers are polymeric nanoparticles. The polymeric nanoparticles can be formed of one or more biodegradable polyesters or polyanhydrides, for example, poly(lactic acid), poly(glycolic acid), or poly(lactic-co-glycolic acid). In a particular embodiment, the polymeric nanoparticles are formed of PLGA-poly(ε-carbobenzoxyl-L-lysine) (PLL).

Typically, the nanocarriers have one or more active agents encapsulated therein. For example, the active(s) may be a anti-angiogenic agent, anti-proliferative, chemotherapeutic agent, cytotoxic agent, antibody or fragment or variant thereof, radiosensitizer, radioisotope, therapeutic protein, therapeutic gene, siRNA, aptamer, oligonucleotide, antisense oligonucleotide, gene modifying agent, gene expression modifying agent, or a combination thereof. In another example, the active is a PARP inhibitor. For example, the PARP inhibitor may be Olaparib ($C_{24}H_{23}FN_4O_3$).

Pharmaceutical compositions including an effective amount of nanocarrier and a pharmaceutically acceptable carrier for administration to a subject in need thereof are also provided. Methods of treating a subject in need thereof by administering the subject an effective amount of nanocarrier, typically in a pharmaceutical composition, are also disclosed. In some embodiments, the subject has cancer, ischemia, or an injury, or an infection, or a genetic or autoimmune disease. The active agents can be selected based on the intended therapeutic, diagnostic, or prophylactic use. For example, when treating cancer, the active agent(s) may be anti-angiogenic agent, anti-proliferative, chemotherapeutic agent, cytotoxic agent, radiosensitizer or a combination thereof. For treating ischemia, the active agent(s) may increase blood flow, reduce coagulation, induce arterial dilation, induce or increase thrombolysis, protect and prolong survival of cells in the area of ischemia, or a combination thereof. For treating injury the active agent(s) may be an analgesic, anesthetic, anti-inflammatory, anti-infective, cytokine, chemokine, immunomodulator, an agent that promotes wound healing, an agent that protects and prolongs survival of cells in the area of injury, or a combination thereof. For treating infection the active agent(s) may be an antimicrobial agent, antiviral agent, antibacterial agent, antibiotic, antibody or fragment of variant thereof, analgesic, anesthetic, anti-inflammatory, anti-infective, cytokine, chemokine, immunomodulator, an agent that promotes wound healing, an agent that protects and prolongs survival of cells in the area of infection, or a combination thereof.

Dosage regimens are also provided. In some embodiments, the composition is administered to the subject two or more times in intervals of hours, days, or weeks. The Examples below demonstrate that when the active agent is a chemotherapeutic agent delivered in the context of cancer, the effectiveness of the treatment improves with subsequent administrations as the active agent induce more cell death and thus more extracellular DNA at the target site. In a particular embodiment, a dosage regimen includes two, three, four, five, or more administrations of a pharmaceutical composition including nanocarriers at least one day apart.

Methods of detecting a site or sites of cancer, tissue damage, injury, or ischemia are also provided. The methods typically include administering to a subject in need thereof an effective amount a targeted-nanocarrier in a pharmaceutically acceptable carrier. The nanocarriers are typically loaded with an agent detectable using diagnostic imaging or nuclear medicine techniques, for example, by PET-CT, bone scan, MRI, CT, echocardiography, ultrasound, or x-ray.

DETAILED DESCRIPTION OF THE INVENTION

Definitions

Figure 1A:
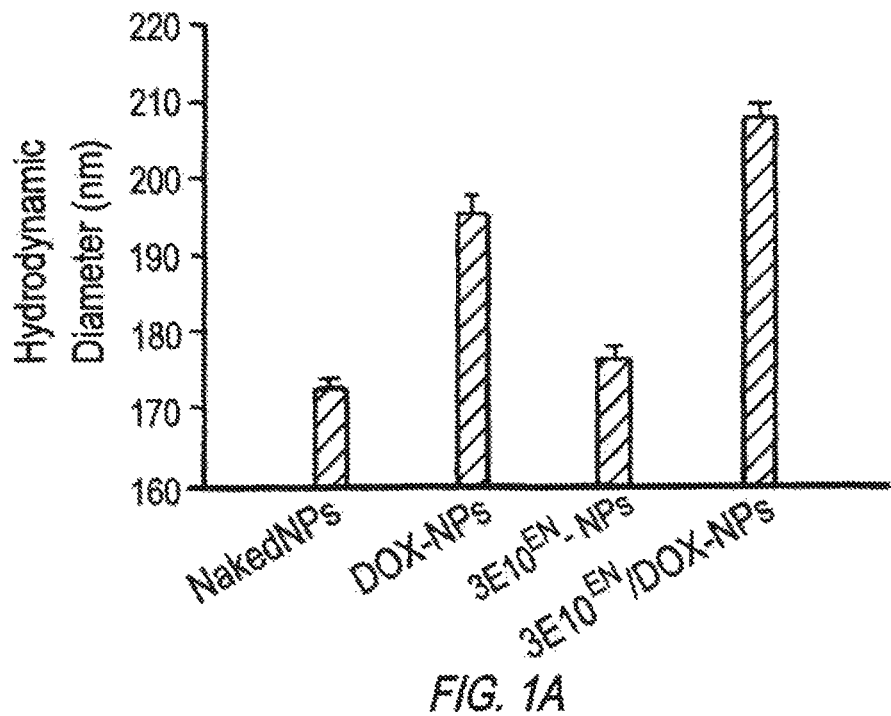
FIG. 1A is a bar graph showing the hydrodynamic diameters of nanoparticles (naked nanoparticles, DOX-NPs, $3E10^{EN}$-NPs, $3E10^{EN}$/DOX-NPs) as determined by dynamic light scattering (DLS).

As used herein, the term "3E10" refers to a monoclonal antibody produced by ATCC Accession No. PTA 2439 hybridoma.

As used herein, the term "5C6" refers to a monoclonal anti-DNA antibody with nucleolytic activity produced by a hybridoma from MRL/lpr lupus mouse model as described in Noble et al., 2014, *Sci Rep* 4:5958 doi: 10.1038/srep05958.

As used herein, the term "single chain Fv" or "scFv" as used herein means a single chain variable fragment that includes a light chain variable region ($V_L$) and a heavy chain variable region ($V_H$) in a single polypeptide chain joined by a linker which enables the scFv to form the desired structure for antigen binding (i.e., for the $V_H$ and $V_L$ of the single polypeptide chain to associate with one another to form a Fv). The $V_L$ and $V_H$ regions may be derived from the parent antibody or may be chemically or recombinantly synthesized.

As used herein, the term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917).

As used herein, the term "Framework Region" or "FR" residues are those variable domain residues other than the hypervariable region residues as herein defined.

As used herein, the term "antibody" refers to natural or synthetic antibodies that bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that bind the target antigen.

As used herein, the term "cell-penetrating anti-DNA antibody" refers to an antibody, or antigen binding fragment or molecule thereof that is transported into the nucleus of living mammalian cells and binds DNA (e.g., single-stranded and/or double-stranded DNA). In an embodiment, a cell penetrating anti-DNA antibody is transported into the nucleus of a cell without the aid of a carrier or conjugate. In another embodiment, a cell penetrating anti-DNA antibody is conjugated to a cell-penetrating moiety, such as a cell penetrating peptide. One of skill in the art will appreciate that the term "cell penetrating" can be used in the context of the present disclosure to refer to other particles having a targeting moiety that targets DNA such as scFv. For example, the term can be used to refer to a scFv that is transported into the nucleus of a cell without the aid of a carrier or conjugate and binds DNA (e.g., single-stranded and/or double-stranded DNA).

As used herein, the term "specifically binds" refers to the binding of an antibody to its cognate antigen (for example DNA) while not significantly binding to other antigens. Preferably, an antibody "specifically binds" to an antigen with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$ and $10^{12}$ mol$^{-1}$ or more) with that second molecule.

As used herein, the term "monoclonal antibody" or "MAb" refers to an antibody obtained from a substantially homogeneous population of antibodies, i.e., the individual antibodies within the population are identical except for possible naturally occurring mutations that may be present in a small subset of the antibody molecules.

As used herein, the term "DNA repair" refers to a collection of processes by which a cell identifies and corrects damage to DNA molecules. Single-strand defects are repaired by base excision repair (BER), nucleotide excision repair (NER), or mismatch repair (MMR). Double-strand breaks are repaired by non-homologous end joining (NHEJ), microhomology-mediated end joining (MMEJ), or homologous recombination. After DNA damage, cell cycle checkpoints are activated, which pause the cell cycle to give the cell time to repair the damage before continuing to divide. Checkpoint mediator proteins include BRCA1, MDC1, 53BP1, p53, ATM, ATR, CHK1, CHK2, and p21.

As used herein, the term "impaired DNA repair" refers to a state in which a mutated cell or a cell with altered gene expression is incapable of DNA repair or has reduced activity or efficiency of one or more DNA repair pathways or takes longer to repair damage to its DNA as compared to a wild type cell.

As used herein, the term "chemosensitivity" refers to the relative susceptibility of cancer cells to the effects of anti-cancer drugs. The more chemosensitive a cancer cell is, the less anticancer drug is required to kill that cell.

As used herein, the term "radiosensitivity" refers to the relative susceptibility of cells to the harmful effect of ionizing radiation. The more radiosensitive a cell is, the less radiation that is required to kill that cell. In general, it has been found that cell radiosensitivity is directly proportional to the rate of cell division and inversely proportional to the cell's capacity for DNA repair.

As used herein, the term "radioresistant" refers to a cell that does not die when exposed to clinically suitable dosages of radiation.

As used herein, the term "neoplastic cell" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

As used herein, the term "tumor" or "neoplasm" refers to an abnormal mass of tissue containing neoplastic cells. Neoplasms and tumors may be benign, premalignant, or malignant.

As used herein, the term "cancer" or "malignant neoplasm" refers to a cell that displays uncontrolled growth and division, invasion of adjacent tissues, and often metastasizes to other locations of the body.

As used herein, the term "antineoplastic" refers to a composition, such as a drug or biologic, that can inhibit or prevent cancer growth, invasion, and/or metastasis.

As used herein, the term "anti-cancer moiety" refers to any agent, such as a peptide, protein, nucleic acid, or small molecule, which can be combined with the disclosed anti-DNA antibodies to enhance the anti-cancer properties of the antibodies. The term includes antineoplastic drugs, antibodies that bind and inhibit other therapeutic targets in cancer cells, and substances having an affinity for cancer cells for directed targeting of cancer cells.

As used herein, the term "virally transformed cell" refers to a cell that has been infected with a virus or that has incorporated viral DNA or RNA into its genome. The virus can be an acutely-transforming or slowly-transforming oncogenic virus. In acutely transforming viruses, the viral particles carry a gene that encodes for an overactive oncogene called viral-oncogene (v-onc), and the infected cell is transformed as soon as v-onc is expressed. In contrast, in slowly-transforming viruses, the virus genome is inserted near a proto-oncogene in the host genome. Exemplary oncoviruses include Human papillomaviruses (HPV), Hepatitis B (HBV), Hepatitis C (HCV), Human T-lymphotropic virus (HTLV), Kaposi's sarcoma-associated herpesvirus (HHV-8), Merkel cell polyomavirus, Epstein-Barr virus (EBV), Human immunodeficiency virus (HIV), and Human cytomegalovirus (CMV).

As used herein, the "virally infected cell" refers to a cell that has been exposed to or infected with a virus or carries viral genetic material, either RNA or DNA. The virus can be an oncogenic virus or a lytic virus or a latent virus and can cause cancer, immunodeficiency, hepatitis, encephalitis, pneumonitis, respiratory illness, or other disease condition. It has previously been shown that retorviruses, specifically HIV, rely in part upon the base excision repair (BER) pathway for integration into host DNA. The ability of 3E10 to inhibit DNA repair provides a mechanism whereby 3E10 and other anti-DNA antibodies can ameliorate virally caused diseases, in particular, by interfering with DNA repair and thereby by blocking the DNA or RNA metabolism that is part of virus life cycles as well as part of viral infection of a cell.

As used herein, the term "inhibit" means to decrease an activity, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, the term "fusion protein" refers to a polypeptide formed by the joining of two or more polypeptides through a peptide bond formed between the amino terminus of one polypeptide and the carboxyl terminus of another polypeptide or through linking of one polypeptide to another through reactions between amino acid side chains (for example disulfide bonds between cysteine residues on each polypeptide). The fusion protein can be formed by the chemical coupling of the constituent polypeptides or it can be expressed as a single polypeptide from a nucleic acid sequence encoding the single contiguous fusion protein. Fusion proteins can be prepared using conventional techniques in molecular biology to join the two genes in frame into a single nucleic acid sequence, and then expressing the nucleic acid in an appropriate host cell under conditions in which the fusion protein is produced.

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

As used herein, the term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or includes a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

As used herein, the term "biodegradable" means that the materials degrades or breaks down into its component subunits, or digestion, e.g., by a biochemical process, of the material into smaller (e.g., non-polymeric) subunits.

As used herein, the term "sustained release" refers to release of a substance over an extended period of time in contrast to a bolus type administration in which the entire amount of the substance is made biologically available at one time.

As used herein, the term "particle" refers to any particle formed of, having attached thereon or thereto, or incorporating a therapeutic, diagnostic or prophylactic agent. In an example, the particle is a binding protein. For example, the particle can be an antibody. In another example, the particle is an Fv such as a scFv.

As used herein, the term "nanoparticle" generally refers to a particle having a diameter from about 10 nm up to, but not including, about 1 micron, or from 100 nm to about 1 micron. The particles can have any shape. Nanoparticles having a spherical shape are generally referred to as "nanospheres".

As used herein, the term "microspheres" is art-recognized, and includes substantially spherical colloidal structures formed from biocompatible polymers having a size ranging from about one or greater up to about 1000 microns. In general, "microcapsules," also an art-recognized term, may be distinguished from microspheres, as formed of a core and shell. The term "microparticles" is also art-recognized, and includes microspheres and microcapsules, as well as structures that may not be readily placed into either of the above two categories, all with dimensions on average of less than about 1000 microns. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10% of the median volume diameter.

As used herein, the phrase "mean particle size" generally refers to the statistical mean particle size (diameter) of the particles in a population of particles. The diameter of an essentially spherical particle may refer to the physical or hydrodynamic diameter. The diameter of a non-spherical particle may refer to the hydrodynamic diameter. As used herein, the diameter of a non-spherical particle may refer to the largest linear distance between two points on the surface of the particle. Mean particle size can be measured using methods known in the art, such as dynamic light scattering.

As used herein, the phrases "monodisperse" and "homogeneous size distribution" are used interchangeably and describe a population of nanoparticles or microparticles where all of the particles are the same or nearly the same size. As used herein, a monodisperse distribution refers to particle distributions in which 90% of the distribution lies within 15% of the median particle size, or within 10% of the median particle size, or within 5% of the median particle size.

As used herein, "molecular weight" generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

As used herein, the term "targeting moiety" refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

As used herein, the phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

As used herein, the phrase "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts.

As used herein, the term "individual," "host," "subject," and "patient" are used interchangeably to refer to any individual who is the target of administration or treatment. The subject can be a vertebrate, for example, a mammal. Thus, the subject can be a human or veterinary patient.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a therapeutic agent or prophylactic agent to reduce or diminish the symptoms of one or more diseases or disorders of the brain, such as reducing tumor size (e.g., tumor volume) or reducing or diminishing one or more symptoms of a neurological disorder, such as memory or learning deficit, tremors or shakes, etc. In still other embodiments, an "effective amount" refers to the amount of a therapeutic agent necessary to repair damaged neurons and/or induce regeneration of neurons.

As used herein, the terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "coencapsulation" refers to-the incorporation of a therapeutic agent or other material and at least one other therapeutic agent or other material in a subject composition. For example, at least two actives can be encapsulated. In another example, at least three, at least four, at least five or more actives can be encapsulated.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer that it is dispersed as small droplets, rather than being dissolved, in the polymer.

As used herein, "active agent" refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

II. Compositions

Nanoparticles having an anti-DNA antibody can be used to deliver therapeutic agents to site of exogenous DNA in vivo including, for example, tumors, regions of ischemia such as ischemic brain or region of infraction in myocardial infarction, and injuries such as skeletal muscle subject to contractile injury. When a cytotoxic agent is delivered by the nanoparticles as an active agent, the strategy not only targets extracellular DNA effectively but also yields improved delivery efficiency with time and subsequent treatments due to increased release of DNA by the dead and dying cells. Thus the disclosed compositions generally include a nanocarrier with an anti-DNA or anti-nucleosome antibody, or functional fragment, variant, or fusion protein derived therefrom conjugated thereto.

Nanocarrier compositions including one or more active agents each loaded into, attached to the surface of, and/or enclosed within a delivery vehicle, are provided.

The nanocarrier delivery vehicles can be, for example, polymeric particles, inorganic particles, silica particles, liposomes, micelles, multilamellar vesicles, or microbubbles.

In an embodiment, the delivery vehicles are nanoscale compositions, for example, 10 nm up to, but not including, about 1 micron. However, it will be appreciated that in some embodiments, and for some uses, the particles can be smaller, or larger (e.g., microparticles, etc.). Although many of the compositions disclosed herein are referred to as nanoparticle or nanacarrier compositions, it will be appreciated that in some embodiments and for some uses the carrier can be somewhat larger than nanoparticles. For example, carrier compositions can be between about 1 micron to about 1000 microns. Such compositions can be referred to as microparticulate compositions. For example, a nanocarriers according to the present disclosure may be a microparticle. Microparticles are particles having a diameter between 0.1 and 100 μm in size. In another example, the nanocarriers may be a supraparticle. Supraparticles are particles having a diameter above about 100 μm in size. For example, supraparticle may have a diameter of about 100 μm to about 1,000 μm in size.

Microbubbles are bubbles smaller than one millimetre in diameter, but larger than one micrometer with widespread application in industry, life science, and medicine. The composition of the bubble shell and filling material determine empart characteristics such as buoyancy, crush strength, thermal conductivity, and acoustic properties. In medicine they have applications in diagnostics such as imaging and therapeutics such as drug delivery.

In some embodiments for treating cancer it is desirable that the particle be of a size suitable to access the tumor microenvironment. In particular embodiments, the particle is of a size suitable to access the tumor microenvironment and/or the tumor cells by enhanced permeability and retention (EPR) effect. EPR refers to the property by which certain sizes of molecules tend to accumulate in tumor tissue much more than they do in normal tissues. Therefore, in an exemplary composition for treatment of cancer, the delivery vehicle can be in the range of about 25 nm to about 500 nm. In another example, the delivery vehicle can be in the range of about 50 nm to about 300 nm inclusive. In another example, the delivery vehicle can be in the range of about 80 nm to about 120 nm inclusive. In another example, the delivery vehicle can be in the range of about 85 nm to about 110 nm inclusive.

The polymeric nanoparticles are typically formed using an emulsion process, single or double, using an aqueous and a non-aqueous solvent. Typically, the nanoparticles contain a minimal amount of the non-aqueous solvent after solvent removal. Exemplary methods of preparing nanoparticles are described in the examples.

In some embodiments, nanoparticles are prepared using emulsion solvent evaporation method. A polymeric material is dissolved in a water immiscible organic solvent and mixed with a drug solution or a combination of drug solutions. The water immiscible organic solvent can be a GRAS ingredient such as chloroform, dichloromethane, and acyl acetate. The drug can be dissolved in, but is not limited to, one or a plurality of the following: acetone, ethanol, methanol, isopropyl alcohol, acetonitrile and Dimethyl sulfoxide (DMSO). An aqueous solution is then added into the resulting mixture solution to yield emulsion solution by emulsification. The emulsification technique can be, but not limited to, probe sonication or homogenization through a homogenizer.

In some embodiments, nanoparticles are prepared using nanoprecipitation methods or microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution. The agents may be associated with the surface of, encapsulated within, surrounded by, and/or distributed throughout the polymeric matrix of the particles.

In some embodiments, nanoparticles are prepared by the self-assembly of the amphiphilic polymers, optionally including hydrophilic and/or hydrophobic polymers, using emulsion solvent evaporation, a single-step nanoprecipitation method, or microfluidic devices.

Other exemplary methods of producing nanoparticles encompassed by the present disclosure are described in Zhou, et al., *Biomaterials,* 33(2):583-591 (2012) and Han, et al., *Nanomedicine* (2016).

Two methods to incorporate targeting moieties into the nanoparticles include: i) conjugation of targeting ligands to the hydrophilic region (e.g. PEG) of polymers prior to nanoparticle preparation; and ii) incorporation of targeting molecules onto nanoparticles where the PEG layer on the nanoparticle surface can be cleaved in the presence of a chemical or enzyme at tissues of interest to expose the targeting molecules.

In an example, particles may be microparticles or nanoparticles. Nanoparticles are often utilized for intertissue application, penetration of cells, and certain routes of administration. In an example, nanoparticles may have any diameter from 10 nm up to about 1,000 nm. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 50 nm to 400 nm, from 50 nm to 350 nm, from 50 nm to 300 nm, or from 50 nm to 200 nm. In some embodiments the nanoparticles can have a diameter less than 400 nm, less than 300 nm, or less than 200 nm. For example, the nanoparticle can have a diameter from between 50 nm and 300 nm.

In one example, the average diameters of the nanoparticles are between about 50 nm and about 500 nm, or between about 50 nm and about 350 nm. In some embodiments, the average diameters of the nanoparticles are about 100 nm.

The zeta potential of the nanoparticles is typically between about −50 mV and about +50 mV, or between about −25 mV and +25 mV, or between about −10 mV and about +10 my.

In some embodiments, the particles are brain-penetrating polymeric nanoparticles that can be loaded with drugs and optimized for intracranial convection-enhanced delivery (CED) such as those discussed in WO 2013/166487 and U.S. Published Application No. 2015/0118311. For example, the particles can be formed by emulsifying a polymer-drug solution, then removing solvent and centrifuging at a first force to remove the larger particles, then collecting the smaller particles using a second higher force to sediment the smaller particles having a diameter of less than 100 nm, or in the range of 25-75 nanometers average diameter, able to penetrate brain interstitial spaces.

Partially water-miscible organic solvents, such as benzyl alcohol, butyl lactate, and ethyl acetate (EA), allow nanoparticle formulation through an emulsion-diffusion mechanism and are able to produce smaller nanoparticles than water-immiscible solvents such as dicloromethane (DCM). Using partially water-miscible organic solvents improves the yield of brain-penetrating nanoparticles. Representative solvents that can be used include DCM, benzyl alcohol, butyl lactate, and ethyl acetate (EA), acetone. EA is particularly attractive because of its low toxicity.

To reduce aggregation, a sugar such as the FDA-approved disaccharide trehalose can added to the composition. Other sugars include glucose, sucrose and lactose. Typically, the weight ratio of sugar to nanoparticles is between 10-50%.

In an example, nanocarriers and compositions having the same can be used in the manufacture of a medicament for the treatment of a condition. In another example, the present disclosure relates to a nanocarrier or compositions having the same for use in the treatment of a condition. Examples of conditions to be treated are discussed below.

The following are exemplary materials and methods of making polymeric NPs.

A. Exemplary Nanocarriers

In some embodiments, the term "nanocarriers" is used in the context of the present disclosure to refer to agglomerated particles including a network of pores. The network of pores provides nanocarriers with a large pore volume and surface area for carrying a payload such as one or more of the exemplary actives discussed below. A large pore volume and surface area is advantageous as it can enhance the amount of payload that can be carried by the nanocarriers.

In some embodiments, the nanocarriers are not agglomerated particles including a network of pores.

1. Polymers

The nanocarrier can be a particle containing one or more hydrophilic polymers. Exemplary hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers thereof.

The nanoparticle can contain one or more hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

The hydrophobic polymer cab be an aliphatic polyester. In some embodiments, the hydrophobic polymer is poly(lactic acid), poly(glycolic acid), or poly(lactic acid-co-glycolic acid).

The nanoparticle can contain one or more biodegradable polymers. Exemplary biodegradable polymers can include polymers that are insoluble or sparingly soluble in water that are converted chemically or enzymatically in the body into water-soluble materials. Biodegradable polymers can include soluble polymers crosslinked by hydolyzable crosslinking groups to render the crosslinked polymer insoluble or sparingly soluble in water.

Biodegradable polymers in the nanoparticle can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene poly(ethylene glycol), poly(ethylene oxide), poly (ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly (ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof.

The nanoparticles can contain one or more amphiphilic polymers. Amphiphilic polymers can be polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof. In some embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both.

In some embodiments the nanoparticles contain a first amphiphilic polymer having a hydrophobic polymer block, a hydrophilic polymer block, and targeting moiety conjugated to the hydrophilic polymer block; and a second amphiphilic polymer having a hydrophobic polymer block and a hydrophilic polymer block but without the targeting moiety. The hydrophobic polymer block of the first amphiphilic polymer and the hydrophobic polymer block of the second amphiphilic polymer may be the same or different. Likewise, the hydrophilic polymer block of the first amphiphilic polymer and the hydrophilic polymer block of the second amphiphilic polymer may be the same or different.

In some embodiments the nanoparticle contains biodegradable polyesters or polyanhydrides such as poly(lactic acid), poly(glycolic acid), and poly(lactic-co-glycolic acid). For example, nanoparticles according to the present disclosure can be generated from generated poly(lactic-co-glycolic acid). For example, nanoparticles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(ε-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. Other polymers include PLGA-poly(ε-carbobenzoxyl-L-lysine) (PLL) (i.e., PLGA-PLL).

For example, nanoparticles can also contain one or more polymer conjugates containing end-to-end linkages between the polymer and a targeting moiety or a detectable label. For example, a modified polymer can be a PLGA-PEG-peptide block polymer.

For example, nanoparticles can contain one or a mixture of two or more polymers. The nanoparticles may contain other entities such as stabilizers, surfactants, or lipids. The nanoparticles may contain a first polymer having a targeting moiety and a second polymer not having the targeting moiety. By adjusting the ratio of the targeted and non-targeted polymers, the density of the targeting moiety on the exterior of the particle can be adjusted.

Nanoparticles can contain an amphiphilic polymer having a hydrophobic end, a hydrophilic end, and a targeting moiety attached to the hydrophilic end. In some embodiments the amphiphilic macromolecule is a block copolymer having a hydrophobic polymer block, a hydrophilic polymer block covalently coupled to the hydrophobic polymer block, and a targeting moiety covalently coupled to the hydrophilic polymer block. For example, the amphiphilic polymer can have a conjugate having the structure A-B-X where A is a hydrophobic molecule or hydrophobic polymer, B is a hydrophilic molecule or hydrophilic polymer, and X is a targeting moiety. Examplary amphiphilic polymers include those where A is a hydrophobic biodegradable polymer, B is PEG, and X is a targeting moiety that targets, binds.

In some embodiments the nanoparticle contains a first amphiphilic polymer having the structure A-B-X as described above and a second amphiphilic polymer having the structure A-B, where A and B in the second amphiphilic macromolecule are chosen independently from the A and B in the first amphiphilic macromolecule, although they may be the same.

2. Liposomes and Micelles

The nanocarrier can be a liposome or micelle. Liposomes are spherical vesicles composed of concentric phospholipid bilayers separated by aqueous compartments. Liposomes can adhere to and form a molecular film on cellular surfaces. Structurally, liposomes are lipid vesicles composed of concentric phospholipid bilayers which enclose an aqueous interior (Gregoriadis, et al., *Int. J. Pharm.,* 300, 125-30 2005; Gregoriadis and Ryman, *Biochem. J.* 124, 58P (1971)). Hydrophobic compounds associate with the lipid phase, while hydrophilic compounds associate with the aqueous phase.

Liposomes have the ability to form a molecular film on cell and tissue surfaces. Clinical studies have proven the efficacy of liposomes as a topical healing agent (Dausch, et al., *Klin Monatsbl Augenheilkd* 223, 974-83 (2006); Lee, et al., *Klin Monatsbl Augenheilkd* 221, 825-36 (2004)). Liposomes have also been used in ophthalmology to ameliorate keratitis, corneal transplant rejection, uveitis, endophthalmitis, and proliferative vitreoretinopathy (Ebrahim, et al., 2005; Li, et al., 2007).

Liposomes have been widely studied as drug carriers for a variety of chemotherapeutic agents (approximately 25,000 scientific articles have been published on the subject) (Gregoriadis, *N Engl J Med* 295, 765-70 (1976); Gregoriadis, et al., *Int. J. Pharm.* 300, 125-30 (2005)). Water-soluble anti-cancer substances such as doxorubicin can be protected inside the aqueous compartment(s) of liposomes delimited by the phospholipid bilayer(s), whereas fat-soluble substances such as amphotericin and capsaicin can be integrated into the phospholipid bilayer (Aboul-Fadl, *Curr Med Chem* 12, 2193-214 (2005); Tyagi, et al., *J Urol* 171, 483-9 (2004)). Topical and vitreous delivery of cyclosporine was drastically improved with liposomes (Lallemand, et al., *Eur J Pharm Biopharm* 56, 307-18 2003). Delivery of chemotherapeutic agents lead to improved pharmacokinetics and reduced toxicity profile (Gregoriadis, *Trends Biotechnol* 13, 527-37 (1995); Gregoriadis and Allison, *FEBS Lett* 45, 71-4

1974; Sapra, et al., *Curr Drug Deliv* 2, 369-81 (2005)). More than ten liposomal and lipid-based formulations have been approved by regulatory authorities and many liposomal drugs are in preclinical development or in clinical trials (Barnes, *Expert Opin Pharmacother* 7, 607-15 (2006); Minko, et al., *Anticancer Agents Med Chem* 6, 537-52 (2006)). The safety data with respect to acute, subchronic, and chronic toxicity of liposomes has been assimilated from the vast clinical experience of using liposomes in the clinic for thousands of patients.

Nanocarriers such as liposomes and micelles can be formed from one or more lipids, which can be neutral, anionic, or cationic at physiologic pH. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but limited to, 1,2-diacyl-glycero-3-phosphocholines; phosphatidylserine (PS), phosphatidylglycerol, phosphatidylinositol (PO; glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids. In some embodiments, the liposomes contain a phosphaditylcholine (PC) head group, and optionally sphingomyelin. In some embodiments, the liposomes contain DPPC. In a further embodiment, the liposomes contain a neutral lipid, such as 1,2-dioleoylphosphatidylcholine (DOPC).

In certain embodiments, the liposomes are generated from a single type of phospholipid. In some embodiments, the phospholipid has a phosphaditylcholine head group, and, can be, for example, sphingomyelin. The liposomes may include a sphingomyelin metabolite. Sphingomyelin metabolites used to formulate the liposomes include, without limitation, ceramide, sphingosine, or sphingosine 1-phosphate. The concentration of the sphingomyelin metabolites included in the lipids used to formulate the liposomes can range from about 0.1 mol % to about 10 mol %, or from about 2.0 mol % to about 5.0 mol %, or can be in a concentration of about 1.0 mol %.

Suitable cationic lipids in the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), $diC_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-,N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids may be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine). The molar ratio of a first phospholipid, such as sphingomyelin, to second lipid can range from about 5:1 to about 1:1 or 3:1 to about 1:1, or from about 1.5:1 to about 1:1, or the molar ratio is about 1:1.

In some embodiments, liposomes or micelles include phospholipids, cholesterols and nitrogen-containing lipids. Examples include phospholipids, including natural phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, and lysolecithin, as well as hydrogenated products thereof obtained in a standard manner. It is also possible to use synthetic phospholipids such as dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine as well as homo-poly {N'—[N-(2-aminoethyl)-2-aminoethyl]aspartamide}P[Asp(DET)] and block-catiomer poly(ethyleneglycol) (PEG)-b-P[Asp(DET)].

In some embodiments, the liposomes are long circulating liposomes or stealth liposomes such as those reviewed in Immordino, et al, *Int J Nanomedicine*, 1(3):297-315 (2006)), which is specifically incorporated by reference herein in its entirety. For example, liposomes have been developed with surfaces modified with a variety of molecules including glycolipids and sialic acid. Long-circulating liposomes can include, for example, synthetic polymer poly-(ethylene glycol) (PEG) in liposome composition. The PEG on the surface of the liposomal carrier can extend blood-circulation time while reducing mononuclear phagocyte system uptake (stealth liposomes) and serve as an anchor for the targeting moiety.

Antibodies and antibody fragments are widely employed for targeting moieties for liposomes due to the high specificity for their target antigens. Referred to immunoliposomes, methods of generated targeted liposomes by coupling of antibodies to the liposomal surface are known in the art. Such techniques include, but are not limited to, conventional coupling and maleimide based techniques. See also, Paszko and Senge, Curr Med Chem., 19(31):5239-77 (2012), Kelly, et al., *Journal of Drug Delivery*, Volume 2011 (2011), Article ID 727241, 11 pages.

The micelles can be polymer micelles, for example, those composed of amphiphilic di- or tri-block copolymers made of solvophilic and solvophobic blocks (see, e.g., Croy and Kwon, *Curr Pharm Des.*, 12(36):4669-84 (2006)).

3. Microbubbles

In some embodiments the nanocarrier is a microbubbles.

In some embodiments, microbubbles are dispersed in solution with active agents or dispersed in suspension with liposomes or particles encapsulating active agents. During ultrasonic exposure, microbubbles vary in size in response to oscillation of acoustic waves and eventually burst to create shock waves to transiently open the tight junctions in nearby biological tissue. Meanwhile, active agents in the solution or released from liposomes or particles diffuse rapidly across the transiently opened junctions and permeate in tissues otherwise difficult to penetrate.

In some embodiments, microbubbles are coated or filled with active agent, where ultrasonic shock waves activate the coating and cause mini explosions to release the medicine.

In some embodiments, the microbubbles have a gas core stabilized by a shell composed of proteins, lipids or polymers. They are filled with an insoluble perfluorocarbon gas, such as perfluoromethane, perfluoroethane, perfluoropropane, perfluorobutane, or perfluoropentane. In one embodiment, the microbubbles are about 1 to about 15 microns in diameter.

The microbubbles may have a protein shell formed with albumin, lysozyme, and other amphipathic proteins which are highly surface active. Albumin-coated microbubbles can be formed by sonication of a heated solution (e.g., 5% (w/v)) of human serum albumin in the presence of air. During sonication, microbubbles of air are formed which become encapsulated within a nanometer-thick shell of aggregated albumin. Heating is needed to denature the albumin prior to sonication and facilitate encapsulation, and the albumin shell is held together through disulfide bonds between cystein residues formed during cavitation.

Microbubbles may have a surfactant shell formed with mixtures of synthetic surfactants, such as SPAN-40® and TWEEN-40®. The SPAN®/TWEEN® mixture solution is sonicated in the presence of air to form stable microbubbles.

In preferred embodiments, the microbubbles have a lipid shell. Commercially available lipid-coated microbubble formulations may be used herein, including DEFINITY® (Lantheus Medical Imaging) and SONOVUE®® (Bracco Diagnostics). Phospholipids spontaneously self-assemble into a highly oriented monolayer at the air-water interface, such that their hydrophobic acyl chains face the gas and their hydrophilic headgroups face the water. The lipid molecules are held together by 'weak' physical forces, without chain entanglement, which makes the shell compliant to area expansion and compression during ultrasound insonification. Exemplary lipid molecules suitable for forming microbubbles are described above in the production of liposomes.

In other embodiments, microbubbles have a polymeric shell formed from cross-linked or entangled polymeric species, or polyelectrolyte multilayer shells. Exemplary polymeric-shelled microbubbles are described by Sirsi S and Borden M in *Bubble Sci Eng Technol*, 1(1-2):3-17 (2009).

B. Moieties that Target DNA

The disclosed nanocarriers generally include a moiety that targets DNA or component thereof, such as nucleotides or nucleosides or nucleobases, or nucleosomes or a component thereof, attached, linked, or conjugated thereto. The moiety can be conjugated to a polymer that forms the nanocarrier. In an example, the binding moiety is displayed on the outer shell of the nanocarrier.

The targeting moiety can be an antibody or variant or functional fragment or fusion protein that can bind to extracellular DNA or components thereof, nucleotides, nucleobases, or nucleosomes. Various exemplary anti-DNA/anti-nucleosome antibodies are known in the art (see, e.g., Shuster A. M. et. al., *Science*, v. 256, 1992, pp. 665-667, Isenberg, et al., *Rheumatology*, 46 (7):1052-1056 (2007))). For example, autoantibodies to single or double stranded deoxyribonucleic acid (DNA) are frequently identified in the serum of patients with systemic lupus erythematosus (SLE) and are often implicated in disease pathogenesis. The presence of circulating autoantibodies reactive against DNA (anti-DNA antibodies) is a hallmark laboratory finding in patients with systemic lupus erythematosus (SLE). Although the precise role of anti-DNA antibodies in SLE is unclear, it has been suggested that the antibodies play an active role in SLE pathophysiology. Select lupus anti-DNA autoantibodies can penetrate into live cell nuclei and inhibit DNA repair or directly damage DNA, and efforts to use these antibodies against tumors that are sensitive to DNA damage are underway (Hansen, et al., *Sci Transl Med*, 4(157):157ra142 (2012), Noble, et al., *Cancer Research*, 2015; 75(11):2285-2291, Noble, et al., *Sci Rep-Uk*, 4 (2014), Noble, et al., *Nat Rev Rheumatol* (2016)). Therefore, in some embodiments, anti-DNA antibodies can be derived or isolated from patients with SLE. In some embodiments, the anti-DNA antibodies are monoclonal antibodies, or fragments or variants thereof.

Antibodies can, for example, be naturally occurring in SLE patients, or obtained by screening of antibody libraries. The antibodies may be prepared by fusing spleen cells from a host having elevated serum levels of anti-DNA antibodies (e.g., MRL/lpr mice) with myeloma cells in accordance with known techniques or by transforming the spleen cells with an appropriate transforming vector to immortalize the cells. The cells may be cultured in a selective medium and screened to select antibodies that bind DNA.

In some embodiments, antibodies, variants, functional fragments or fusion proteins encompassed by the present disclosure can hydrolyze DNA. In other embodiments, antibodies, variants, functional fragments or fusion proteins encompassed by the present disclosure do not hydrolyze DNA.

In some embodiments, antibodies, variants, functional fragments or fusion proteins encompassed by the present disclosure are cell penetrating, nuclear membrane penetrating, or both. Accordingly, in some embodiments, an antibody, variant, functional fragment or fusion protein encompassed by the present disclosure, (1) is cell penetrating, (2) is cell penetrating, but does not penetrate the nuclear membrane, (3) is cell penetrating and nuclear penetrating, or (4) is not cell penetrating and is not nuclear membrane penetrating when conjugated to a nanocarrier. Thus in some embodiments, the nanocarrier primarily remains in the extracellular space, for example, in the tumor microenvironment. In some embodiments, the targeting moiety facilitates delivery of the nanocarrier across the cellular membrane into the cell. Put another way, in an example, the targeting moiety is cell penetrating. Thus, in some embodiments, the targeted particles are delivered into cells more efficiently or at a higher frequency than untargeted particles of the same character. In some embodiments, the targeting moiety also facilitate delivery of the nanocarrier across the nuclear membrane. In another example, the targeting moiety is not cell penetrating.

Exemplary antibodies that can be used include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the antibodies can contain the components of the CDRs necessary to penetrate cells, maintain DNA binding and/or interfere with DNA repair.

Also disclosed are variants and fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

The anti-DNA targeting moieties can be modified to improve their therapeutic potential. For example, in some embodiments, the anti-DNA targeting moiety is conjugated to another antibody specific for a second therapeutic target, for example, on or near a cancer cell or in a tumor microenvironment. For example, the anti-DNA antibody can be a fusion protein containing single chain variable fragment that binds DNA or nucleosomes and a single chain variable fragment of a monoclonal antibody that specifically binds the second therapeutic target. In other embodiments, the anti-DNA antibody is a bispecific antibody having a first heavy chain and a first light chain from an anti-DNA or anti-nucleosome antibody and a second heavy chain and a second light chain from a monoclonal antibody that specifically binds the second therapeutic target.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

The antibody can be a humanized or chimeric antibody, or a fragment, variant, or fusion protein thereof. Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule.

In some embodiments, the antibody is modified to alter its half-life. In some embodiments, it is desirable to increase the half-life of the antibody so that it is present in the circulation or at the site of treatment for longer periods of time. In other embodiments, the half-life of the anti-DNA antibody is decreased to reduce potential side effects. Antibody fragments are expected to have a shorter half-life than full size antibodies. Other methods of altering half-life are known and can be used in the described methods. For example, antibodies can be engineered with Fc variants that extend half-life, e.g., using Xtend™ antibody half-life prolongation technology (Xencor, Monrovia, Calif.).'

In some embodiments, the targeting moiety or the nanocarrier itself is conjugated to a cell-penetrating moiety, such as a cell penetrating peptide, to facilitate entry into the cell and transport to the nucleus. Examples of cell-penetrating peptides include, but are not limited to, Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). In other embodiments, the antibody is modified using TransMabs™ technology (InNexus Biotech., Inc., Vancouver, BC).

In some embodiments, the anti-DNA antibody is 3E10, 5C6, or a variant, functional fragment, or fusion protein derived therefrom. For example, the anti-DNA antibody can have a $V_H$ having an amino acid sequence as shown in SEQ ID NO: 2 and a $V_L$ having an amino acid sequence as shown in SEQ ID NO: 3 (3E10). Exemplary variants include antibodies having a $V_H$ including an amino acid sequence at least 90% identical to the amino acid sequence shown in SEQ ID NO: 2 and a $V_L$ including an amino acid sequence at least 90% identical to the sequence as shown in SEQ ID NO: 3. Other exemplary variants include antibodies having a $V_H$ including an amino acid sequence at least 95%, at least 98%, at least 99% identical to the amino acid sequence shown in SEQ ID NO: 2 and a $V_L$ including an amino acid sequence at least 95%, at least 98%, at least 99% identical to the sequence as shown in SEQ ID NO: 3. Other exemplary variants include humanized forms of 3E10 such as those described in WO 2015/106290 and WO 2016/033324.

In another example, the anti-DNA antibody can have a $V_H$ having an amino acid sequence as shown in SEQ ID NO: 14 and a $V_L$ having an amino acid sequence as shown in SEQ ID NO: 18 (5C6). Exemplary variants include antibodies having a $V_H$ having an amino acid sequence at least 90% identical to the amino acid sequence shown in SEQ ID NO: 14 and a $V_L$ having an amino acid sequence at least 90% identical to the sequence as shown in SEQ ID NO: 18. Other exemplary variants include antibodies having a $V_H$ having an amino acid sequence at least 95%, at least 98%, at least 99% identical to the amino acid sequence shown in SEQ ID NO: 14 and a $V_L$ having an amino acid sequence at least 95%, at least 98%, at least 99% identical to the sequence as shown in SEQ ID NO: 18.

The Examples below show an average of five $3E10^{EN}$ molecules conjugated to the surface of each nanoparticle was effective for targeting particles to extracellular DNA. The number of targeting molecule can generally range from about 1 to about 10,000, or from about 5 to about 1,000.

1. Exemplary Antibodies

A panel of hybridomas, including the 3E10 and 5C6 hybridomas was previously generated from the MRLmpj/lpr lupus mouse model and DNA binding activity was evaluated (Zack, et al., *J. Immunol.* 154:1987-1994 (1995); Gu, et al., *J. Immunol.*, 161:6999-7006 (1998)). Thus in some embodiments, the targeting moiety is 3E10 or 5C6 antibody or a variant, fragment, and fusion protein thereof. Each can be attached, alone or in combination, to the surface of nanocarriers encapsulating an active and target nanocarriers to sites of extracellular DNA, including but not limited to the microenvironments of apoptotic and necrotic cells and tissues.

3E10 (D31N) di-scFv ("$3E10^{EN}$") has nuclear-penetrating activity and inhibits DNA repair by itself, by may not penetrate into cell nuclei to exert its biological functions when irreversibly conjugated to nanocarriers. Thus when the anti-DNA antibody is covalently conjugated to the surface of the nanocarrier, an active agent is typically also loaded or encapsulated within the nanocarrier. However, in some embodiments, the targeting moiety is conjugated to the surface of the nanocarriers by cleavable linker or bond that releases the targeting moiety when delivered to the target site. In specific embodiments, the linker or bond is a disulfide bond. With this approach, the targeting moiety can be released from nanocarriers once it encounters the reducing tumor microenvironment due to elevated levels of glutathione (Shao, et al., *Ther Deliv,* 3(12):1409-1427 (2012)). Released antibody or fragment or fusion protein derived therefrom, then becomes an active agent that can penetrate cells as discussed above. Other cleavable linkers can be peptides which are substrates to enzymes in tumor microenvironment, such as PLGLAG (SEQ ID NO:29) (see, e.g., Aguilera, et al., *Integr Biol* (Camb), 1(5-6): 371-381 (2009)) .and RLQLKL (SEQ ID NO:30) (see, e.g., Whitney, et al., *J. Biol. Chem.*, 285(29):22532-41 (2010)).

Alternatively or in addition to having antibody conjugated to the surface of the nanocarriers, an antibody, such as 3E10 or 5C6 or a variant or a fragment or fusion protein derived therefrom or any combination thereof, may be encapsulated into nanocarriers alone or in combination with one or more additional active agents. Once released from the nanocarriers either by breakage of disulfide bonds or by release of encapsulated antibody, the free antibody would then be able to penetrate target cell nuclei and inhibit DNA repair and thereby sensitize the tumors to DNA damage or selectively kill DNA repair-deficient cancer cells. In some embodiments, some or all of the encapsulated antibody has an active agent conjugated thereto to facilitate delivery to the active agent to cells or their nuclei.

Thus, in some embodiments, the loaded or encapsulated active agent(s) does not include 3E10 or 5C6 or a fragment, variant, humanized form or fusion protein derived therefrom. In other embodiments, the loaded or encapsulated active agent(s) does include 3E10 or 5C6 or a fragment or fusion protein derived therefrom as either a free antibody, an antibody conjugated to a second active agent, or a combination thereof. Any of the embodiments can include one or more additional active agents.

a. 3E10

In the early 1990s a murine lupus anti-DNA antibody, 3E10, was tested in experimental vaccine therapy for SLE. These efforts were aimed at developing anti-idiotype antibodies that would specifically bind anti-DNA antibody in SLE patients. However, 3E10 was serendipitously found to penetrate into living cells and nuclei without causing any observed cytotoxicity (Weisbart R H, et al. *J Immunol.* 1990 144(7): 2653-2658; Zack D J, et al. *J Immunol.* 1996 157(5): 2082-2088). Studies on 3E10 in SLE vaccine therapy were then supplanted by efforts focused on development of 3E10 as a molecular delivery vehicle for transport of therapeutic molecules into cells and nuclei. 3E10 preferentially binds DNA single-strand tails, inhibits key steps in DNA single-strand and double-strand break repair (Hansen, et al., *Science Translational Medicine,* 4:157ra142 (2012)). Accordingly, one of skill in the art would appreciate that 3E10 can have a $V_H$ having an amino acid sequence as shown in SEQ ID NO: 2 and a $V_L$ having an amino acid sequence as shown in SEQ ID NO: 3. The 3E10 antibody and its single chain variable fragment which includes a D31N mutation in CDR1 of the $V_H$ (3E10 (D31N) scFv) and di- and tri-valent fusions thereof penetrate into cells and nuclei and have proven capable of transporting therapeutic protein cargoes attached to the antibody either through chemical conjugation or recombinant fusion. Protein cargoes delivered to cells by 3E10 or 3E10 (D31N) scFv include catalase, p53, and Hsp70 (Weisbart R H, et al. *J Immunol.* 2000 164: 6020-6026; Hansen J E, et al. *Cancer Res.* 2007 February 15; 67(4): 1769-74; Hansen J E, et al. *Brain Res.* 2006 May 9; 1088(1): 187-96). 3E10 (D31N) scFv effectively mediated delivery of Hsp70 to neurons in vivo and this resulted in decreased cerebral infarct volumes and improved neurologic function in a rat stroke model (Zhan X, et al. *Stroke.* 2010 41(3): 538-43).

3E10 and 3E10 (D31N) scFv and di- and tri-valent fusions thereof, without being conjugated to any therapeutic protein, enhance cancer cell radiosensitivity and chemosensitivity and that this effect is potentiated in cells deficient in DNA repair. Moreover, 3E10 and 3E10 scFv and di- and tri-valent fusions thereof are selectively lethal to cancer cells deficient in DNA repair even in the absence of radiation or chemotherapy. The Food and Drug Administration (FDA) has established a pathway for the development of monoclonal antibodies into human therapies, and 3E10 has already been approved by the FDA for use in a Phase I human clinical trial designed to test the efficacy of 3E10 in experimental vaccine therapy for SLE (Spertini F, et al. *J Rheumatol.* 1999 26(12): 2602-8).

Experiments indicate that 3E10 (D31N) scFv penetrates cell nuclei by first binding to extracellular DNA or its degradation products and then following them into cell nuclei through the ENT2 nucleoside salvage pathway (Weisbart, *Scientific Reports,* 5:Article number: 12022 (2015) doi:10.1038/srep12022). When administered to mice and rats 3E10 is preferentially attracted to tissues in which extracellular DNA is enriched, including tumors, regions of ischemic brain in stroke models, and skeletal muscle subject to contractile injury (Weisbart, et al., *Sci Rep.,* 5:12022 (2015), Hansen, et al., *J Biol Chem,* 282(29):20790-20793 (2007), Weisbart, et al., *Mol Immunol,* 39(13):783-789 (2003), Zhan, et al., *Stroke: A Journal of Cerebral Circulation,* 41(3):538-543 (2010)). Thus the presence of extracellular DNA enhances the nuclear uptake of 3E10 (D31N) scFv. Furthermore, 3E10 (D31N) scFv preferentially localizes into tumor cell nuclei in vivo, likely due to increased DNA in the local environment released from ischemic and necrotic regions of tumor.

b. 5C6

5C6 induces γH2AX in BRCA2$^{(-)}$ but not BRCA2$^{(+)}$ cells and selectively suppresses the growth of the BRCA2$^{(-)}$ cells. Mechanistically, 5C6 appears to induce senescence in the BRCA2$^{(-)}$ cells. Senescence is a well-known response to DNA damage, and DNA damaging agents, including many chemotherapeutics, induce senescence after prolonged exposure (Sliwinska, et al., *Mech. Ageing Dev.,* 130:24-32 (2009); to Poele, et al., *Cancer Res.* 62:1876-1883 (2002); Achuthan, et al., *J. Biol. Chem.,* 286:37813-37829 (2011)). These observations establish that 5C6 penetrates cell nuclei and damages DNA, and that cells with preexisting defects in DNA repair due to BRCA2 deficiency are more sensitive to this damage than cells with intact DNA repair. See U.S. Published Application No. 2015/0376279. Furthermore, one of skill in the art would appreciate that 5C6 can have a $V_H$ having an amino acid sequence as shown in SEQ ID NO: 14 and a $V_L$ having an amino acid sequence as shown in SEQ ID NO: 18.

2. Fragments and Fusion Proteins

In some embodiments, the targeting moiety and/or active agent is composed of one or more antigen binding antibody fragments and/or antigen binding fusion proteins of the antibody 3E10 or 5C6, or a variant thereof. The antigen binding molecules typically bind to the epitope of 3E10 or 5C6, and can, for example, maintain a function or activity of the full antibody.

Exemplary fragments and fusions include, but are not limited to, single chain antibodies, single chain variable fragments (scFv), di-scFv, tri-scFv, diabody, triabody, teratbody, disulfide-linked Fvs (sdFv), Fab', F(ab')$_2$, Fv, and single domain antibody fragments (sdAb).

In some embodiments, the targeting moeity includes two or more scFv. For example, the targeting moiety can be a scFv or a di-scFv. In some embodiments, each scFv can include one, two, or all three complementarity determining regions (CDRs) of the heavy chain variable region ($V_L$) of 3E10 or 5C6, or a variant thereof. The scFv can include one, two, or all three CDRs of the light chain variable region ($V_L$) of 3E10 or 5C6, or a variant thereof. The molecule can include the heavy chain variable region and/or light chain variable region of 3E10 or 5C6, or a variant thereof.

A single chain variable fragment can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a linker have been developed without significantly disrupting antigen binding or specificity of the binding. The linker is chosen to permit the heavy chain and light chain to bind together in their proper conformational orientation. The linker is usually rich in glycine for flexibility, and typically also includes serine or threonine for solubility. The linker can link, for example, the N-terminus of the $V_H$ with the C-terminus of the $V_L$, or vice versa. scFv can also be created directly from subcloned heavy and light chains derived from a hybridoma. In some embodiments, the scFv retains, or improves or increases the specificity of the original immunoglobulin, while removing of the constant regions and introducing the linker.

Exemplary molecules that include two or more single chain variable fragments (scFv) including the light chain variable region ($V_L$) of 3E10 or 5C6, or a variant thereof, and the heavy chain variable region ($V_H$) of 3E10 or 5C6, or a variant thereof of the antibody 3E10 or 5C6 include, but are not limited to, divalent-scFv (di-scFv), trivalent-scFv (tri-scFv), multivalent-scFv (multi-scFv), diabodies, triabodies, tetrabodies, etc., of scFvs.

Divalent single chain variable fragments can be engineered by linking two scFvs. This can be done by producing a single peptide chain with two $V_H$ and two $V_L$ regions, yielding a di-scFvs referred to as a tandem di-scFv. ScFvs can also be designed with linker peptides that are too short for the two variable regions to fold together (about five amino acids), forcing scFvs to dimerize and form a divalent single chain variable fragment referred to as a diabody. Diabodies have been shown to have dissociation constants up to 40-fold lower than corresponding scFvs, indicating that they have a much higher affinity to their target. Even shorter linkers (one or two amino acids) lead to the formation of trimers (triabodies or tribodies). Tetrabodies have also been produced and have been shown to exhibit an even higher affinity to their targets than diabodies.

The disclosed targeting moieties include antigen binding antibody fragments and fusion proteins of 3E10 or 5C6 and variants thereof that typically bind to the same epitope as the parent antibody 3E10 or 5C6. In some embodiments, the antigen binding molecule is a di-, tri-, or multivalent scFv. Although the antigen binding antibody fragment or fusion protein of the antigen binding molecule can include additional antibody domains (e.g., constant domains, hinge domains, etc.), in some embodiments it does not. For example, 3E10 binds DNA and inhibits DNA repair, which is synthetically lethal to DNA repair-deficient cells. This function is independent of any 3E10 constant regions. By contrast, non-penetrating antibodies such as cetuximab that target extracellular receptors depend in part on Fc-mediated activation of ADCC and complement to exert an effect on tumors. Elimination of the Fc from non-penetrating antibodies could therefore diminish the magnitude of their effect on tumors, but Fc is not required for 3E10 to have an effect on cancer cells. Therefore, 3E10 fragments or fusions that lack an Fc region should be unable to activate ADCC and complement and therefore carry a lower risk of nonspecific side effects.

a. Single Chain Variable Fragments

The single chain variable fragments disclosed herein can include antigen binding fragments of 3E10 or 5C6, or a variant thereof. The monoclonal antibody 3E10 and active fragments and exemplary variants thereof that are transported in vivo to the nucleus of mammalian cells without cytotoxic effect are discussed in U.S. Pat. Nos. 4,812,397 and 7,189,396, and U.S. Published Application No. 2014/0050723. Other 3E10 antibody compositions, including fragments and fusions thereof, suitable for use with the disclosed nanocarriers are discussed in, for example, WO 2012/135831, WO 2016/033321, WO 2015/106290, and WO 2016/033324. 5C6 is described in U.S. Published Application No. 2015/0376279.

An scFv includes a light chain variable region (V$_L$) and a heavy chain variable region (V$_H$) joined by a linker. In an example, the linker includes in excess of 12 amino acid residues with (Gly4Ser)3 (SEQ ID NO:10) being one of the more favoured linkers for a scFv. In an example, the scFv is a disulfide stabilized Fv (or diFv or dsFv), in which a single cysteine residue is introduced into a FR of VH and a FR of VL and the cysteine residues linked by a disulfide bond to yield a stable Fv. In an example, the scFv is a dimeric scFv (di-scFV), i.e., a protein including two scFv molecules linked by a non-covalent or covalent linkage, e.g., by a leucine zipper domain (e.g., derived from Fos or Jun) or trimeric scFV (tri-scFv). In another example, two scFv's are linked by a peptide linker of sufficient length to permit both scFv's to form and to bind to an antigen, e.g., as described in U.S. Published Application No. 2006/0263367. Additional details are discussed and exemplified below and elsewhere herein.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

The fragments and fusions of antibodies disclosed herein can have bioactivity. For example, the fragments and fusions, whether attached to other sequences or not, can include insertions, deletions, substitutions, or other selected modifications of particular regions or specific amino acids residues. In some embodiments, the activity of the fragment or fusion is not significantly reduced or impaired compared to the nonmodified antibody or antibody fragment.

b. Antibody Sequences
i. 3E10 Light Chain Variable Region
An amino acid sequence for the light chain variable region of 3E10 is:

```
                                        (SEQ ID NO: 3)
DIVLTQSPASLAVSLGQRATISCRASKSVSTSSYSYMHWYQQKPGQP

PKLLIKYASYLESGVPARFSGSGSGTDFTLNIHPVEEEDAATYYCQH

SREFPWTFGGGTKLEIK.
```

The complementarity determining regions (CDRs) are shown with underlining. Other 3E10 light chain sequences are known in the art. See, for example, Zack, et al., *J. Immunol.*, 15; 154(4):1987-94 (1995); GenBank: L16981.1—Mouse Ig rearranged L-chain gene, partial cds; GenBank: AAA65681.1-immunoglobulin light chain, partial [*Mus musculus*]).

The complementarity determining regions (CDRs) are shown with underlining, including

```
CDR L1:
                                        (SEQ ID NO: 26)
RASKSVSTSSYSYMH;

CDR L2:
                                        (SEQ ID NO: 27)
YASYLES;

CDR L3:
                                        (SEQ ID NO: 28)
QHSREFPWT.
``` ii. 3E10 Heavy Chain Variable Region
An amino acid sequence for the heavy chain variable region of 3E10 is:

```
(SEQ ID NO: 1; Zack, et al., Immunology and Cell
Biology, 72:513-520 (1994)
EVQLVESGGGLVKPGGSRKLSCAASGFTFSDYGMHWVRQAPEKGLE

WVAYISSGSSTIYYADTVKGRFTISRDNAKNTLFLQMTSLRSEDTA

MYYCARRGLLLDYWGQGTTLTVSS;
```

GenBank: L16981.1—Mouse Ig rearranged L-chain gene, partial cds; and GenBank: AAA65679.1—immunoglobulin heavy chain, partial [*Mus musculus*]). The complementarity determining regions (CDRs) are shown with underlining.

An amino acid sequence for a preferred variant of the heavy chain variable region of 3E10 is:

```
                                        (SEQ ID NO: 2)
EVQLVESGGGLVKPGGSRKLSCAASGFTFSNYGMHWVRQAPEKGLE

WVAYISSGSSTIYYADTVKGRFTISRDNAKNTLFLQMTSLRSEDTA

MYYCARRGLLLDYWGQGTTLTVSS.
```

The complementarity determining regions (CDRs) are shown with underlining.

Amino acid position 31 of the heavy chain variable region of 3E10 has been determined to be influential in the ability of the antibody and fragments thereof to penetrate nuclei and bind to DNA. For example, D31N mutation (bolded and italicized in SEQ ID NOS:1 and 2) in CDR1 penetrates nuclei and binds DNA with much greater efficiency than the original antibody (Zack, et al., *Immunology and Cell Biology*, 72:513-520 (1994), Weisbart, et al., *J. Autoimmun.*, 11, 539-546 (1998); *Weisbart, Int. J. Oncol.*, 25, 1867-1873 (2004)).

The complementarity determining regions (CDRs) are shown with underlining, including CDR H1.1 (original sequence): DYGMH (SEQ ID NO:22); CDR H1.2 (with D31N mutation): NYGMH (SEQ ID NO:23); CDR H2: YISSGSSTIYYADTVKG (SEQ ID NO:24); CDR H3: RGLLLDY (SEQ ID NO:25).

In addition to 3E10 and its fragments described above, additional anti-DNA antibodies may be used to target nanocarriers to DNA and to deliver nanocarriers to tumors or sites of damage or infection and into cells. These include the nuclear-penetrating anti-DNA antibody 5C6 as specified below.

iii. 5C6 Light Chain Variable Region

An amino acid sequence for the kappa light chain variable region (VL) of mAb 5C6 is:

(SEQ ID NO: 14)
DIVLTQSPASLAAVSLGERATISYRASKSVSTSGYSYMHWNQQKPG

QAPRLLIYLVSNLESGVPARFSGSGSGTDFTLNIHPVEEEDAATYY

CQHIRELDTFFGGGTKLEIK.

The complementarity determining regions (CDRs) are shown with underlining, including CDR L1: RASKSVSTSGYSYMH (SEQ ID NO:15); CDR L2: LVSNLES (SEQ ID NO:16); CDR L3: QHIRELDTF (SEQ ID NO:17).

iv. 5C6 Heavy Chain Variable Region

An amino acid sequence for the heavy chain variable region (VH) of mAb 5C6 is:

(SEQ ID NO: 18)
QLKLVESGGGLVKPGGSLKLSCAASGFTFSSYTMSWVRQTPAKRLE

WVATISSGGGSTYYPDSVKGRFTISRDNARNTLYLQMSSLRSEDTA

MYYCARRAYSKRGAMDYWGQGTSVTVSS.

The complementarity determining regions (CDRs) are shown with underlining, including CDR H1: SYTMS (SEQ ID NO:19); CDR H2: TISSGGGSTYYPDSVKG (SEQ ID NO:20); CDR H3: RAYSKRGAMDY(SEQ ID NO:21).

c. Linkers

The term "linker" as used herein includes, without limitation, peptide linkers. The peptide linker can be any size provided it does not interfere with the binding of the epitope by the variable regions. In some embodiments, the linker includes one or more glycine and/or serine amino acid residues. Monovalent single-chain antibody variable fragments (scFvs) in which the C-terminus of one variable domain are typically tethered to the N-terminus of the other variable domain via a 15 to 25 amino acid peptide or linker. The linker is chosen to permit the heavy chain and light chain to bind together in their proper conformational orientation. Linkers in diabodies, triabodies, etc., typically include a shorter linker than that of a monovalent scFv as discussed above. Di-, tri-, and other multivalent scFvs typically include three or more linkers. The linkers can be the same, or different, in length and/or amino acid composition. Therefore, the number of linkers, composition of the linker(s), and length of the linker(s) can be determined based on the desired valency of the scFv as is known in the art. The linker(s) can allow for or drive formation of a di-, tri-, and other multivalent scFv.

For example, a linker can include 4-8 amino acids. In a particular embodiment, a linker includes the amino acid sequence GQSSRSS (SEQ ID NO:4). In another embodiment, a linker includes 15-20 amino acids, for example, 18 amino acids. In a particular embodiment, the linker includes the amino acid sequence GQSSRSSSGGGSSGGGS (SEQ ID NO:5). Other flexible linkers include, but are not limited to, the amino acid sequences Gly-Ser, Gly-Ser-Gly-Ser (SEQ ID NO:6), Ala-Ser, Gly-Gly-Gly-Ser (SEQ ID NO:7), $(Gly_4-Ser)_2$ (SEQ ID NO:8) and $(Gly_4-Ser)_4$ (SEQ ID NO:9), and $(Gly-Gly-Gly-Gly-Ser)_3$ (SEQ ID NO:10).

d. Variants

The scFv can be composed of an antibody fragment or fusion protein including an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of 3E10 or 5C6 (e.g., SEQ ID NO:1, 2, 3, 14, and/or 18, respectively), and which binds to the epitope of 3E10 or 5C6, is selectively lethal to or selectively increases the radiosensitivity and/or chemosensitivity of cells deficient in DNA repair, or a combination thereof. The scFv can be composed of an antibody fragment or fusion protein that includes a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the variable heavy chain and/or light chain of 3E10 or 5C6 (e.g., SEQ ID NO:22-25 and 26-28, or 19-21 and 15-17, respectively), and which binds to the epitope of 3E10 or 5C6, is selectively lethal to or selectively increases the radiosensitivity and/or chemosensitivity of cells deficient in DNA repair, or a combination thereof. The determination of percent identity of two amino acid sequences can be determined by BLAST protein comparison. In some embodiments, scFv includes one, two, three, four, five, or all six of the CDRs of the above-described preferred variable domains and which binds to the epitope of 3E10 or 5C6, is selectively lethal to or selectively increases the radiosensitivity and/or chemosensitivity of cells deficient in DNA repair, or a combination thereof.

Predicted complementarity determining regions (CDRs) of the light chain variable sequence for 3E10 or 5C6 are provided above. See also GenBank: AAA65681.1—immunoglobulin light chain, partial [*Mus musculus*]. Predicted complementarity determining regions (CDRs) of the heavy chain variable sequence for 3E10 and 5C6 are provide above. See, for example, Zack, et al., *Immunology and Cell Biology*, 72:513-520 (1994) and GenBank Accession number AAA65679.1.

e. Exemplary scFv

Exemplary 3E10 scFV include mono-scFv 3E10 (D31N), di-scFv 3E10 (D31N), and tri-scFv 3E10 (D31N).

The amino acid sequence for scFv 3E10 (D31N) is:

(SEQ ID NO: 11)
```
1         10        20        30        40        51
AGIHDIVLTQSPASLAVSLGQRATISCRASKSVSTSSYSYMHWYQQKPGQP 61        71        81        91        101
PKLLIKYASYLESGVPARFSGSGSGTDFTLNIHPVEEEDAATYYCQHSRE 111       121       131       141       151
FPWTFGGGTKLEIKRADAAPGGGGSGGGGSGGGGSEVQLVESGGGLVKPG 161       171       181       191       201
GSRKLSCAASGFTFSNYGMHWVRQAPEKGLEWVAYISSGSSTIYYADTVK 211       221       231       241       251
GRFTISRDNAKNTLFLQMTSLRSEDTAMYYCARRGLLLDYWGQGTTLTVS 261       271
SLEQKLISEEDLNSAVDHHHHHH.
```

Annotation of scFv Protein Domains with Reference to SEQ ID NO:11

AGIH sequence increases solubility (amino acids 1-4 of SEQ ID NO:11)
Vk variable region (amino acids 5-115 of SEQ ID NO:11)
Initial (6 aa) of light chain CH1 (amino acids 116-121 of SEQ ID NO:11)

(GGGGS)3 linker (amino acids 122-136 of SEQ ID NO:11)
VH variable region (amino acids 137-252 of SEQ ID NO:11)
Myc tag (amino acids 253-268 of SEQ ID NO:11)
His 6 tag (amino acids 269-274 of SEQ ID NO:11)

Amino Acid Sequence of 3E10 Di-scFv (D31N)

Di-scFv 3E10 (D31N) is a di-single chain variable fragment including 2× the heavy chain and light chain variable regions of 3E10 and wherein the aspartic acid at position 31 of the heavy chain is mutated to a asparagine. The amino acid sequence for di-scFv 3E10 (D31N) is:

```
                                          (SEQ ID NO: 12)
1         10        20        30        40        51
AGIHDIVLTQSPASLAVSLGQRATISCRASKSVSTSSYSYMHWYQQKPGQP 61        71        81        91       101
PKLLIKYASYLESGVPARFSGSGSGTDFTLNIHPVEEEDAATYYCQHSRE 111       121       131       141       151
FPWTFGGGTKLEIKRADAAPGGGGSGGGGSGGGGSEVQLVESGGGLVKPG 161       171       181       191       201
GSRKLSCAASGFTFSNYGMHWVRQAPEKGLEWVAYISSGSSTIYYADTVK 211       221       231       241       251
GRFTISRDNAKNTLFLQMTSLRSEDTAMYYCARRGLLLDYWGQGTTLTVS 261       271       281       291       302
SASTKGPSVFPLAPLESSGSDIVLTQSPASLAVSLGQRATISCRASKSVST 312       322       332       342       352
SSYSYMHWYQQKPGQPPKLLIKYASYLESGVPARFSGSGSGTDFTLNIHP 362       372       382       392       402
VEEEDAATYYCQHSREFPWTFGGGTKLEIKRADAAPGGGGSGGGGSGGGG 412       422       432       442       452
SEVQLVESGGGLVKPGGSRKLSCAASGFTFSNYGMHWVRQAPEKGLEWVA 462       472       482       492       502
YISSGSSTIYYADTVKGRFTISRDNAKNTLFLQMTSLRSEDTAMYYCARR 512       522       532
GLLLDYWGQGTTLTVSSLEQKLISEEDLNSAVDHHHHHH.
```

Annotation of Di-scFv Protein Domains with Reference to SEQ ID NO: 12

AGIH sequence increases solubility (amino acids 1-4 of SEQ ID NO:12)
Vk variable region (amino acids 5-115)
Initial (6 aa) of light chain CH1 (amino acids 116-121 of SEQ ID NO:12)
(GGGGS)3 linker (amino acids 122-136 of SEQ ID NO:12)
VH variable region (amino acids 137-252 of SEQ ID NO:12)
Linker between Fv fragments consisting of human IgG CH1 initial 13 amino acids (amino acids 253-265 of SEQ ID NO:12)
Swivel sequence (amino acids 266-271 of SEQ ID NO:12)
Vk variable region (amino acids 272-382 of SEQ ID NO:12)
Initial (6 aa) of light chain CH1 (amino acids 383-388 of SEQ ID NO:12)
(GGGGS)3 linker (amino acids 389-403 of SEQ ID NO:12)
VH variable region (amino acids 404-519 of SEQ ID NO:12)
Myc tag (amino acids 520-535 of SEQ ID NO:12)
His 6 tag (amino acids 536-541 of SEQ ID NO:12)

Amino Acid Sequence for Tri-scFv

Tri-scFv 3E10 (D31N) is a tri-single chain variable fragment including 3× the heavy chain and light chain variable regions of 310E and wherein the aspartic acid at position 31 of the heavy chain is mutated to an asparagine. The amino acid sequence for tri-scFv 3E10 (D31N) is:

```
                                          (SEQ ID NO: 13)
1         10        20        30        40        51
AGIHDIVLTQSPASLAVSLGQRATISCRASKSVSTSSYSYMHWYQQKPGQP 61        71        81        91       101
PKLLIKYASYLESGVPARFSGSGSGTDFTLNIHPVEEEDAATYYCQHSRE 111       121       131       141       151
FPWTFGGGTKLEIKRADAAPGGGGSGGGGSGGGGSEVQLVESGGGLVKPG 161       171       181       191       201
GSRKLSCAASGFTFSNYGMHWVRQAPEKGLEWVAYISSGSSTIYYADTVK 211       221       231       241       251
GRFTISRDNAKNTLFLQMTSLRSEDTAMYYCARRGLLLDYWGQGTTLTVS 261       271       281       291       302
SASTKGPSVFPLAPLESSGSDIVLTQSPASLAVSLGQRATISCRASKSVST 312       322       332       342       352
SSYSYMHWYQQKPGQPPKLLIKYASYLESGVPARFSGSGSGTDFTLNIHP 362       372       382       392       402
VEEEDAATYYCQHSREFPWTFGGGTKLEIKRADAAPGGGGSGGGGSGGGG 412       422       432       442       452
SEVQLVESGGGLVKPGGSRKLSCAASGFTFSNYGMHWVRQAPEKGLEWVA 462       472       482       492       502
YISSGSSTIYYADTVKGRFTISRDNAKNTLFLQMTSLRSEDTAMYYCARR 512       522       532       542       552
GLLLDYWGQGTTLTVSSASTKGPSVFPLAPLESSGSDIVLTQSPASLAVS 562       572       582       592       603
LGQRATISCRASKSVSTSSYSYMHWYQQKPGQPPKLLIKYASYLESGVPAR 613       623       633       643       653
FSGSGSGTDFTLNIHPVEEEDAATYYCQHSREFPWTFGGGTKLEIKRADA 663       673       683       693       703
APGGGGSGGGGSGGGGSEVQLVESGGGLVKPGGSRKLSCAASGFTFSNYG 713       723       733       743       753
MHWVRQAPEKGLEWVAYISSGSSTIYYADTVKGRFTISRDNAKNTLFLQM 763       773       783       793       803
TSLRSEDTAMYYCARRGLLLDYWGQGTTLTVSSLEQKLISEEDLNSAVDH

HHHHH.
```

Annotation of Tri-scFv Protein Domains with Reference to SEQ ID NO: 13

AGIH sequence increases solubility (amino acids 1-4 of SEQ ID NO:13)
Vk variable region (amino acids 5-115 of SEQ ID NO:13)
Initial (6 aa) of light chain CH1 (amino acids 116-121 of SEQ ID NO:13)
(GGGGS)$_3$ linker (amino acids 122-136 of SEQ ID NO:13)
VH variable region (amino acids 137-252 of SEQ ID NO:13)

Linker between Fv fragments consisting of human IgG CH1 initial 13 amino acids (amino acids 253-265 of SEQ ID NO:13)

Swivel sequence (amino acids 266-271 of SEQ ID NO:13)

Vk variable region (amino acids 272-382 of SEQ ID NO:13)

Initial (6 aa) of light chain CH1 (amino acids 383-388 of SEQ ID NO:13)

(GGGGS)3 linker (amino acids 389-403 of SEQ ID NO:13)

VH variable region (amino acids 404-519 of SEQ ID NO:13)

Linker between Fv fragments consisting of human IgG $C_H1$ initial 13 amino acids (amino acids 520-532 of SEQ ID NO:13)

Swivel sequence (amino acids 533-538 of SEQ ID NO:13)

Vk variable region (amino acids 539-649 of SEQ ID NO:13)

Initial (6 aa) of light chain CH1 (amino acids 650-655 of SEQ ID NO:13)

(GGGGS)3 linker (amino acids 656-670 of SEQ ID NO:13)

VH variable region (amino acids 671-786 of SEQ ID NO:13)

Myc tag (amino acids 787-802 of SEQ ID NO:13)

His 6 tag (amino acids 803-808 of SEQ ID NO:13)

WO 2016/033321 and Noble, et al., *Cancer Research*, 75(11):2285-2291 (2015), show that di-scFv and tri-scFv have improved and additional activities compared to their monovalent counterpart. The subsequences corresponding to the different domains of each of the exemplary fusion proteins are also provided below. One of skill in the art will appreciate that the exemplary fusion proteins, or domains thereof, can be utilized to construct fusion proteins discussed in more detail above. For example, in some embodiments, the di-scFv includes a first scFv including a Vk variable region (e.g., amino acids 5-115 of SEQ ID NO:12, or a functional variant or fragment thereof), linked to a VH variable domain (e.g., amino acids 137-252 of SEQ ID NO:12, or a functional variant or fragment thereof), linked to a second scFv including a Vk variable region (e.g., amino acids 272-382 of SEQ ID NO:12, or a functional variant or fragment thereof), linked to a VH variable domain (e.g., amino acids 404-519 of SEQ ID NO:12, or a functional variant or fragment thereof). In some embodiments, a tri-scFv includes a di-scFv linked to a third scFv domain including a Vk variable region (e.g., amino acids 539-649 of SEQ ID NO:13, or a functional variant or fragment thereof), linked to a VH variable domain (e.g., amino acids 671-786 of SEQ ID NO:13, or a functional variant or fragment thereof).

The Vk variable regions can be linked to VH variable domains by, for example, a linker (e.g., (GGGGS)$_3$ (SEQ ID NO:10), alone or in combination with a (6 aa) of light chain CH1 (amino acids 116-121 of SEQ ID NO:12). Other suitable linkers are discussed above and known in the art. scFv can be linked by a linker (e.g., human IgG CH1 initial 13 amino acids (253-265) of SEQ ID NO:12), alone or in combination with a swivel sequence (e.g., amino acids 266-271 of SEQ ID NO:12). Other suitable linkers are discussed above and known in the art.

Therefore, a di-scFv can include amino acids 5-519 of SEQ ID NO:12. A tri-scFv can include amino acids 5-786 of SEQ ID NO:13. In some embodiments, the fusion proteins include additional domains. For example, in some embodiments, the fusion proteins include sequences that enhance solubility (e.g., amino acids 1-4 of SEQ ID NO:12). Therefore, in some embodiments, a di-scFv can include amino acids 1-519 of SEQ ID NO:12. A tri-scFv can include amino acids 1-786 of SEQ ID NO:13. In some embodiments that fusion proteins include one or more domains that enhance purification, isolation, capture, identification, separation, etc., of the fusion protein. Exemplary domains include, for example, Myc tag (e.g., amino acids 520-535 of SEQ ID NO:12) and/or a His tag (e.g., amino acids 536-541 of SEQ ID NO:12). Therefore, in some embodiments, a di-scFv can include the amino acid sequence of SEQ ID NO:12. A tri-scFv can include the amino acid sequence of SEQ ID NO:13. Other substitutable domains and additional domains are discussed in more detail above.

C. Additional Moieties

1. Additional Targeting Moieties

The nanocarriers can include one or more additional binding moieties or targeting moieties that specifically bind to the target of interest. Representative targeting moieties include, but are not limited to, antibodies and antigen binding fragments thereof, aptamers, peptides, and small molecules. The binding moiety can be conjugated to a polymer that forms the nanocarrier. Typically the binding moiety is displayed on the outer shell of the nanocarrier. The outer shell can serves as a shield to prevent the nanocarrier from being recognized by a subject's immune system thereby increasing the half-life of the nanocarrier in the subject. The nanoparticles can contain a hydrophobic core. In the case of liposaomal nanoparticles the core can also be hydrophilic. In some embodiments, the hydrophobic core is made of a biodegradable polymeric material. The inner core carries therapeutic payloads and releases the therapeutic payloads at a sustained rate after systemic, intraperitoneal, oral, pulmonary, or topical administration. The nanocarrier also optionally include a detectable label, for example a fluorophore or NMR contrast agent that allows visualization of nanocarriers.

The targeting moiety of the nanocarrier can be an antibody or antigen binding fragment thereof. The targeting moieties should have an affinity for a cell-surface receptor or cell-surface antigen on the target cells. The targeting moieties may result in internalization of the nanocarrier within the target cell.

The targeting moiety can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, bacterial cells, fungal cells, and organ specific cells. The cell markers can be specific for endothelial, ectodermal, or mesenchymal cells. Representative cell specific markers include, but are not limited to cancer specific markers.

The targeting moiety can be a peptide. The targeting peptides can be covalently associated with the polymer and the covalent association can be mediated by a linker.

The targeting moiety can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody or a fragment, variant, or fusion protein thereof. The antibody can be in monomeric or polymeric form. The antigen binding portion of the antibody can be any portion that has at least one antigen binding site, such as Fab, F(ab)$_2$, dsFv, sFv, diabodies, and triabodies. In certain embodiments, the antibody is a single chain antibody.

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

2. Additional Moieties

The nanocarriers can contain one or more polymer conjugates containing end-to-end linkages between the polymer and a moiety. The moiety can be a targeting moiety, a detectable label, or a therapeutic, prophylactic, or diagnostic agent. For example, a polymer conjugate can be a PLGA-PEG-phosphonate. The additional targeting elements may refer to elements that bind to or otherwise localize the nanocarriers to a specific locale. The locale may be a tissue, a particular cell type, or a subcellular compartment. The targeting element of the nanocarrier can be an antibody or antigen binding fragment thereof, an aptamer, or a small molecule (less than 500 Daltons). The additional targeting elements may have an affinity for a cell-surface receptor or cell-surface antigen on a target cell and result in internalization of the nanocarrier within the target cell.

D. Active Agents

Agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered. Exemplary materials to be incorporated are drugs and imaging agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, epothilones A-F, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs including mRNAs, antisense, siRNA, miRNA, anti-miRNA, piRNA, aptamers, ribozymes, external guide sequences for ribonuclease P, and triplex forming agents such as tcPNAs). In some embodiments, the active agent is a vector, plasmid, or other polynucleotide encoding an oligonucleotide such as those discussed above.

Exemplary drugs to be delivered include anti-angiogenic agents, antiproliferative and chemotherapeutic agents such as rampamycin.

Representative classes of diagnostic materials include paramagnetic molecules, fluorescent compounds, magnetic molecules, and radionuclides. Exemplary materials include, but are not limited to, metal oxides, such as iron oxide, metallic particles, such as gold particles, etc. Biomarkers can also be conjugated to the surface for diagnostic applications.

One or more active agents may be formulated alone or with excipients or encapsulated on, in or incorporated into the nanocarriers. Active agents include therapeutic, prophylactic, neutraceutical and diagnostic agents. Any suitable agent may be used. These include organic compounds, inorganic compounds, proteins, polysaccharides, nucleic acids or other materials that can be incorporated using standard techniques.

Active agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof. Suitable active agents have a size greater than about 1,000 Da for small peptides and polypeptides, more typically at least about 5,000 Da and often 10,000 Da or more for proteins. Nucleic acids are more typically listed in terms of base pairs or bases (collectively "bp"). Nucleic acids with lengths above about 10 bp are typically used in the present method. More typically, useful lengths of nucleic acids for probing or therapeutic use will be in the range from about 20 bp (probes; inhibitory RNAs, etc.) to tens of thousands of bp for genes and vectors. The active agents may also be hydrophilic molecules, and optionally have a low molecular weight.

Alternatively, the biodegradable polymers may encapsulate cellular materials, such as for example, cellular materials to be delivered to antigen presenting cells as described below to induce immunological responses.

Prophylactics can include compounds alleviating swelling, reducing radiation damage, and anti-inflammatories.

For imaging, radioactive materials such as Technetium99 ($^{99m}$Tc) or magnetic materials such as Fe$_2$O$_3$ could be used. Examples of other materials include gases or gas emitting compounds, which are radioopaque. The most common imaging agents for brain tumors include iron oxide and gadolinium. Diagnostic agents can be radioactive, magnetic, or x-ray or ultrasound-detectable. Other detectable labels include, for example, a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent. These may be encapsulated within, dispersed within, or conjugated to the polymer.

For example, a fluorescent label can be chemically conjugated to a polymer of the nanocarrier to yield a fluorescently labeled polymer. In other embodiments the label is a contrast agent. A contrast agent refers to a substance used to enhance the contrast of structures or fluids within the body in medical imaging. Contrast agents are known in the art and include, but are not limited to agents that work based on X-ray attenuation and magnetic resonance signal enhancement. Suitable contrast agents include iodine and barium.

Active agents can be selected based on the type of treatment being employed. Exemplary active agents for treating cancer, ischemia, and injury are discussed in more detail below.

The Examples below show that DOX was encapsulated with 6.0% by weight in nanoparticles. Active agent loading depends on factors including the chemical nature of active agent and composition of the nanocarrier, however, in generally, about 1% to about 50% of active agent by weight is loaded into the nanocarrier. Loading can be 5% to 25%.

III. Methods of Making

A. Conjugates

Methods of polymer synthesis are described, for instance, in Braun et al. (2005) Polymer Synthesis: Theory and Practice. New York, N.Y.: Springer. The polymers may be synthesized via step-growth polymerization, chain-growth polymerization, or plasma polymerization.

In some embodiments an amphiphilic polymer is synthesized starting from a hydrophobic polymer terminated with a first reactive coupling group and a hydrophilic polymer terminated with a second reactive coupling group capable of reacting with the first reactive coupling group to form a covalent bond. One of either the first reactive coupling group or the second reactive coupling group can be a primary amine, where the other reactive coupling group can be an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. One of either the first reactive coupling group or the second reactive coupling group can be an aldehyde, where the other reactive coupling group can be an aldehyde reactive linking group such as hydrazides, alkoxyamines, and primary amines. One of either the first reactive coupling group or the second reactive coupling group can be a thiol, where the other reactive coupling group can be a sulfhydryl reactive group such as maleimides, haloacetyls, and pyridyl disulfides.

In some embodiments a hydrophobic polymer terminated with an amine or an amine-reactive linking group is coupled to a hydrophilic polymer terminated with complimentary reactive linking group. For example, an NHS ester activated PLGA can be formed by reacting PLGA-CO(OH) with NHS and a coupling reagent such as dicyclohexylcarbodiimide (DCC) or ethyl(dimethylaminopropyl) carbodiimide (EDC). The NHS ester activated PLGA can be reacted with a hydrophilic polymer terminated with a primary amine, such as a PEG-NH$_2$ to form an amphiphilic PLGA-b-PEG block copolymer.

In some embodiments a conjugate of an amphiphilic polymer with a targeting moiety is formed using the same or similar coupling reactions. In some embodiments the conjugate is made starting from a hydrophilic polymer terminated on one end with a first reactive coupling group and terminated on a second end with a protective group. The hydrophilic polymer is reacted with a targeting moiety having a reactive group that is complimentary to the first reactive group to form a covalent bond between the hydrophilic polymer and the targeting moiety. The protective group can then be removed to provide a second reactive coupling group, for example to allow coupling of a hydrophobic polymer block to the conjugate of the hydrophilic polymer with the targeting moiety. A hydrophobic polymer terminated with a reactive coupling group complimentary to the second reactive coupling group can then be covalently coupled to form the conjugate. Of course, the steps could also be performed in reverse order, i.e. a conjugate of a hydrophobic polymer and a hydrophilic polymer could be formed first followed by deprotection and coupling of the targeting moiety to the hydrophilic polymer block.

In some embodiments a conjugate is formed having a moiety conjugated to both ends of the amphiphilic polymer. For example, an amphiphilic polymer having a hydrophobic polymer block and a hydrophilic polymer block may have targeting moiety conjugated to the hydrophilic polymer block and an additional moiety conjugated to the hydrophobic polymer block. In some embodiments the additional moiety can be a detectable label. In some embodiments the additional moiety is a therapeutic, prophylactic, or diagnostic agent. For example, the additional moiety could be a moiety used for radiotherapy. The conjugate can be prepared starting from a hydrophobic polymer having on one end a first reactive coupling group and a another end first protective group and a hydrophilic polymer having on one end a second reactive coupling group and on another end a second protective group. The hydrophobic polymer can be reacted with the additional moiety having a reactive coupling group complimentary to the first reactive coupling group, thereby forming a conjugate of the hydrophobic polymer to the additional moiety. The hydrophilic polymer can be reacted with a targeting moiety having a reactive coupling group complimentary to the second reactive coupling group, thereby forming a conjugate of the hydrophilic polymer to the targeting moiety. The first protective group and the second protective group can be removed to yield a pair of complimentary reactive coupling groups that can be reacted to covalently link the hydrophobic polymer block to the hydrophilic polymer block.

B. Nanocarrier Formation

1. Emulsion Methods

In some embodiments, a nanoparticle is prepared using an emulsion solvent evaporation method. For example, a polymeric material is dissolved in a water immiscible organic solvent and mixed with a drug solution or a combination of drug solutions. In some embodiments a solution of a therapeutic, prophylactic, or diagnostic agent to be encapsulated is mixed with the polymer solution. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or a more of the following: PPARgamma activators (e.g. Rosiglitazone, (RS)-5-[4-(2-[methyl(pyridin-2-yl)amino] ethoxy)benzyl]thiazolidine-2,4-dione, Pioglitazone, (RS)-5-(4-[2-(5-ethylpyridin-2-yl]ethoxylbenzyl]thiazolidine-2,4-dione, Troglitazone, (RS)-5-(4-[(6-hydroxy-2,5,7,8-tetramethylchroman-2-yl)methoxy]benzyl)thiazolidine-2,4-dione etc.), prostagladin E2 analog (PGE2, (5Z,11α,13E,15S)-7-[3-hydroxy-2-(3-hydroxyoct-1-enyl)-5-oxo-cyclopentyl]hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), Fibroblast Growth Factor 21 (FGF-21), Irisin, RNA, DNA, chemotherapeutic compounds, nuclear magnetic resonance (NMR) contrast agents, or combinations thereof. The water immiscible organic solvent, can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and Dimethyl sulfoxide (DMSO).

In some embodiments the polymer solution contains one or more polymer conjugates as described above. The polymer solution can contain a first amphiphilic polymer conjugate having a hydrophobic polymer block, a hydrophilic polymer block, and a targeting moiety conjugated to the hydrophilic end. In some embodiments the polymer solution contains one or more additional polymers or amphiphilic polymer conjugates. For example the polymer solution may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the targeting moieties can be controlled. The first amphiphilic polymer may be present from 1% to 100% by weight of the polymers in the polymer solution. For example, the first amphiphilic polymer can be present at 10%, 20%, 30%, 40%, 50%, or 60% by weight of the polymers in the polymer solution.

An aqueous solution is then added into the resulting mixture solution to yield emulsion solution by emulsification. The emulsification technique can be, but not limited to, probe sonication or homogenization through a homogenizer. The plaque-targeted peptides or fluorophores or drugs may be associated with the surface of, encapsulated within, surrounded by, and/or distributed throughout the polymeric matrix of this inventive particle.

2. Nanoprecipitation Method

In another embodiment, a multimodal nanoparticle is prepared using nanoprecipitation methods or microfluidic devices. A polymeric material is mixed with a drug or drug combinations in a water miscible organic solvent. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or more of the following: PPARgamma activators (e.g. Rosiglitazone, (RS)-5-[4-(2-[methyl(pyridin-2-yl)amino] ethoxy)benzyl]thiazolidine-2,4-dione, Pioglitazone, (RS)-5-(4-[2-(5-ethylpyridin-2-yl)ethoxy]benzyl)thiazolidine-2,4-dione, Troglitazone, (RS)-5-(4-[(6-hydroxy-2,5,7,8-tetramethylchroman-2-yl)methoxy]benzyl)thiazolidine-2,4-dione etc.), prostagladin E2 analog (PGE2, (5Z,11α,13E,15S)-7-[3-hydroxy-2-(3-hydroxyoct-1-enyl)-5-oxo-cyclopentyl] hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), RNA, DNA, chemotherapeutic compounds, nuclear magnetic resonance (NMR) contrast agents, or combinations thereof. The water miscible organic solvent, can be, but is not limited to, one or more of the following: acetone, ethanol, methanol, isopropyl alcohol, acetonitrile and Dimethyl sulfoxide (DMSO). The resulting mixture solution is then added to a polymer non-solvent, such as an aqueous solution, to yield nanoparticle solution. The plaque-targeted peptides or fluorophores or drugs may be associated with the surface of, encapsulated within, surrounded by, and/or distributed throughout the polymeric matrix of this inventive particle.

3. Microfluidics

Methods of making nanoparticles using microfluidics are known in the art. Suitable methods include those described in U.S. Patent Application Publication No. 2010/0022680 A1 by Karnik et al. In general, the microfluidic device includes at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the nanoparticles having the desired size and density of moieties on the surface. By varying the pressure and flow rate in the inlet channels and the nature and composition of the fluid sources nanoparticles can be produced having reproducible size and structure.

4. Other Methodologies

Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1,000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

Hot Melt Microencapsulation.

In this method, the polymer is first melted and then mixed with the solid particles. The mixture is suspended in a non-miscible solvent (like silicon oil), and, with continuous stirring, heated to 5°C above the melting point of the polymer. Once the emulsion is stabilized, it is cooled until the polymer particles solidify. The resulting microparticles are washed by decantation with petroleum ether to give a free-flowing powder. Microparticles with sizes between 0.5 to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1,000-50,000 Da.

Solvent Removal.

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1-300 microns can be obtained by this procedure. The external morphology of spheres produced with this technique is highly dependent on the type of polymer used.

Spray-Drying.

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

Hydrogel Microparticles.

Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

5. Liposome and Micelle Formation

Liposomes typically have an aqueous core. The aqueous core can contain water or a mixture of water and alcohol. Suitable alcohols include, but are not limited to, methanol, ethanol, propanol, (such as isopropanol), butanol (such as n-butanol, isobutene, sec-butanol, tart-butanol, pentane (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

Liposomes include, for example, small unilamellar vesicles (SUVs) formed by a single lipid bilayer, large unilamellar vesicles (LANs), which are vesicles with relatively large particles formed by a single lipid bilayer, and multi-lamellar vesicles (MLVs), which are formed by multiple membrane layers. Thus, the liposomes can have either one or several aqueous compartments delineated by either one (unilamellar) or several (multilamellar) phospholipid bilayers (Sapra, et al., Curr. Drug Deliv., 2, 369-81 (2005)). Multilamellar liposomes have more lipid bilayers for hydrophobic therapeutic agents to associate with. Thus, potentially greater amounts of therapeutic agent are available within the liposome to reach the target cell.

Liposomes can be of any particle size, for example the mean particle diameter can be about 10 to about 2000 nm. In one embodiment of the invention, the mean particle diameter is about 10, 20, 25, 30, 40, 50, 100, 200, 300, 400, 500, 600, 700, 800, 900, 1,000, 1,250, 1,500, 1,750, 2,000 nm (or any range between about 10 and about 2,000 nm) or more. In one embodiment of the invention, the mean particle diameter is about 2,000, 1,750, 1,500, 1,250, 1,000, 900, 800, 700, 600, 500, 400, 300, 200, 100, 50, 40, 30, 25, 20, 10 rim (or any range between about 2,000 and 10 nm) or less. The mean particle diameter may be about 20 to about 1,000 nm, about 100 to about 1,500 nm, about 100 to about 1,000 nm, about 100 to about 700 nm, about 200 to about 2,000 nm, about 1,000 to about 2,000 nm, or about 750 to about 1,500 nm. Particle diameter refers to the diameter of a particle measured by dynamic light scattering.

The liposomal formulations can contain large liposomes ranging from 1 to 100% of the liposome population in the formulation. In some embodiments, large liposomes represent greater than approximately 50% of the liposome population in the formulation.

Methods of manufacturing liposomes are known in the art and can include, for example, drying down of the lipids from organic solvents, dispersion of the lipids in aqueous media, purification of the resultant liposomes, and analysis of the final product. Some methods of liposome manufacture include, for example, extrusion methods, the Mozafari method, the polyol dilution method, the bubble method, and the heating method.

The micelles may be prepared in a conventional manner, for example, by reversed-phase evaporation, ether injection, surfactant-based techniques, etc. Polymer micelle formulations utilizing a block copolymer having a hydrophilic segment and a hydrophobic segment have been disclosed, e.g., in U.S. Application No. 20160114058, WO 2009/142326 A1 and WO 2010/013836 A1.

C. Methods of Encapsulating or Attaching Molecules to the Surface of the Particles There are two principle groups of molecules to be encapsulated or attached to the polymer, either directly or via a coupling molecule: targeting molecules, attachment molecules and therapeutic, nutritional, diagnostic or prophylactic agents. These can be coupled using standard techniques. The targeting molecule or therapeutic molecule to be delivered can be coupled directly to the polymer or to a material such as a fatty acid which is incorporated into the polymer.

Functionality refers to conjugation of a ligand to the surface of the particle via a functional chemical group (carboxylic acids, aldehydes, amines, sulfhydryls and hydroxyls) present on the surface of the particle and present on the ligand to be attached. Functionality may be introduced into the particles in two ways.

The first is during the preparation of the particles, for example during the emulsion preparation of particles by incorporation of stablizers with functional chemical groups.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

Various other methods of producing a nanocarriers encapsulating an active agent are known in the art. For example, methods of loading nanoporous structures are reviewed in Wang et al. (2009) J. Mater. Chem. 19, 6451. In one example, nanocarriers may be loaded by contacting the nanocarrier with an aqueous solution of an active followed by a period of incubation. The active solution can contain an excess of the amount of active to be loaded onto the supraparticle and incubation can occur at room temperature. Agitation of the solution containing the supraparticle and the payload may be used to enhance loading of the payload.

IV. Pharmaceutical Compositions

The particles can be formulated with appropriate pharmaceutically acceptable carriers into pharmaceutical compositions for administration to an individual in need thereof. The formulations can be administered enterally (e.g., oral) or parenterally (e.g., by injection or infusion).

The particles can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

In some embodiments, the nanocarriers are administered systemically by, for example, injection or infusion. In some embodiments, the nanocarriers are administered locally by injection or infusion. In more specific embodiments, the nanocarriers are administered to the central nervous system, particularly the brain, by convection enhanced delivery (CED).

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required nanocarrier size in the case of dispersion and/or by the use of surfactants. In many cases, isotonic agents, for example, sugars or sodium chloride, are included.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, exemplary methods of preparation include vacuum-drying and freeze-drying techniques which yield a powder of the active ingredient plus any additional desired ingredient from a previously sterile-filtered solution thereof. The powders can be prepared in such a manner that the nanocarriers are porous in nature, which can increase dissolution of the nanocarriers. Methods for making porous nanocarriers are well known in the art.

Enteral formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition, which may include plasticizers, pigments, colorants, stabilizing agents, and glidants. Formulations can be prepared using one or more pharmaceutically acceptable excipients, including diluents, preservatives, binders, lubricants, disintegrators, swelling agents, fillers, stabilizers, and combinations thereof.

Controlled release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

V. Methods of Use

A. Methods of Treatment

The disclosed nanocarriers can be used to deliver active agents to sites extracellular DNA in vivo. Typically an effective amount of active agent-load nanocarriers with an anti-DNA or anti-nucleosome targeting moiety, such as 3E10 or a fragment or fusion protein derived therefrom, are administered to a subject in need thereof. As used herein, the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to the selected active agent and a variety of factors such as subject-dependent variables (e.g., age, immune system health, etc.), the disease, and the treatment being effected. As discussed in more detail below, in some embodiments, the subject has cancer, ischemia, or an injury. The compositions can be more efficient, less toxic, or a combination thereof when compared to a control. In some embodiments, the control is cells, tissue, or a subject treated with free active agent, or active agent encapsulated in an untargeted nanocarrier.

Methods of detecting a site or sites of cancer, tissue damage, injury, or ischemia are also provided. The methods typically include administering to a subject in need thereof an effective amount a targeted-nanocarrier in a pharmaceutically acceptable carrier. The nanocarriers are typically loaded with an agent detectable using diagnostic imaging or nuclear medicine techniques, for example, by PET-CT, bone scan, MRI, CT, echocardiography, ultrasound, or x-ray.

B. Dosage Regimens

A key feature that distinguishes the microenvironment within tumors from that of healthy tissue is the presence of a comparatively larger amount of extracellular DNA (exDNA) (Weisbart, et al., *Sci Rep.*, 5:12022 (2015), Stroun, et al., *Clin Chim Acta,* 313(1-2):139-142 (2001), Sueoka-Aragane, et al., *PloS One,* 9(12) (2014), Wen, et al., *Cancer Research,* 73(14):4256-4266 (2013)), which originates from actively dividing, apoptotic or necrotic tumor cells and neutrophil extracellular traps (Wen, et al., *Cancer Research,* 73(14):4256-4266 (2013), Hawes, et al., *Cancer Research,* 75(20):4260-4264 (2015), Demers, et al., *Proc Natl Acad Sci USA,* 109(32):13076-13081 (2012)). Importantly, the amount of exDNA in the region of tumors further increases during treatment with cytotoxic agents, such as DOX, that cause tumor cell death and release of DNA (Swystun, et al., *J Thromb Haemost,* 9(11):2313-2321 (2011), Hansen, et al., *Sci Transl Med,* 4(157):157ra142 (2012)). The greater concentration of exDNA in the tumor environment compared to normal tissues offers an opportunity to develop a novel tumor targeting approach using an agent that has a high affinity with DNA.

The Examples below illustrate the when the nanocarriers are loaded with an active agent that induces cell death at the target site, localization of the anti-DNA antibody-nanocarriers becomes more and more efficient at targeting extracellular DNA as time goes by and more treatments are delivered, because as that happens the dead or dying cells release more and more DNA and attract more and more of the targeted nanocarriers to the site of extracellular DNA. This approach can be referred to as "autocatalytic," meaning it creates its own positive feedback loop to stimulate better and better localization of the nanocarriers to the target site. Although this approach is particularly effective for treating cancer, and other diseases, disorders, and conditions in which increased cell death is desired, dosage regimens include two or more administrations can be utilized for any method of treatment.

In general, by way of example only, dosage forms useful in the disclosed methods can include doses in the range of 1 mg to 1,000 mg, 10 mg to 750 mg, 15 mg to 500 mg, or 20 mg to 250 mg, or 25 mg to 200 mg, or 30 mg to 150 mg, or 35 mg to 125 mg, or 40 mg to 100 mg, or 45 mg to 90 mg, or 50 mg to 80 mg of nanocarrier.

Dosage range depends on drug to be delivered, the delivery vehicle, and the method of delivery. In the Examples below, mice were administered 1 mg/mouse of nanoparticles.

In some embodiments, the composition is administered to a subject in need thereof once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments the composition is administered to a subject one, twice, or three times weekly. In some embodiments, the composition is administered to a subject one, twice, or three times monthly.

In particular embodiments, the dose is about 1 mg/kg to about 1,500 mg/kg administered weekly administered in one or more administrations. For example, in specific embodiments, a subject is administered about 10 mg/kg, 20, mg/kg, 30 mg/kg, 40 mg/kg, 50 mg/kg, 60 mg/kg, 70 mg/kg, 80 mg/kg, 90 mg/kg or 100 mg/kg once, twice, or three times weekly. In some embodiments, a single dose is sufficient to improve one or more symptoms of a disease. In some embodiments, the improvement after the second dose is greater than the first dose.

C. Diseases to Be Treated

1. Cancer a. Cancers to be Treated

The disclosed compositions and methods can be used to treat cancer in a subject in need thereof. In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth. The Examples below indicate that the particles and methods disclosed herein are useful for treating cancer in vivo.

Malignant tumors that may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers, such as vascular cancer such as multiple myeloma; adenocarcinomas and sarcomas of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

The disclosed compositions can be used to treat cells undergoing unregulated growth, invasion, or metastasis.

Tumor cell hypoxia is now recognized as a problem in cancer therapy because it makes cancer cells resistant to treatment with radiation and some chemotherapeutics. Hypoxia is also known to cause impaired DNA repair in cancer cells. Accordingly, in some embodiments, the disclosed compositions are used as targeted agents for hypoxic tumor cells.

As discussed above, in some embodiments, 3E10 antibody or a fragment or fusion protein derived therefrom, in addition to serving as a targeting moiety, is also an active agent. As discussed in WO 2012/135831 and WO 2016/033321, 3E10 antibody and fragments and fusion proteins active agent are particularly usefully for treating cells with impair DNA repair, and can be used alone or in combination with DNA damaging agents and radiotherapy.

In some embodiments, the compositions are lethal to cells with impaired DNA repair. The cells can be defective in the expression of a gene or in the function of a protein involved in DNA repair, DNA synthesis, or homologous recombination. Exemplary genes and associated products include XRCC1, ADPRT (PARP-1), ADPRTL2, (PARP-2), POLYMERASE BETA, CTPS, MLH1, MSH2, FANCD2, PMS2, p53, p21, PTEN, RPA, RPAJ, RPA2, RPA3, XPD, ERCC1, XPF, MMS19, RAD51, RAD51B, RAD51C, RAD51D, DMC1, XRCCR, XRCC3, BRCA1, BRCA2, PALB2, RAD52, RAD54, RAD50, MRE11, NB51, WRN, BIM, KU70, KU80, ATM ATR CHK1, CHK2, FANC family of genes, FANCA, FANCB, FANCC, FANCD1, FANCD2, FANCE, FANCF, FANCG, FANCL, FANCM, RAM, and RAD9.

In some embodiments, the defective gene is a tumor suppressor gene. In some embodiments, the gene is associated with maintenance of chromosomal integrity and/or protection from genotoxic stress. In some embodiments, the cells are deficient in single and/or double strand break repair.

In some embodiments, the cells have one or more mutations in BRCA1, BRCA2, and/or PTEN. Gene mutations, such as BRCA1, BRCA2, PTEN mutations, can be identified using standard PCR, hybridization, or sequencing techniques.

In particular embodiments, the cancer cell is defective in DNA damage repair due to hypoxia.

Therefore, in some embodiments, the compositions can be used to treat cancers arising from DNA repair deficient familial syndromes, such as breast, ovarian, and pancreatic cancers. In these embodiments, the anti-DNA antibodies can be effective without radiotherapy or chemotherapy. For example, the compositions can be used to treat cancers that are linked to mutations in BRCA1, BRCA2, PALB2, or RAD51B, RAD51C, RAD51D, or related genes. The compositions can also be used to treat colon cancers, endometrial tumors, or brain tumors linked to mutations in genes associated with DNA mismatch repair, such as MSH2, MLH1, PMS2, and related genes. The antigen binding molecules can also be used to treat cancers with silenced DNA repair genes, such as BRCA1, MLH1, OR RAD51B, RAD51C, orRAD51D. The antigen binding molecules can also be used to treat cancers associated with chromosomal maintenance or genotoxic stress, for example, cancers in which PTEN is mutated or silences. PTEN is frequently inactivated in many cancers including breast, prostate, glioma, melanoma, and lung cancers. In these embodiments, the ability of the antigen binding molecules to inhibit DNA repair combined with the inherent repair deficiencies or other susceptibilities of these cancers can be sufficient to induce cell death.

A representative but non-limiting list of cancers that can be treating using the disclosed compositions include cancers of the blood and lymphatic system (including leukemias, Hodgkin's lymphomas, non-Hodgkin's lymphomas, solitary plasmacytoma, multiple myeloma), cancers of the genitourinary system (including prostate cancer, bladder cancer, renal cancer, urethral cancer, penile cancer, testicular cancer), cancers of the nervous system (including mengiomas, gliomas, glioblastomas, ependymomas) cancers of the head and neck (including squamous cell carcinomas of the oral cavity, nasal cavity, nasopharyngeal cavity, oropharyngeal cavity, larynx, and paranasal sinuses), lung cancers (including small cell and non-small cell lung cancer), gynecologic cancers (including cervical cancer, endometrial cancer, vaginal cancer, vulvar cancer ovarian and fallopian tube cancer), gastrointestinal cancers (including gastric, small bowel, colorectal, liver, hepatobiliary, and pancreatic cancers), skin cancers (including melanoma, squamous cell carcinomas, and basal cell carcinomas), breast cancer (including ductal and lobular cancer and triple negative breast cancers), and pediatric cancers (including neuroblastoma, Ewing's sarcoma, Wilms tumor, medulloblastoma).

In some embodiments, the cancer is a neoplasm or tumor that demonstrates some resistance to radiotherapy or chemotherapy. In particular embodiments, the cancer cell is resistant to radiation or chemotherapy due to hypoxia.

Cancers that are resistant to radiotherapy using standard methods include, but are not limited to, sarcomas, renal cell cancer, melanoma, lymphomas, leukemias, carcinomas, blastomas, and germ cell tumors.

b. Exemplary Active Agents for Cancer Treatment

In addition or alternative to 3E10 antibody or a fragment or fusion protein derived therefrom, the nanocarriers can be loaded with proteins, peptides, carbohydrates, polysaccharides, nucleic acid molecules, organic molecules, diagnostic active agents, or combinations thereof for treating or diagnosing cancer.

In some embodiments, the active agent is a therapeutic drug. The majority of chemotherapeutic drugs can be divided into alkylating agents, antimetabolites, anthracyclines, plant alkaloids, topoisomerase inhibitors, monoclonal antibodies, and other antitumour agents.

Non-limiting examples of antineoplastic drugs that damage DNA or inhibit DNA repair include carboplatin, carmustine, chlorambucil, cisplatin, cyclophosphamide, dacarbazine, daunorubicin, doxorubicin, epirubicin, idarubicin, ifosfamide, lomustine, mechlorethamine, mitoxantrone, oxaliplatin, procarbazine, temozolomide, and valrubicin. In some embodiments, the antineoplastic drug is temozolomide, which is a DNA damaging alkylating agent commonly used against glioblastomas. In some embodiments, the antineoplastic drug is a PARP inhibitor, which inhibits a step in base excision repair of DNA damage. For example, the PARP inhibitor can be Olaparib ($C_{24}H_{23}FN_4O_3$).

In some embodiments, the antineoplastic drug is a histone deacetylase inhibitor, which suppresses DNA repair at the transcriptional level and disrupt chromatin structure. In some embodiments, the antineoplastic drug is a proteasome inhibitor, which suppresses DNA repair by disruption of ubiquitin metabolism in the cell. Ubiquitin is a signaling molecule that regulates DNA repair. In some embodiments, the antineoplastic drug is a kinase inhibitor, which suppresses DNA repair by altering DNA damage response signaling pathways.

Additional antineoplastic drugs include, but are not limited to, alkylating agents (such as temozolomide, cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil, gemcitabine, methotrexate, cytosine arabinoside, fludarabine, and floxuridine), some antimitotics, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide) and cytoskeletal targeting drugs such as paclitaxel.

In some embodiments the active agent is a radiosensitizer. Examples of known radiosensitizers include cisplatin, gemcitabine, 5-fluorouracil, pentoxifylline, vinorelbine, PARP inhibitors, histone deacetylase inhibitors, and proteasome inhibitors.

In some embodiments, the active agent(s) is paclitaxel, camptothecin and or a derivatives In some embodiments, the dose of active agent can be reduced by 10%, 15%, 20%, 25%, 30%, 35%, 40%, 45%, 50%, 60%, 70, 80% or more when administered in the disclosed nanocarriers relative to free drug.

c. Combination Therapy

The disclosed compositions can be used in combination with standard chemotherapy, radiation therapy, and other anti-cancer treatments. Radiation therapy (a.k.a. radiotherapy) is the medical use of ionizing radiation as part of cancer treatment to control malignant cells. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. In some embodiments, the disclosed antigen binding molecules are used to increase radiosensitivity for a non-malignant condition.

Radiation therapy works by damaging the DNA of dividing cells, e.g., cancer cells. This DNA damage is caused by one of two types of energy, photon or charged particle. This damage is either direct or indirect. Indirect ionization happens as a result of the ionization of water, forming free radicals, notably hydroxyl radicals, which then damage the DNA. For example, most of the radiation effect caused by photon therapy is through free radicals. One of the major limitations of photon radiotherapy is that the cells of solid tumors become deficient in oxygen, and tumor cells in a hypoxic environment may be as much as 2 to 3 times more resistant to radiation damage than those in a normal oxygen environment.

Direct damage to cancer cell DNA occurs through high-LET (linear energy transfer) charged particles such as proton, boron, carbon or neon ions. This damage is independent of tumor oxygen supply because these particles act mostly via direct energy transfer usually causing double-stranded DNA breaks. Due to their relatively large mass, protons and other charged particles have little lateral side scatter in the tissue; the beam does not broaden much, stays focused on the tumor shape and delivers small dose side-effects to surrounding tissue. The amount of radiation used in photon radiation therapy is measured in Gray (Gy), and varies depending on the type and stage of cancer being treated. For curative cases, the typical dose for a solid epithelial tumor ranges from 60 to 70 Gy, while lymphomas are treated with lower doses. Post-operative (adjuvant) doses are typically around 45-60 Gy in 1.8-2 Gy fractions (for breast, head, and neck cancers). Many other factors are considered by radiation oncologists when selecting a dose, including whether the patient is receiving chemotherapy, patient co-morbidities, whether radiation therapy is being administered before or after surgery, and the degree of success of surgery.

The response of a cancer to radiation is described by its radiosensitivity. Highly radiosensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radioresistant, that is, much higher doses are required to produce a radical cure than may be safe in clinical practice. Renal cell cancer and melanoma are generally considered to be radioresistant.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radiotherapy. A third technique is to enhance the radiosensitivity of the cancer by giving certain drugs during a course of radiotherapy. In some embodiments, the disclosed compositions can accomplish techniques two, three, or a combination thereof 2. Ischemia In some embodiments, the compositions are used to target therapeutic agents to sites of ischemia. Ischemia is a vascular condition involving an interruption in the arterial blood supply to a tissue, organ, or extremity that, if untreated, can lead to tissue death. Thus ischemia can induce necrosis that leads to the accumulation of extracellular DNA. It can be caused by embolism, thrombosis of an atherosclerosis artery, or trauma. Venous problems like venous outflow obstruction and low-flow states can cause acute arterial ischemia. An aneurysm is one of the most frequent causes of acute arterial ischemia. Other causes are heart conditions including myocardial infarction, mitral valve disease, chronic atrial fibrillation, cardiomyopathies, and prosthesis, in all of which thrombi are prone to develop. Common types of ischemia include, for example, large and small bowel ischemia which can include ischemic colitis, acute and chronic brain ischemia which can include transient ischemic attack or a stroke, limb ischemia including acute limb ischemia, and cutaneous inschemia.

In some embodiments for treating ischemia the disclosed nanocarriers are loaded with an active agent that increases blood flow, reduces coagulation (e.g., with anticoagulants such as heparin), induces arterial dilation, or induces or increases thrombolysis (e.g., with recombinant tissue plasminogen activator (rtPA), streptokinase, urokinase, etc.), or agents that protect and/or promote survival of cells in the region of ischemia (such as cytoprotective proteins including heat shock proteins). In some embodiments, the dose of active agent can be reduced by 10%, 15%, 20%, 25%, 30%, 35%, 40%, 45%, 50%, 60%, 70, 80% or more when administered in the disclosed nanocarriers relative to free drug.

In some embodiments, the composition one that enhances survival of brain cells such as neurons.

In some embodiments, the nanocarrier is microbubbles. For example, microbubbles can be a therapeutic device for vehiculating oxygen to hypoxic tissues. They can show proper permeability and diffusivity properties and can be non-toxic. See, for example, Bisazza, et al., *Engineering in Medicine and Biology Society*, 2008. EMBS 2008. 30th Annual International Conference of the IEEE (20-25 Aug. 2008), 10.1109/IEMBS.2008.4649599, which describes chitosan-coated oxygen microbubbles of average diameter 2.5 µm, which efficiently delivered oxygen both in 'in vitro' and 'in vivo' preparations, and can be conveniently metabolized, reversing the cellular hypoxic response. See also U.S. Pat. No. 9,107,950 and WO 2009/043031. Microbubbles, including oxygen-loaded microbubbles, can be targeted to tissue of interest, such as hypoxic tissue, using the disclosed targeting antibodies. Compositions and methods for modifying microbubbles to include a targeting moiety are known in the art, see, for example, Yeh, et al, "A Targeting Microbubble for Ultrasound Molecular Imaging," *PLoS ONE*, 10(7): e0129681. doi:10.1371/journal.pone.0129681 (2015).

3. Injury

The disclosed compositions can be used to treat an injury. An injury can be generally defined as damage to the body, which can be caused by, for example, accidents, falls, hits, weapons, etc. Injuries include wounds, brain injuries, nerve injuries, and soft tissue injuries. Injury can be to any part of the body, for example, the head, neck, throat, back, eye, nose, throat, chest, foot, toe, hand, finger, knee, elbow, etc. The injury can be any organ or tissue of the body, for example, the kidney, liver, spinal cord, muscle, bone, etc. An example of an injury to an organ is cardiac ischemic injury.

In some embodiments, the compositions are used to deliver active agents for the treatment of acute, chronic, or infected wounds. Wound healing involves a complex interaction between epidermal and dermal cells, the extracellular matrix, controlled angiogenesis, and plasma derived proteins, all coordinated by an array of cytokines and growth factors. This dynamic process has been classically divided into several overlapping phases: inflammation, proliferation, migration and remodeling.

Representative chronic non-healing wounds that can be treated include, but are not limited to, diabetic ulcers, arterial ulcers, venous ulcers, pressure (decubitus) ulcers and burns. Acute wounds include those that accompany injury or surgery. Bacterial biofilms can impair cutaneous wound healing and reduce topical antibacterial efficiency in healing or treating infected skin wounds. Biofilm bacteria are less susceptible to our immune defense system, and consequently, a biofilm-associated infection can persist for a long period of time (i.e., progress from an acute to a chronic infection).

In some embodiments, the subject has an inflammatory disease. For example, the inflammatory disease can be the result of harmful stimuli, such as pathogens, damaged cells, or irritants. The inflammatory disease can also be the result of hypersensitivity or autoimmunity.

The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. Examples of disorders associated with inflammation include: acne vulgaris, asthma, atherosclerosis, autoimmune diseases, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, and interstitial cystitis.

The active agent used to treat the injury can be selected based on the injury but can include analgesics, anesthetics, anti-inflammatories, anti-infectives, cytokines, chemokines, immunomodulators, other agents that promote healing, and agents that protect and/or promote survival of cells in the region of injury (such as cytoprotective proteins including heat shock proteins). In some embodiments, the dose of active agent can be reduced by 10%, 15%, 20%, 25%, 30%, 35%, 40%, 45%, 50%, 60%, 70, 80% or more when administered in the disclosed nanocarriers relative to free drug 4. Infection a. Infections to be Treated Extracellular DNA can also be found in areas of infection. Thus the disclosed compositions and methods can be used to treat infections in a subject in need thereof. In a mature animal, the immune system usually prevents or eliminates infections, but in some cases invading organisms, such as bacteria, viruses, fungi, parasites, can establish themselves in an organism and cause an infection that may cause significant symptoms and be life-threatening. Sites of infection are associated with increased amounts of extracellular DNA due to release from cell lysis, neutrophil lysis, and neutrophil extracellular traps (NETs) (Okshevsky et al., *Curr Opin Biotech*, 2015, 33:73-80) (Whitchurch et al., Science, 2002, 295: 1487) (Allesen-Holm et al., Mol Biol 2006, 59: 1114-1128) and therefore can be targeted using the compositions and methods disclosed herein.

The compositions and methods described herein are useful for treating subjects having infections by delaying or inhibiting the progression of an infection in a subject, reducing and/or eradicating the infection, and/or inhibiting or reducing symptoms associated with the infection, and/or reducing the dosage of other anti-infective agents required to eradicate the infection.

The types of infections that can be treated with the provided compositions and methods include, but are not limited to, bacterial, viral, fungal, and parasitic infections.

b. Exemplary Active Agents for Infection Treatment

In addition or alternative to 3E10 antibody or a fragment or fusion protein derived therefrom, the nanocarriers can be loaded with proteins, peptides, antibodies, carbohydrates, polysaccharides, nucleic acid molecules, organic molecules, diagnostic active agents, or combinations thereof for treating or diagnosing infection.

In some embodiments, the active agent is a therapeutic drug. Non-limiting examples of anti-infective drugs include antibiotics, antivirals, antiparasitic drugs.

In some embodiments, the dose of active agent can be reduced by 10%, 15%, 20%, 25%, 30%, 35%, 40%, 45%, 50%, 60%, 70, 80% or more when administered in the disclosed nanocarriers relative to free drug.

5. Autoimmune and/or Genetic Diseases a. Diseases to be Treated

Some autoimmune and/or genetic diseases are characterized by the development of damaged tissues that release DNA. The disclosed compositions and methods can be used to target delivery of nanomaterials to sites of tissue damage in autoimmune and/or genetic diseases.

The compositions and methods described herein are useful for treating subjects having autoimmune and/or genetic diseases by delaying or inhibiting the progression of an tissue damage in a subject, reducing and/or eradicating the severity of the disease, and/or inhibiting or reducing symptoms associated with the disease, and/or reducing the dosage of other agents required to treat the disease.

The types of autoimmune or genetic diseases that can be treated with the provided compositions and methods include, but are not limited to: muscular dystrophies (including Duchenne muscular dystrophy and myotonic dystrophy), systemic lupus erythematosus, scleroderma, vasculitis syndromes, rheumatoid arthritis, lysosomal storage diseases (including Tay-Sachs disease and Gaucher disease), glycogen storage diseases (including Pompe disease and McArdle disease).

b. Exemplary Active Agents for Autoimmune and/or Genetic Disease Treatment

In addition or alternative to 3E10 antibody or a fragment or fusion protein derived therefrom, the nanocarriers can be loaded with proteins, peptides, antibodies, carbohydrates, polysaccharides, nucleic acid molecules, organic molecules, diagnostic active agents, or combinations thereof for treating or diagnosing autoimmune or genetic diseases.

In some embodiments, the active agent is a therapeutic drug. Non-limiting examples of agents to treat autoimmune and/or genetic diseases include immunosuppressive agents, protein replacements (such as dystrophin, utrophin, enzymes), analgesics, anesthetics, anti-inflammatories, anti-infectives, cytokines, chemokines, immunomodulators, and other agents that promote healing, or agents that protect and/or promote survival of cells in the region of damage (such as cytoprotective proteins including heat shock proteins).

In some embodiments, the dose of active agent can be reduced by 10%, 15%, 20%, 25%, 30%, 35%, 40%, 45%, 50%, 60%, 70, 80% or more when administered in the disclosed nanocarriers relative to free drug.

EXAMPLES

Example 1: Synthesis and Characterization of Nanoparticles with and without Surface Anti-DNA Autoantibody Materials and Methods Materials and Cell Culture All chemicals were purchased from Sigma-Aldrich unless otherwise noted. The mouse mammary tumor cell line 4T1 was obtained from American Type Culture Collection (ATCC) and cultured in DMEM medium (Invitrogen) supplemented with 10% fetal bovine serum (Invitrogen), 100 units/ml penicillin and 100 ug/ml streptomycin (Invitrogen), in a 37° C. incubator containing 5% CO2.

Synthesis of PLGA-PLL

PLGA-PLL was synthesized according to previously reported procedures (Zhou, et al., *Biomaterials*, 33(2):583-591 (2012), Han, et al., *Nanomedicine* (2016)). Briefly, PLGA (3 g, 50:50 PLGA Acid End Group; i.v. ~0.67 dL/g; Absorbable Polymers, AL) and 200 mg poly(ε-carbobenzoxyl-L-lysine) (PLL) (MW 1000-4000 Da, Sigma) were dissolved in 6 mL dimethlyformamide in a dry round-bottom flask under argon. Dicyclohexyl carbodiimide (58 mg) and 0.31 mg dimethylaminopyridine in 2 mL dimethlyformamide was added to the polymer solution and allowed to stir for 48 h. The reacted solution was diluted by the addition of chloroform and precipitated in methanol. The dried polymer was then re-dissolved in chloroform, precipitated in ether, and dried under vacuum for 24 h. To remove protection, dried protected product was dissolved in 10 mL hydrogen bromide, 30% wt in acetic acid and allowed to stir for 90 min for deprotection. The polymer was precipitated in ether and washed until the product changed from a yellow to an off-white appearance. The product was then dissolved in chloroform and precipitated in ether. The polymer was vacuum dried for 24 h to remove all traces of ether. Samples before and after deprotection were collected to confirm modification of the polymer and subsequent removal of protecting carbobenzoxyl groups. The samples were dissolved in trifluoroethanol and evaluated from 200 to 350 nm using spectroscopy (Cary 50 Bio UV-Vis Spectrophotometer, Varian, Palo Alto, Calif.).

$3E10^{EN}$ Production and Thiolation

3E10 (D31N) di-scFv (referred to as $3E10^{EN}$ in this study) was produced in and purified from *P. pastoris* as previously described and illustrated below (SEQ ID NO:12) (Noble, et al., *Cancer Research*, 2015; 75(11):2285-2291). Purity and identity of the $3E10^{EN}$ isolated from *P. pastoris* supernatant was confirmed by SDS-PAGE and anti-Myc Western blot prior to conjugation to nanoparticles. Thiolation of $3E10^{EN}$ antibody was performed using Traut's agent. Briefly, 54 uL 3E10 solution (5 mg/ml) and 18 uL Traut's agent solution (10 mg/ml) were added to 1 ml PBS (pH 8.0 with 5 mM EDTA). The thiolation process took 1 hour by rotating the mixed solution on a horizontal shaker at room temperature.

```
                                            (SEQ ID NO: 12)
 1         10        20        30        40        51
AGIHDIVLTQSPASLAVSLGQRATISCRASKSVSTSSYSYMHWYQQKPGQP 61        71        81        91       101
PKLLIKYASYLESGVPARFSGSGSGTDFTLNIHPVEEEDAATYYCQHSRE 111       121       131       141       151
FPWTFGGGTKLEIKRADAAPGGGGSGGGGSGGGGSEVQLVESGGGLVKPG 161       171       181       191       201
GSRKLSCAASGFTFSNYGMHWVRQAPEKGLEWVAYISSGSSTIYYADTVK 211       221       231       241       251
GRFTISRDNAKNTLFLQMTSLRSEDTAMYYCARRGLLLDYWGQGTTLTVS 261       271       281       291       302
SASTKGPSVFPLAPLESSGSDIVLTQSPASLAVSLGQRATISCRASKSVST 312       322       332       342       352
SSYSYMHWYQQKPGQPPKLLIKYASYLESGVPARFSGSGSGTDFTLNIHP 362       372       382       392       402
VEEEDAATYYCQHSREFPWTFGGGTKLEIKRADAAPGGGGSGGGGSGGGG
```

-continued

```
            412        422        432        442        452
SEVQLVESGGGLVKPGGSRKLSCAASGFTFSNYGMHWVRQAPEKGLEWVA 462        472        482        492        502
YISSGSSTIYYADTVKGRFTISRDNAKNTLFLQMTSLRSEDTAMYYCARR 512        522        532
GLLLDYWGQGTTLTVSSLEQKLISEEDLNSAVDHHHHHH.
```

Nanoparticles Synthesis

To produce DOX for nanoparticle synthesis, the hydrochloride groups in commercial DOX hydrochloride (Sigma) were removed through titration using triethylamine in dichloromethane, resulting in DOX soluble in organic solvents. DOX-loaded nanoparticles were synthesized according to the standard single emulsion procedure. For synthesis of DOX-NPs, 50 mg PLGA-PLL and 6.7 mg doxorubicin were dissolved in 2 mL ethyl acetate. The solution was then added dropwise to a solution of 2 ml 2.5% polyvinyl alcohol (PVA). The resulting emulsion was sonicated on ice 3 times for 10 seconds each. The emulsion was then poured into a beaker containing aqueous 0.3% (v/v) PVA and stirred at room temperature overnight to allow the EA to evaporate and the particles to harden. Particles were collected by centrifugation at 18000 rpm, 30 min, washed twice with water, frozen, and lyophilized. For synthesis of 3E10/DOX-NPs, the same emulsion procedures were used. After overnight evaporation, nanoparticles were collected and re-suspended in PBS containing NHS-PEG5000-Mal (8 mg, JenKem Technology). After a 30 minute reaction, extra NHS-PEG5000-Mal was removed by centrifuge (18000 rpm, 30 min). PEGylated nanoparticles were then re-suspended in PBS containing thiolated 3E10 (270 ug). Sixty minutes later, nanoparticles were collected by centrifugation at 18000 rpm, 30 min, washed twice with water, frozen, and lyophilized. Naked NPs and 3E10-NPs were synthesized according to the same procedures but without DOX/3E10 and DOX, respectively.

Characterization of Nanoparticle Size and Morphology

The morphology and size of nanoparticles was characterized by Scanning electron microscopy (SEM). Briefly, dry nanoparticles were mounted on carbon tape and sputter-coated with gold in an argon atmosphere using a sputter current of 40 mA (Dynavac Mini Coater, Dynavac, USA). SEM analysis was carried out with a Philips XL30 SEM using a LaB electron gun with an accelerating voltage of 3 kV. The hydrodynamic diameter of nanoparticles was measured using Dynamic Light Scattering (DLS). A transparent cuvette was filled with 0.25 mg mL-1 nanoparticles in HPLC-grade water. The capped cuvette was placed in a Zetasizer (Malvern) and dynamic light scattering data was read. Zeta potential was also measured using the Zetasizer.

Characterization of Conjugation Efficiency

Ten mg 3E10 nanoparticles was dissolved in 100 uL DMSO and added to 900 uL ddH2O to make a final concentration 10 mg/ml. The amount of 3E10 in the solution was determined by the standard BCA assay (Thermo Scientific). Nanoparticles without 3E10 processed using the same procedures were used as a control.

Characterization of Drug Encapsulation

To determine the drug encapsulation efficiency (EE) and loading efficiency (LE), 1 mg of DOX-loaded nanoparticles were dissolved in 100 uL DMSO and added to 900 uL ddH2O to make a final concentration of 1 mg/ml. Nanoparticle solution was then spun briefly at 13,000 rpm and 100 uL supernatant was transferred to a microplate (BioTek). The fluorescence intensity was measured at 470 nm/590 nm (Ex/Em) and the concentration of DOX was calculated according to a standard curve of free DOX.

$$\text{Encapsulation Efficiency }(EE) = \frac{\text{Released } Dox \text{ Amount (mg)}}{\text{Total } Dox \text{ Amount (mg)}} \times 100\%$$

$$\text{Loading Efficiency}(EE) = \frac{\text{Released } Dox \text{ Amount (mg)}}{\text{Particles Amount (mg)}} \times 100\%$$

Control Release of DOX

DOX-loaded nanoparticles were re-suspended in PBS containing 0.02% sodium azide at 1 mg/ml in an Eppendorf tube and rotated in a low-speed shaker at room temperature. Release of DOX was monitored at several time intervals over 14 days. At each sampling time, the nanoparticle suspension was centrifuged for 10 min at 13,000 rpm. The supernatant was removed for quantification of DOX and an equal volume of PBS was replaced for continued monitoring of release. Detection of DOX was performed using the same methods as described above.

Cytotoxicity Evaluation

4T1 cells were plated in a 96-well cell culture plate at a concentration of $2\times10^3$ per well and incubated with concentrations of nanoparticles ranging from 1.25 to 500 ug/mL. The same amounts of free DOX were added to parallel wells as controls. Three days after treatment, the effect of treatments on cell proliferation was determined using the standard MTT assay.

Results

A strategy was developed for autocatalytic, tumor-targeted delivery of nanoparticles by $3E10^{EN}$. PLGA nanoparticles with surface conjugation of $3E10^{EN}$ were developed for exDNA targeting and with internal encapsulated DOX for chemotherapy and exDNA release. $3E10^{EN}$ has the ability to home nanoparticles to tumors, which contain a greater amount of exDNA than healthy tissue. The concentration of exDNA in tumor environments can increase with time and delivery of cytotoxic therapy. Thereby, the efficiency of nanoparticle accumulation in tumors autocatalytically increases with time and subsequent treatments.

In order to avoid potential nonspecific toxicity secondary to Fc-mediated activation of complement or antibody-dependent cell-mediated cytotoxicity, 3E10 fragments lacking an Fc region have recently been generated and tested. One of the most promising variants of these fragments is an enhanced di-single chain variable fragment of 3E10 that has been mutated to improve its binding affinity for DNA (Noble, et al., *Cancer Research*, 2015; 75(11):2285-2291). 3E10 (D31N) di-scFv was chosen for testing in the present study and it is hereafter referred to as $3E10^{EN}$ (EN=enhanced). To test the ability of $3E10^{EN}$ to autocatalytically deliver nanoparticles to tumors DOX-loaded PLGA nanoparticles with surface-conjugated $3E10^{EN}$ ($3E10^{EN}$/DOX-NPs) were synthesized. PLGA was first conjugated with poly(L-lysine) (PLL) and the resulting PLGA-PLL, which contains lysine groups for surface functionalization, was used as the starting material. To enable efficient encapsulation, the hydrochloride group in commercial DOX hydrochloride was removed through titration using triethylamine in dichloromethane. Nanoparticles were synthesized through the standard single emulsion procedure and further modified with NHS-PEG-Mal to display maleimide groups for conjugation of thiolated $3E10^{EN}$. Controls included nanoparticles without surface conjugated $3E10^{EN}$ (DOX-NPs), nanoparticles with $3E10^{EN}$ but without DOX ($3E10^{EN}$-NPs), and nanoparticles without $3E10^{EN}$ or DOX (naked NPs) and were synthesized using the same procedures but without 3E10$^{EN}$ conjugation, DOX encapsulation, or both. Scanning electron microscopy (SEM) showed that all nanoparticles were spherical and in size of 86-107 nm (Table 1). The hydrodynamic diameters of nanoparticles of different formulation were in the range of 180-210 nm (FIG. 1A). The conjugation of 3E10$^{EN}$ slightly increased nanoparticle size. An average of 5 3E10$^{EN}$ molecules were conjugated to the surface of each nanoparticle. DOX was encapsulated with 6.0% by weight (Table 1). Zeta potentials of the different NPs were also measured. PLGA NPs with PLL were found to have a neutral surface charge, whereas conjugation of 3E10$^{EN}$ decreased the surface charge to −8 (Table 1).

Figure 1B:
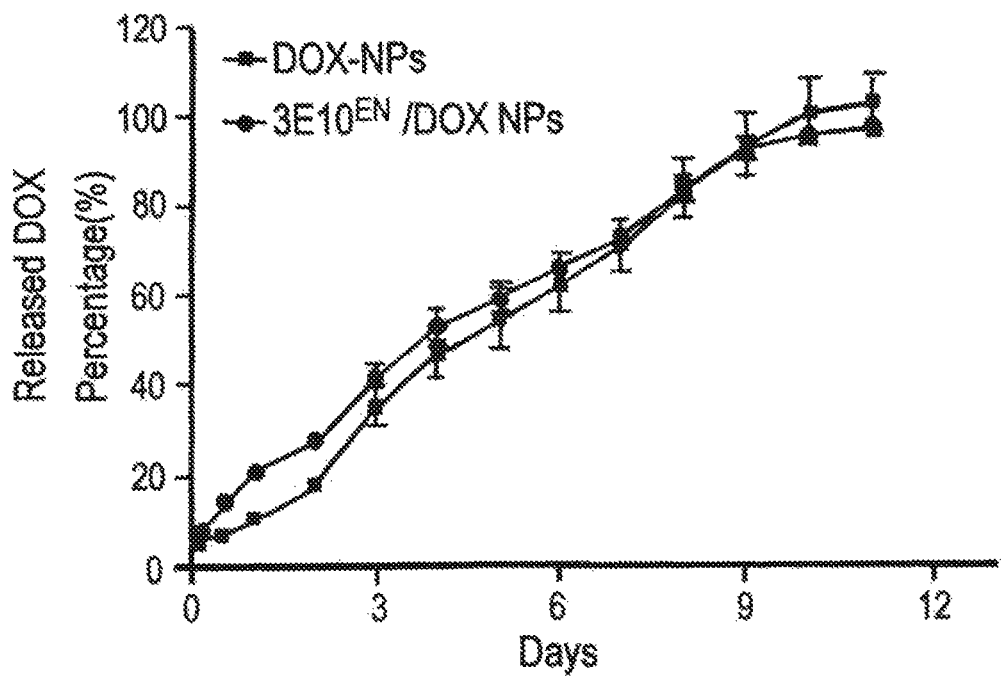
FIG. 1B is a line graph showing controlled DOX release profiles of DOX-NPs and $3E10^{EN}$/DOX-NPs.
Figure 1C:
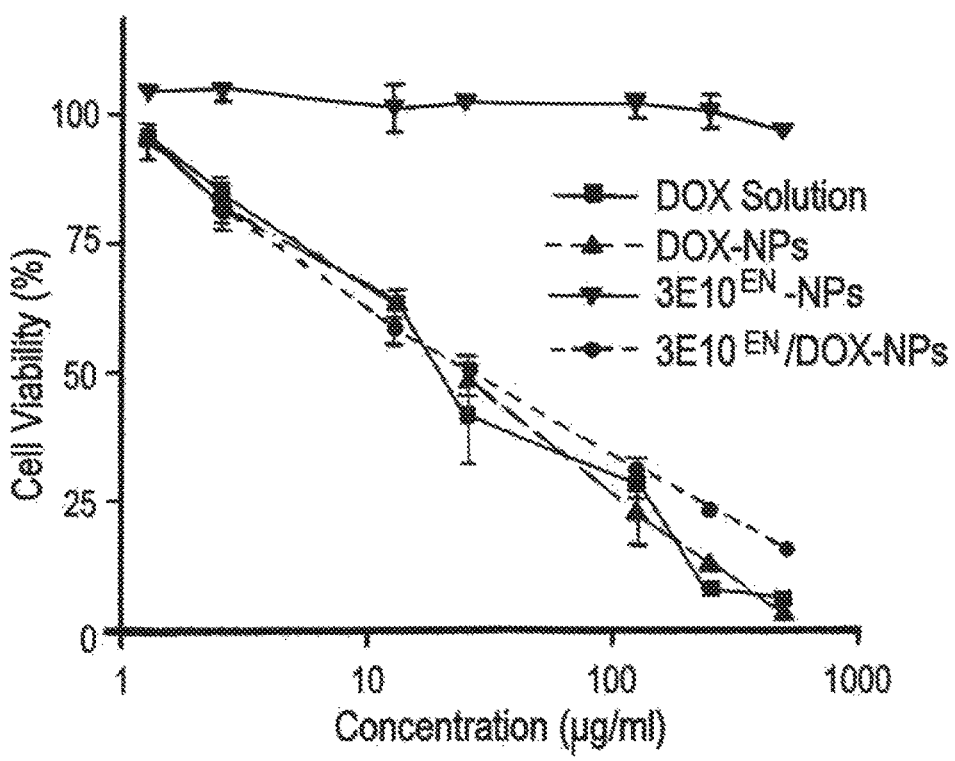
FIG. 1C is a line graph showing the effects of nanoparticles on the viability of 4T1 murine breast cancer cells. The cells were treated for three days with DOX alone, DOX-NPs, $3E10^{EN}$-NPs, or $3E10^{EN}$/DOX-NPs and then survival was evaluated by MTT assay. Percent cell viability is shown.

The release of DOX from 3E10$^{EN}$/DOX-NPs and DOX-NPs were compared to determine if 3E10$^{EN}$ interfered in any way with drug release. As shown in FIG. 1B, DOX was released in an equivalent controlled manner over 12 days from both 3E10$^{EN}$/DOX-NPs and DOX-NPs, indicating that 3E10$^{EN}$ did not interfere with drug release. Next, the nanoparticles were tested for effects on the viability of 4T1 murine breast cancer cells. The cells were treated for three days with DOX alone, DOX-NPs, 3E10$^{EN}$-NPs, or 3E10$^{EN}$/DOX-NPs and then survival was evaluated by MTT assay. Free DOX, DOX-NPs, and 3E10$^{EN}$/DOX-NPs all yielded comparable inhibition of cells, while the 3E10$^{EN}$-NPs without DOX were not significantly toxic to the cells (FIG. 1C). The characteristics of the nanoparticles used in this study are summarized in Table 1.

droxysuccinimide (NHS, 0.17 mg, 1.5 umol) and reacted with NH2-PEG50-NH2 (0.41 mg, 3.0 umol). DNA terminated with amine groups was then thiolated with Traut's Reagent (0.68 mg, 5.0 umol) and coated to a glass plate surface functionalized with maleimide groups (MicroSurfaes, Inc). To determine the binding ability of nanoparticles, IR780-loaded nanoparticles with and without 3E10$^{EN}$ were re-suspended in PBS at 1 mg/ml and added to the glass plate surface. After 1 hour incubation at room temperature, the glass plate was rinsed with water. Nanoparticles attached on glass plate were detected at 745 nm/800 nm (Ex/Em) using an in vivo imaging system (IVIS) system (Xenogen).

Statistical Analysis

Data were taken in triplicates and reported as a mean and standard deviation. Comparison of the DNA binding ability of nanoparticles, the amount of exDNA in tissues, and the nanoparticle delivery efficiency between two conditions was evaluated by a paired Student's t-test. One-way ANOVA analysis was performed to determine the statistical significance of treatment related changes in tumor volume. A $p<0.05$ was considered to indicate a statistically significant difference.

Results

3E10 has a high affinity with DNA (Service, et al., *Science*, 330(6002):314-315 (2010), Swystun, et al., *J Thromb Haemost*, 9(11):2313-2321 (2011)). Experiments were designed to determine if surface-conjugated 3E10$^{EN}$ would enhance the interaction of nanoparticles with DNA. To test this, a glass slide was coated with linearized plasmid

TABLE 1

Characteristics of the Nanoparticles

| | Size (nm) | Hydrodynamic diameter (nm) | Zeta (mV) | PEG per NP | 3E10 per NP | DOX (%, wt) |
|---|---|---|---|---|---|---|
| Naked NPs | 86.5 | 186.9 | 0.1 | | n/a | n/a |
| 3E10$^{EN}$-NPs | 105.3 | 211.4 | −8.2 | 9.600 | 5.1 | n/a |
| DOX-NPs | 92.3 | 184.6 | 0.1 | | n/a | 6.3 |
| 3E10$^{EN}$/DOX-NPs | 107.5 | 216.7 | −7.9 | | 5.1 | 6.0 |

These results are of particular interest because, although the amount of DOX released from the NPs during the treatment period was approximately 40% of the amount of drug to which cells were exposed in the group that received treatment with free DOX, the DOX-NPs and free DOX had a similar effect on cell viability. Similar are discussed in (Park, et al., *Nanomed-Nanotechnol.* 2009, 5:410-418; Lei, et al., *Ifmbe Proc.* 2010, 32:224-227; Zhou, et al., *Proc Natl Acad Sci USA.*, 2013, 110:11751-11756; Liu, et al., *Biomaterials.* 2009; 30:5707-5719; and Han, et al., *ACS nano.* 2016, 10:4209-4218) and this effect is likely due to differences between the mechanisms governing cellular uptake and export of nanoparticles and free drugs. For example, free DOX, but not DOX-loaded nanoparticles, is a substrate of ATP-binding cassette (ABC) transporters highly expressed in tumor cells.

Figure 2:
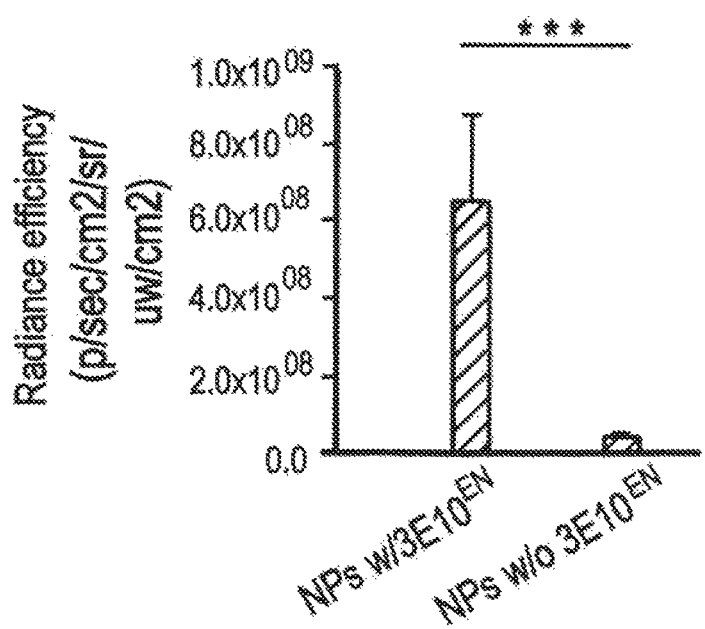
FIG. 2 is a bar graph showing quantitative analysis (fluorescence intensity) of nanoparticles binding to the A glass slide coated with linearized plasmid DNA was incubated with nanoparticles with or without surface $3E10^{EN}$. For the purpose of detection the nanoparticles were encapsulated with IR780. After a 60-minute incubation with the nanoparticles the slide was rinsed and the signal of IR780, which correlated with the amount of nanoparticles, was visualized by IVIS® Imaging System. ***: P<0.001

Example 2: 3E10$^{EN}$-Conjugation Enhances the Interaction of Nanoparticles with exDNA Materials and Methods DNA Binding Ability of 3E10-Conjugated Nanoparticles Plasmid DNA pGL4.74 (20 ug, Promega) was linearized using BamHI to expose phosphate groups, which was next activated by N-(3-Dimethylaminopropyl)-N'-ethylcarbodiimide hydrochloride (EDC, 0.20 mg, 1.0 umol) and N-Hy- DNA and incubated with nanoparticles with and without surface 3E10$^{EN}$. For the purpose of detection the nanoparticles were encapsulated with IR780, a near-infrared fluorescent dye. After a 60-minute incubation with the nanoparticles the slide was rinsed and the signal of IR780, which correlated with the amount of nanoparticles, was visualized by IVIS. The signal was quantified in FIG. 2. Conjugation of 3E10$^{EN}$ increased the association of nanoparticles with the DNA-coated glass surface by 5.6 fold, confirming that 3E10$^{EN}$-NPs are attracted to DNA as expected.

Example 3: exDNA is Enriched in 4T1 Tumors and Increases with 3E10$^{EN}$/DOX-NP Treatment Materials and Methods Measurement of exDNA in Tumors and Health Tissues Tumors were excised from mice with or without treatment of 3E10/DOX-NPs. The livers, hearts and muscles harvested from healthy mice without tumors were used as controls. Tumors and control healthy tissues were sliced in a similar size, mounted to a slide, and stained with Picogreen (ThermoFisher Scientific). Five minutes later, the slide was rinsed with water. The fluorescence intensity was detected at 465 nm/520 nm (Ex/Em) by the IVIS.

Results

Figure 3:
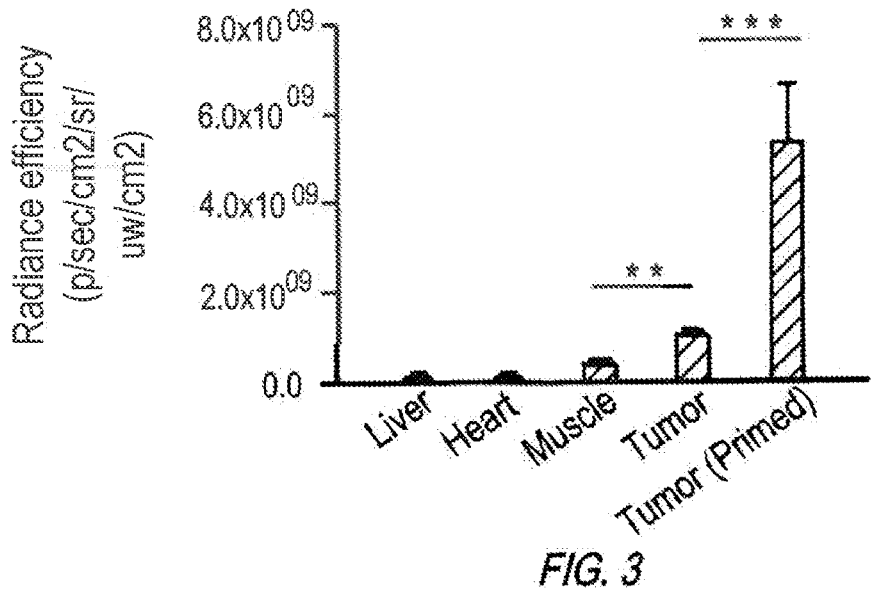
FIG. 3 is a bar graph showing the relative amounts (fluorescence intensity) of exDNA in normal tissues and 4T1 tumors with and without treatment with $3E10^{EN}$/DOX-NPs as determined by Picogreen staining. The amount of exDNA in untreated tumors was 7.5, 11.7 and 2.5 times greater than what is found in the liver, heart, and muscle. Treatment of the mice with $3E10^{EN}$/DOX-NPs increased the amount of exDNA in tumors by 5.1 fold compared to tumors in untreated mice. exDNA present in the indicated tissues (n=5) is presented as mean+/−SD. : P<0.01. *: P<0.001.

The ability of 3E10$^{EN}$ to target nanoparticles to tumors was tested using the syngeneic 4T1 murine breast cancer mouse model. In this model 4T1 breast cancer xenografts were generated by subcutaneous injection in BALB/c mice. Prior to initiating efficacy studies, relative amounts of exDNA in normal tissues and 4T1 tumors were evaluated with and without treatment with 3E10$^{EN}$/DOX-NPs by Picogreen staining. Consistent with previous findings (Weisbart, et al., *Sci Rep.*, 5:12022 (2015), Stroun, et al., *Clin Chim Acta*, 313(1-2):139-142 (2001), Sueoka-Aragane, et al., *PloS One*, 9(12) (2014), Wen, et al., *Cancer Research*, 73(14):4256-4266 (2013)), the amount of exDNA in untreated tumors was 7.5, 11.7 and 2.5 times greater than what is found in the liver, heart, and muscle (FIG. 3), indicating exDNA as a viable target for preferential drug delivery to tumors in this model. The effect of treatment with 3E10$^{EN}$/DOX-NPs on the amount of exDNA was tested. Mice bearing 4T1 tumors were treated with intravenous injection of 3E10$^{EN}$/DOX-NPs on two consecutive days, and then on the third day the mice were sacrificed and tumor exDNA content was evaluated. As shown in FIG. 3, treatment of the mice with 3E10$^{EN}$/DOX-NPs increased the amount of exDNA in tumors by 5.1 fold compared to tumors in untreated mice. Taken together, these results confirmed that this mouse model was appropriate for testing the proposed autocatalytic delivery of nanoparticles to tumors using 3E10$^{EN}$ to target exDNA.

Example 4: 3E10$^{EN}$ Mediates Autocatalytic, Tumor-Targeted Delivery of Nanoparticles Materials and Methods
In Vivo Tumor Homing of Nanoparticles
Female BALB/c mice (Charles River Laboratories) were used for this study and maintained in a sterile environment. This project was approved by the Yale University Institutional Animal Care and Utilization Committee (IACUC). To establish tumors, mice received subcutaneous flank injections of 1×10$^6$ 4T1 tumor cells. Tumor size was measured weekly using traceable digital vernier calipers (Fisher). Tumor volume was determined by measuring the length (l) and width (w), and then calculating the volume (V) using the following formula: V=lw2/2. When the volume reaches ~200 mm3 (day1), mice were randomly divided into 3 groups. The first group was treated with 3E10$^{EN}$ conjugated nanoparticles without IR780 at day 1 and 2 and received a final injection of 3E10$^{EN}$ conjugated, IR780-loaded nanoparticles at day 3. The second and third groups received intravenous administration of IR780-loaded nanoparticles and 3E10$^{EN}$ conjugated, IR780-loaded nanoparticles at day 3. Nanoparticles were administered at 1 mg per mouse. The loadings of IR780 in IR780-loaded nanoparticles and 3E10 conjugated, IR780-loaded nanoparticles were comparable. On day 5, mice were euthanized and the tumors were harvested for imaging using the IVIS. After imaging, tumors were lyophilized and homogenized in DMSO. The amount of dye in tumors was extracted and quantified using a microplate (BioTek).

Blood Concentrations of DOX-NPs
Blood concentrations of DOX-NPs with and without conjugation of 3E10$^{EN}$ recorded as a function of time. To enable detection of NPs, NPs were co-loaded with 1% coumarin 6. Six BALB/c mice were randomly assigned to two groups, which received intravenous administration of 1 mg DOX-NPs with and without conjugation of 3E10$^{EN}$, respectively. At 5 min, 15 min, 30 min, 1 h, 2 h, 4 h, 6 h, 24 h, 36 h and 48 h post injection, 20 uL blood sample from each mouse was collected into a 1.5 mL Eppendorf tube and lyophilized. Then, 100 uL DMSO and 1 mL acetonitrile were added to each tube. After sonication in a water bath sonicator for 15 min, samples were subjected to centrifugation at 4000 rpm for 20 min to remove cellular fragments and blood albumin. Then, 0.8 ml supernatant from each sample was collected and added to an eppendorf tube. The acetonitrile was evaporated and the dye in the DMSO was quantified at Ex/Em 444/505 nm using a plate reader (BioTek ELx800).

Figure 4:
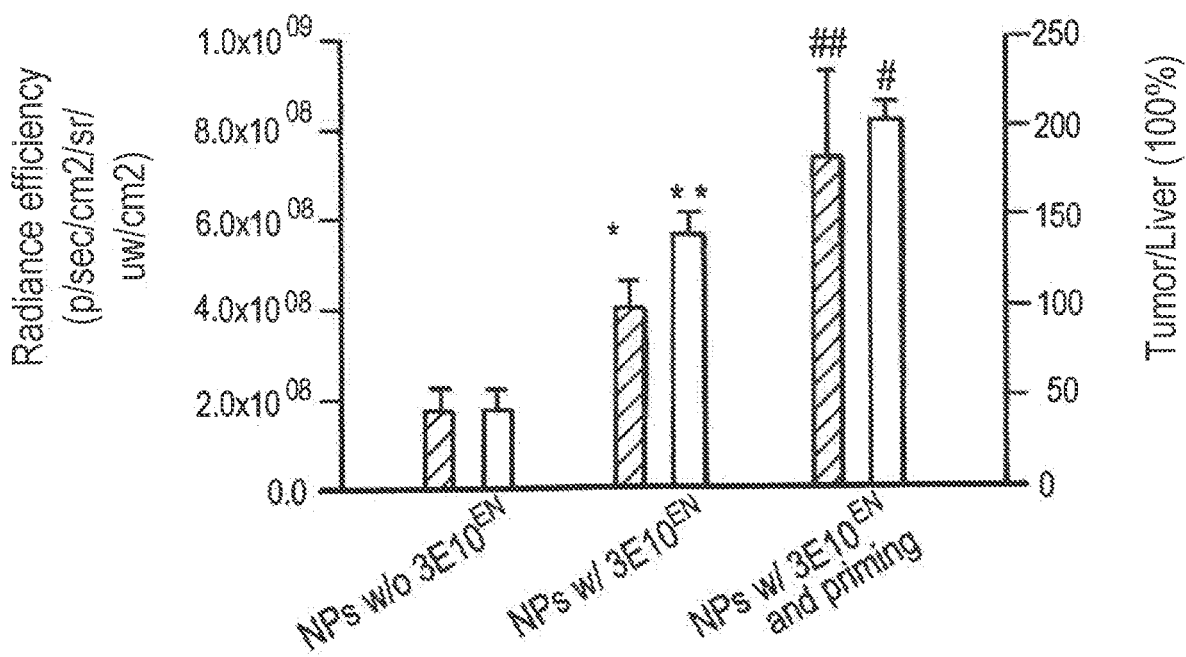
FIG. 4 is a bar graph showing fluorescence intensity of tumors excised from 4T1 tumor-bearing mice and imaged using an IVIS imaging system twenty-four hours after intravenous administration of IR780-loaded nanoparticles with or without $3E10^{EN}$ conjugation. The average amount of nanoparticles in tumors from mice that received priming treatments was 1.8 times greater than the amount in tumors from mice without priming. With priming, the accumulation of nanoparticles in tumors was 4.1 times higher than that in the liver, compared to 0.5 times for mice that received treatment with naked NPs. Quantitative analysis of the accumulation of indicated nanoparticles in tumors (n=4), where * and #represent statistical analyses between the NPs w/ 3E10 group and the NPs w/o 3E10 group, and between the NPs w/ 3E10 and priming group and the NPs w/ 3E10 group, respectively. * and #: P<0.05, ** and ##: P<0.01.
Figure 9:
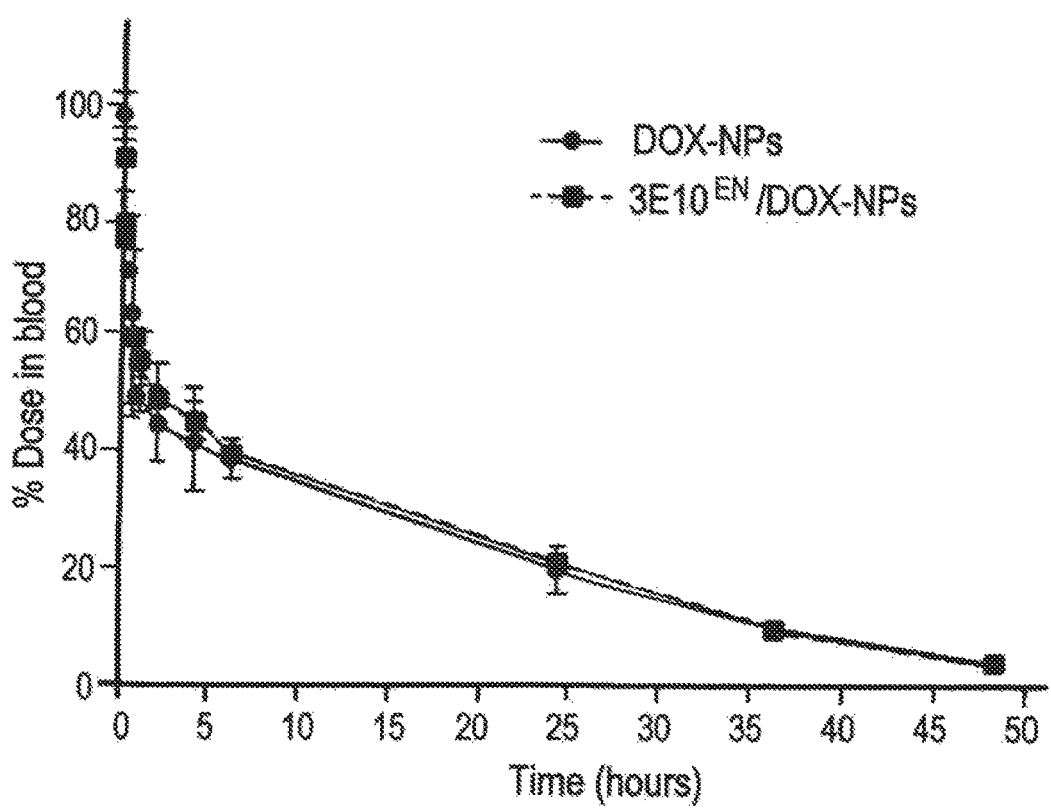
FIG. 9 is a line graph showing blood concentrations of DOX-NPs with and without conjugation of 3E10$^{EN}$ as a function of time.

Results
Experiments were designed to determine if 3E10$^{EN}$ can mediate preferential delivery of nanoparticles to tumors. IR780-loaded nanoparticles with or without 3E10$^{EN}$ conjugation were administered intravenously to 4T1 tumor-bearing mice. Twenty-four hours later, tumors were excised and imaged using an IVIS imaging system. Naked NPs were observed to localize into a range of tissues, with some tumor uptake but the greatest amount of uptake was seen in the liver. By contrast, 3E10$^{EN}$-conjugated NPs showed a pattern of preferential uptake into tumors rather than liver and a 2.3 fold increase in tumor localization compared to naked NPs (FIG. 4). These results indicate preferential targeting of nanoparticles to untreated tumors by 3E10$^{EN}$. 3E10$^{EN}$ did not alter the circulation life of NPs (FIG. 9), and therefore the enhanced uptake mediated by 3E10$^{EN}$ is believed to be due to interaction with exDNA in tumors. These results indicate preferential targeting of nanoparticles to untreated tumors by 3E10$^{EN}$.

According to the proposed strategy, the efficiency of 3E10$^{EN}$. mediated delivery would increase autocatalytically with time and delivery of treatments that induce release of tumor DNA and cause further accumulation of exDNA in the tumor environment. To test the strategy, 4T1 tumor-bearing mice were treated with 3E10$^{EN}$/DOX-NPs without IR780 daily for two consecutive days (referred to here as the priming treatments). On the third day, mice received a final injection of IR780-loaded 3E10$^{EN}$-NPs. Twenty-four hours later, tumors were excised and imaged. As shown in FIG. 4, the priming treatments with 3E10$^{EN}$/DOX-NPs significantly enhanced the tumor delivery of the nanoparticles. The average amount of nanoparticles in tumors from mice that received priming treatments was 1.8 times greater than the amount in tumors from mice without priming. Notably, with priming, the accumulation of nanoparticles in tumors was 4.1 times higher than that in the liver, compared to 0.5 times for mice that received treatment with naked NPs.

Example 5: 3E10$^{EN}$/DOX-NPs have a Significantly Greater Effect on Tumors than DOX-NPs or DOX Alone Materials and Methods
Antitumor Evaluation in Mouse Tumor Xenografts
Mice bearing 4T1 tumors were established as described above. When tumor volumes reached ~100 mm$^3$, mice were randomly divided into five groups, with seven mice per group, as follows: group 1 received treatment of PBS; group 2 received treatment of free DOX in PBS; group 3 received treatment of 3E10$^{EN}$-NPs; group 4 received treatment of DOX-NPs; and group 5 received treatment of 3E10$^{EN}$/DOX-NPs. Treatment was performed 3 times per week. Nanoparticles were administered at 1 mg, equal to 80 ug DOX per mouse. Tumor sizes were measured three times a week. Mice were euthanized when tumor volume reached 1000 mm$^3$, at which point the tumors were excised and fixed in formalin for immunohistochemistry. Serial sections were obtained and stained with hematoxylin and eosin (H&E) and Terminal Deoxynucleotidyl Transferase (TUNEL) for analysis of therapeutic effect. The growth curve was plotted using the mean of the tumor volumes for each treatment group, at each timepoint.

Results

Figure 5:
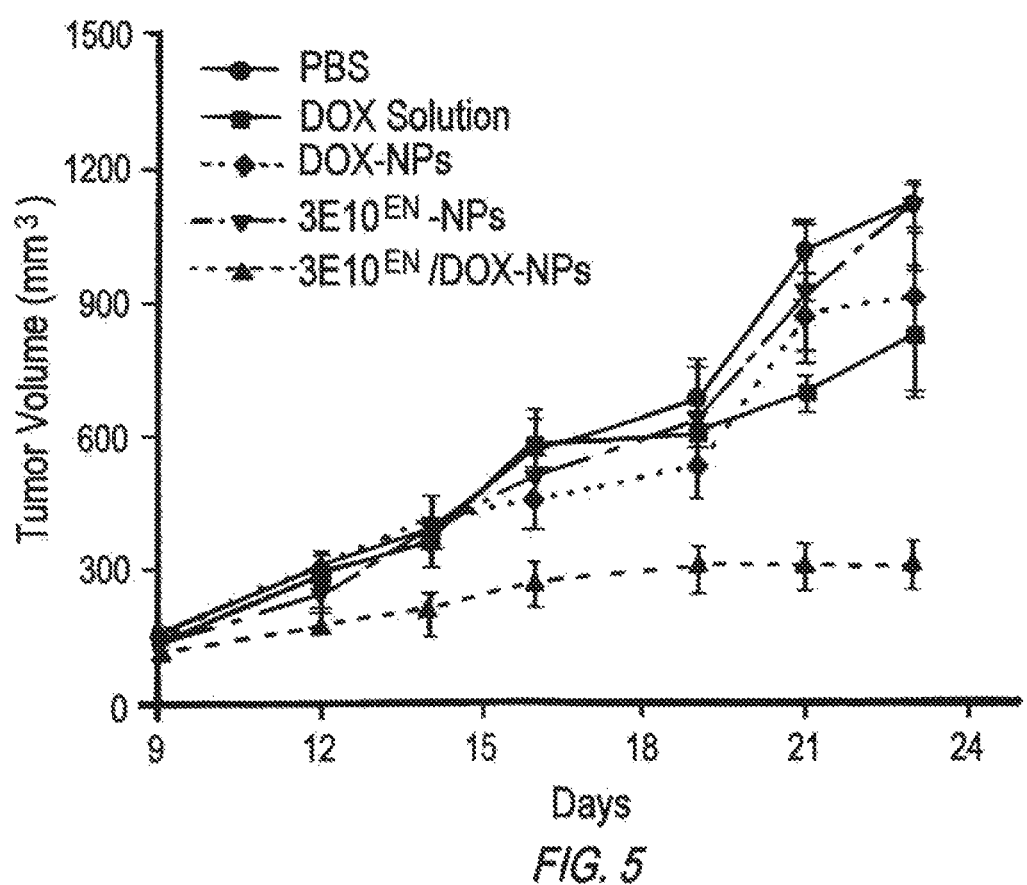
FIG. 5 is a tumor volume growth curve (Tumor Volume (mm³)) showing the effect of nanoparticles on 4T1 tumor growth. Mice bearing 4T1 tumors of ~100 mm³ size were treated three times a week with intravenous injection of control PBS, free DOX, DOX-NPs, 3E10$^{EN}$-NPs, or 3E10$^{EN}$/DOX-NPs (n=7 mice per group), and tumor volumes were measured three times a week and plotted as shown.

Lastly, experiments were designed to determine if the 3E10$^{EN}$-based approach to targeting exDNA for autocatalytic tumor-targeted drug delivery would result in improvements in tumor response to treatment in vivo. Mice bearing 4T1 tumors of ~100 mm$^3$ size were treated three times a week with intravenous injection of control PBS, free DOX, DOX-NPs, 3E10$^{EN}$-NPs, or 3E10$^{EN}$/DOX-NPs. Tumor volumes were measured three times a week, and the resulting growth curves are shown in FIG. 5. Of all of the treatment groups, only the 3E10$^{EN}$/DOX-NPs were observed to greatly inhibit tumor growth (p<0.01 compared to both free DOX and DOX-NPs). By the end of the study, compared to the control group with PBS treatment, treatments with free DOX or DOX-NPs reduced tumor volumes by only 26% and 19%, respectively. No significant difference was found between these two groups. By contrast, treatment with 3E10$^{EN}$/DOX-NPs reduced tumor volume by 72%. Histologically, tumors from control treatments revealed a highly cellular mass with prominent nuclei; in contrast, tumors from animals treated with 3E10$^{EN}$/DOX-NPs exhibited a much lower cellular mass, a lower nuclear-cytoplasmic ratio, and a marked increase in the number of apoptotic cells measured by TUNEL staining.

Example 6: 3E10$^{EN}$-NPs Localize into Melanoma Brain Tumors

Materials and Methods

Metastatic Melanoma Brain Tumor Localization Studies

Mice with intracranial tumors from a melanoma cancer cell line were treated with tail vein injection of either unconjugated NPs loaded with IR780 (control) or 3E10$^{EN}$-conjugated NPs loaded with IR780. 24 hours later the accumulation of NPs in the brain tumors was visualized by IVIS.

Results

Figure 6:
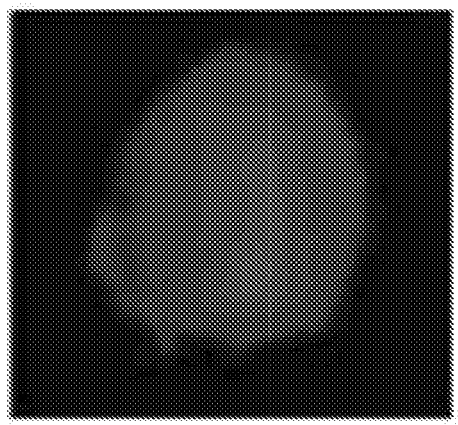
FIG. 6 is a pair of images of brains from mice with metastatic melanoma brain tumors that have been imaged by IVIS to detect IR780 signal in nanoparticles. The control mouse image is from a mouse that was treated with control nanoparticles that were loaded with IR780 but lack surface 3E10$^{EN}$. The 3E10$^{EN}$ image is from a mouse that was treated with nanoparticles loaded with IR780 and that have surface conjugated 3E10$^{EN}$.
Figure 6:
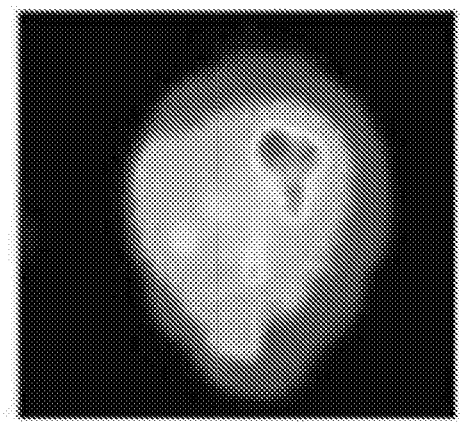

As shown in FIG. 6, no significant signal was detected in the brains of mice treated with control, but mice treated with 3E10$^{EN}$-NPs showed significant IR780 signal in the brain tumors, demonstrating effective delivery of NPs to the brain tumors by 3E10$^{EN}$.

Example 7: 3E10$^{EN}$-NPs Localize into Glioblastoma Brain Tumors

Materials and Methods

Glioblastoma Brain Tumor Localization Studies

Immunodeficient mice bearing orthotopic intracranial U87 glioblastoma tumors were treated with tail vein injections of control NPs or 3E10$^{EN}$-NPs. NPs were loaded with IR780 for detection. 24 hours after injection the accumulation of NPs in the glioblastoma brain tumors was visualized by IVIS.

Results

Figure 7:
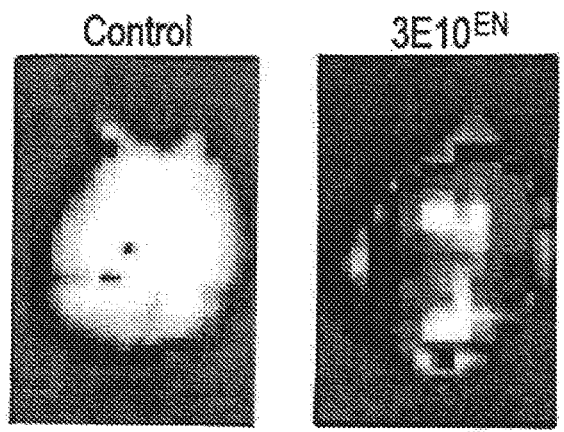
FIG. 7 is a pair of images of brains from mice with U87 glioblastoma brain tumors that have been imaged by IVIS to detect IR780 signal in nanoparticles. The control mouse image is from a mouse that was treated with control nanoparticles that were loaded with IR780 but lack surface 3E10$^{EN}$. The 3E10EN image is from a mouse that was treated with nanoparticles loaded with IR780 and that have surface conjugated 3E10$^{EN}$.

As shown in FIG. 7, no significant signal was detected in the brains of mice treated with control, but mice treated with 3E10$^{EN}$-NPs showed significant IR780 signal in the brain tumors. These data demonstrate effective delivery of NPs to brain tumors by 3E10$^{EN}$.

Example 8: 3E10$^{EN}$-NPs Localize into Ischemic Brain in Stroke

Materials and Methods

Stroke Volume Localization Studies

Stroke was induced in mice by middle cerebral artery occlusion. After indication of stroke mice were treated with tail vein injection of control NPs or 3E10$^{EN}$-NPs. NPs were loaded with IR780 for detection. At 24 hours after injection mice were analyzed for uptake of NPs into the region of stroke by IVIS.

Results

Figure 8:
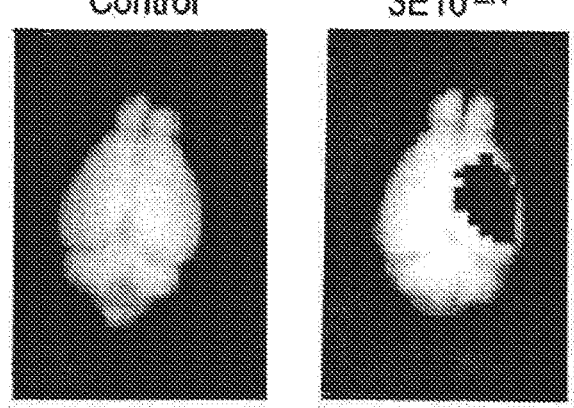
FIG. 8 is a pair of images of brains from mice with stroke induced by middle cerebral artery occlusion. The control mouse image is from a mouse that was treated with control nanoparticles that were loaded with IR780 but lack surface 3E10$^{EN}$. The 3E10$^{EN}$ image is from a mouse that was treated with nanoparticles loaded with IR780 and that have surface conjugated 3E10$^{EN}$.

As shown in FIG. 8, no significant signal was detected in the brain stroke volume of mice treated with control NPs, but mice treated with 3E10$^{EN}$-NPs showed significant IR780 signal in the region of stroke in the brain. These data demonstrate effective delivery of NPs to ischemic brain by 3E10$^{EN}$.

The Examples above demonstrate an autocatalytic tumor-targeting mechanism for systemic delivery of nanoparticles to tumors that takes advantage of exDNA in the tumor environment. 3E10$^{EN}$ was utilized as the targeting ligand for exDNA and DOX as the model drug, and the results show that 3E10$^{EN}$ mediates efficient delivery of nanoparticles to tumors and that this efficiency increases with subsequent treatments as more exDNA is released by the dying tumors. Compared to other targeting approaches that suffer from reduced efficiency over time as the relevant targets regress with treatment, the disclosed compositions and methods have the key advantage of improved efficiency with time and treatment due to increased release of exDNA into the target environment.

In addition to the above implications for delivery strategies in nanomedicine, the present work also reveals a new dimension of the potential for use of the lupus anti-DNA autoantibody 3E10 in molecular therapy techniques. 3E10 has the unusual ability to penetrate into the nuclei of living cells, and the antibody and its optimized fragments have previously been used to deliver therapeutic cargo proteins such as p53 and Hsp70 into living cells in vitro and in vivo (Hansen, et al., *Cancer Research*, 67(4):1769-1774 (2007), Hansen, et al., *Brain Res*, 1088(1):187-196 (2006)). More recently, the ability of 3E10 to inhibit key steps in DNA repair has been harnessed and tested for potential use in cancer therapy by sensitizing tumors to DNA-damaging agents and by selectively killing cancers that are particularly vulnerable to DNA damage such as BRCA2 and PTEN-deficient malignancies (Hansen, et al., *Sci Transl Med*, 4(157):157ra142 (2012), Noble, et al., *Cancer Research*, 2015; 75(11):2285-2291, Noble, et al., *Nat Rev Rheumatol* (2016)). However, the ability of 3E10 to penetrate nuclei and inhibit DNA repair was not critical to experiments presented herein. Instead, this work took advantage of the capacity of 3E10 to home to sites of exDNA in vivo by using it to guide the nanoparticles to tumor sites in an autocatalytic manner. This work establishes proof of concept for a lupus anti-DNA autoantibody-based approach to targeting cargo molecules including nanoparticles to sites of exDNA, which is relevant to the treatment of cancer as well as ischemic or traumatic conditions such as stroke, infarction, or injury wherein DNA is released at the site of damage.

Previous studies have found that 3E10 sensitizes cancer cells to DNA-damaging agents such as DOX, but in the experiments discussed herein the surface-conjugated 3E10$^{EN}$ did not synergize with DOX in the cell viability assays reported in FIG. 1C. This is because the 3E10$^{EN}$ was covalently conjugated to the surface of the nanoparticles and thus could not penetrate into cell nuclei to exert its biological functions. To achieve this sensitization activity, 3E10$^{EN}$ could be conjugated to the surface of the nanoparticles by disulfide bond formation. With this approach, 3E10$^{EN}$ can be released from nanoparticles once they encounter the reducing tumor microenvironment due to elevated levels of glutathione (Shao, et al., *Ther Deliv*, 3(12):1409-1427 (2012)). Alternatively, in addition to having 3E10$^{EN}$ conjugated to the surface of the nanoparticles, an amount of free 3E10$^{EN}$ may be co-encapsulated into nanoparticles along with DOX to promote simultaneous delivery of the drug and antibody fragment to cancer cells. Once released from the nanoparticles either by breakage of disulfide bonds or by release of encapsulated 3E10EN, the free 3E10$^{EN}$ would then be able to penetrate tumor cell nuclei and inhibit DNA repair and thereby sensitize the tumors to DNA damage or selectively kill DNA repair-deficient cancer cells.

In conclusion, nanomedicine has the potential to make major contributions to clinical cancer care. In the meanwhile, select lupus anti-DNA autoantibodies have emerged as possible new agents for use in cancer therapy due in part to their affinity for DNA.

Example 9: 3E10 (D31N) Di-scFv Delivers Nanoparticles into Living Cells

Materials and Methods

Cal12T lung cancer cells were treated with control buffer, free di-scFv (SEQ ID NO:12), free PLGA nanoparticles with encapsulated IR780 dye, free di-scFv+free PLGA nanoparticles with encapsulated IR780 dye, or di-scFv-conjugated PLGA nanoparticles with encapsulated IR780 dye for 20 minutes. The cells were then visualized under a fluorescence microscope to detect the IR780 signal.

Results

Significant IR780 signal was only detected in the cytoplasm of the cells treated with the di-scFv-conjugated nanoparticles, and not in the cells treated with the free nanoparticles. These data demonstrate that di-scFv can deliver conjugated nanoparticles into the intracellular compartment of living cells.

Remarkably, the IR780 signal was restricted to the cytoplasm and was not detected in the nucleus where di-scFv is expected to localize. To determine if the conjugated nanoparticles were holding di-scFv back in the cytoplasm, after visualization of the live cells, cells were then fixed and immunostained for presence of di-scFv by anti-myc immunostaining (di-scFv has a myc tag at its C-terminus). Free di-cFv penetrated into cell nuclei, even when free nanoparticles were present. However, di-scFv that was conjugated to the nanoparticles did not make it into the nucleus and was sequestered in the cytoplasm. This experiment was also performed using another cell line, DLD1 colon cancer cells, and the same patterns were observed. These data confirm that di-scFv can mediate the delivery of conjugated nanoparticles into cells, and remarkably it appears that the size of the nanoparticles restricts di-scFv to cytoplasmic localization rather than its usual nuclear localization.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A nanocarrier comprising a nanoparticle having a targeting moiety conjugated thereto and one or more therapeutic agents encapsulated therein,
   wherein the targeting moiety is an antibody that binds to DNA, and
   wherein the targeting moiety comprises the amino acid sequence of SEQ ID NO:11, 12, or 13.

2. The nanocarrier of claim 1, wherein the antibody is a variable fragment (Fv).

3. The nanocarrier of claim 1, wherein the nanocarrier is selected from the group consisting of polymeric particles, liposomes, and multilamellar vesicles.

4. The nanocarrier of claim 3, wherein the nanocarrier is polymeric nanoparticles.

5. The nanocarrier of claim 1, wherein the polymeric nanoparticles are formed of one or more biodegradable polyesters or polyanhydrides.

6. The nanocarrier of claim 5, wherein the biodegradable polyesters or polyanhydrides are selected from the group consisting of poly(lactic acid), poly(glycolic acid), and poly(lactic-co-glycolic acid).

7. The nanocarrier of claim 4, wherein the polymeric nanoparticles are formed of PLGA-poly(ε-carbobenzoxyl-L-lysine) (PLL).

8. The nanocarrier of claim 1, wherein the targeting moiety is cell penetrating.

9. The nanocarrier of claim 1, wherein the therapeutic agent is an anti-angiogenic agent, anti-proliferative, chemotherapeutic agent, cytotoxic agent, antibody or fragment or variant thereof, radiosensitizer, radioisotope, therapeutic protein, therapeutic gene, siRNA, aptamer, oligonucleotide, antisense oligonucleotide, gene modifying agent, gene expression modifying agent, or a combination thereof.

10. The nanocarrier of claim 9, wherein the therapeutic agent is a PARP inhibitor.

11. The nanocarrier of claim 10, wherein the PARP inhibitor is Olaparib ($C_{24}H_{23}FN_4O_3$).

12. A pharmaceutical composition comprising an effective amount of the nanocarrier of claim 1.

13. A method of treating cancer in a subject in need thereof comprising administering to the subject the pharmaceutical composition of claim 12.

* * * * *